United States Patent
Vacca

(10) Patent No.: US 11,903,797 B2
(45) Date of Patent: Feb. 20, 2024

(54) TAPING METHOD FOR ELICITATION OF SKELETON MUSCLE TONE

(71) Applicant: Charise Marie Vacca, Westerville, OH (US)

(72) Inventor: Charise Marie Vacca, Westerville, OH (US)

(*) Notice: Subject to any disclaimer, the term of this patent is extended or adjusted under 35 U.S.C. 154(b) by 1144 days.

(21) Appl. No.: 16/531,257

(22) Filed: Aug. 5, 2019

(65) Prior Publication Data

US 2019/0350766 A1 Nov. 21, 2019

Related U.S. Application Data

(62) Division of application No. 14/664,762, filed on Mar. 20, 2015, now Pat. No. 10,441,473.

(60) Provisional application No. 61/967,693, filed on Mar. 24, 2014.

(51) Int. Cl.
  *A61F 13/02* (2006.01)
  *A61F 5/01* (2006.01)

(52) U.S. Cl.
  CPC ............ *A61F 13/02* (2013.01); *A61F 5/0104* (2013.01)

(58) Field of Classification Search
  CPC ...... A61F 13/00; A61F 13/02; A61F 13/0273; A61F 13/06; A61F 13/10; A61F 5/0104
  See application file for complete search history.

(56) References Cited

U.S. PATENT DOCUMENTS

| | | | | |
|---|---|---|---|---|
| 2010/0016771 A1* | 1/2010 | Arbesman | ............. | A61F 13/066 602/5 |
| 2010/0233247 A1* | 9/2010 | Hohmann | ............. | A61K 36/75 424/539 |
| 2015/0217098 A1* | 8/2015 | Hicken | ................. | A61F 5/0102 607/96 |

* cited by examiner

*Primary Examiner* — Keri J Nelson
(74) *Attorney, Agent, or Firm* — Jason H. Foster; Kremblas & Foster

(57) ABSTRACT

A taping method that follows a specific set of rules based on anatomical and physiological patterns in humans. This taping method causes a change in skeletal muscle tone in the human body when tape is directly applied to the skin of the human body over the targeted muscles. This taping method will inhibit the muscle tone in the affected motor units that are underneath the tape applied in a specific inhibition method. This taping method will elicit the muscle tone in the affected motor units that are surrounded by the tape applied in a specific elicitation method. There are three different types of elicitation method patterns based on muscle size or groups of muscles, secondarily to the length tension relationship required for a muscle contraction. There is only one type of inhibition method.

5 Claims, 51 Drawing Sheets

TAPING METHOD FOR ELICITATION OF SKELETON MUSCLE TONE

CROSS-REFERENCES TO RELATED APPLICATIONS

This application claims priority to U.S. patent application Ser. No. 14/664,762, filed Mar. 20, 2015, entitled "Taping Method for Inhibition of Skeletal Muscles", currently pending, which U.S. patent application Ser. No. 14/664,762 claimed priority to U.S. Prov. Pat. App. No. 61/967,693, filed Mar. 24, 2014, entitled "PhysioSync® Neurological Taping Method", expired, which applications are incorporated herein by reference.

FIELD OF THE INVENTION

The invention is in the field of neurological and orthopedic medicine. The invention relates to the elicitation and inhibition of skeletal muscular tone with the application of adhesive medical tape directly to the skin of the human body.

BACKGROUND OF THE INVENTION

Applying adhesive medical tape to the human body was most widely used in orthopedic medicine to support joints in the human body. The tape limited the range of motion while providing support typically, to an injured joint. Orthopedic taping has also been used to prevent injury, reduce pain and swelling, as well as provide mechanical correction of ligaments and tendons. Typical sports taping techniques will revolve around the joint region. During the process of taping there are muscles that are covered, however, there is no particular assessment involving the muscle.

There are also less traditional uses for the application of adhesive medical tape to the human body. The use of adhesive medical tape applied directly to the skin of the human body has also been claimed to be used to assist in postural support, edema control, acupressure, improving circulation, and to assist with either eliciting or inhibiting muscle tone. There have been different types of adhesive medical tape developed, including tape that has increased elasticity to address the claims previously listed. These taping methods involve the application of the tape directly to the skin.

The investigation the specific claims that any of these taping processes is able to assist in either eliciting or inhibiting muscle tone is unfounded. Examinations of all these taping patterns do not reveal any specific organized pattern that would correlate with specific skeletal structures that lay beneath the tape. Elaborating on this last statement, for example, the claim that a taping pattern inhibits a muscle, the pattern of each inhibited muscle does not follow a specific pattern. A pattern is determined when it correlates with the anatomical structures underneath the tape. This is critical because the anatomy corresponds with specific physiological structures. It is the activation of the physiological structures that affect the muscle tone. Reviewing the medical literature in PubMed, these studies revealed that none of these taping patterns claiming to assist with the muscle tone have produced any effective long-term results. In theory, this would be due to the nebulous taping process that is applied in these methods that resembles no particular pattern that corresponds with anatomical or physiological structures.

It would be advantageous to come up with a taping method that was able to elicit and inhibit muscle tone that was effective, and was able to produce both short- and long-term results. This would assist in the recovery of neurological and orthopedic injuries. It would also be advantageous to have an established known pattern that was repeatable and had predictable results. In other words, it would be a true theoretical taping process. Furthermore, the taping method would be best to encompass and show efficacy in all ages of the human population that had any neurological or orthopedic disorder.

BRIEF SUMMARY OF THE INVENTION

The present invention is a taping method. This taping method is used to correct a muscle imbalance, by affecting the muscle tone, which exists in human beings. This method allows a taping of a muscle to elicit muscle tone which assists with the elicitation of a muscle contraction. This method also can inhibit muscle tone which assists with the inhibition of a muscle contraction. It will correct muscle imbalances in patients with central nervous system lesions and orthopedic injuries. After the taping methods are implemented, the patient will actually be able to utilize muscles and new muscle patterns. These patterns were either never functional before in their life, or return to some level of their previous level of muscular function. These results will occur regardless of their age; however, it is most effective with the most acute neurological injuries and with the youngest humans. This is secondarily to the increased plasticity of the nervous system in younger humans, and more acute injuries, and therefore the more advantageous the results.

This muscle taping method can inhibit muscles that have always been tight, or shortened. This can be due to high muscle tone. This taping method also can elicit muscles that have always been loose, or lengthened. The taping method does not always necessarily take away any previous movements or movement patterns; however, it will now for the first time allow new musculoskeletal movement patterns and overall muscle tone changes, that allow these new more normal movement patterns. The patient's overall muscle tone will change.

For example, with the inhibition of high tone, spastic muscles, the patient will now be able to use their arm in a more functional pattern. They will also be able to rest their arm in a more normal resting position after all the properly selected muscles are either inhibited or elicited. The degree to the extent of muscle tone changes and new more normal movement patterns are dependent on many factors. There are varying degrees of changes to being able to completely integrate into a new normal movement pattern (or rebalancing the muscle imbalance that previously existed) completely and never exhibit the old pathological movements. There are also results that vary anywhere in between, depending upon the extent of the injury, the age of the injury, compliancy of the taping method, and the age of the patient.

Specifically, for example, if a patient who is a child age 11, had a nine-year-old injury, the muscle tone changes occurred after the taping method was applied. However, when the patient would get very excited, the patient's nervous system would respond and their old pathological movement pattern would reemerge. This is an example of how a full integration of changes into the nervous system did not occur; only a partial reintegration occurred. The muscle imbalance would only reemerge under neurological stress. The patient did obtain long term changes that would occur when their nervous system was not stressed and the patient could perform more functional movements. To explain further the varying results, an example of another patient who suffered from a more mild neurological injury, that she had for a nine-year duration was able to swim for the first time in her life after applying the taping method to the appropriate muscles to correct the imbalances. This patient was able to permanently maintain this new normal movement pattern under any conditions and did not revert back to her old pathological movement patterns, even under neurological stress. This patient had a full integration of the changes into her nervous system, and in essence was completely neurologically healed. The results are so varied with this taping method. The span of the results can be to a complete healing and resolution of the muscle tone imbalances to a minimal change of the muscle tone imbalances. This is due to the fact of the wide varying factors that come into account of the patient's entire medical profile.

The end result by allowing the new movements, and movement patterns the patient's central nervous system will integrate the primitive reflex patterns. These reflexes were never integrated, as in the case of an infant or with a disorder, or become disintegrated due to an adult onset central nervous system injury. The taping method reconnects the central nervous system lesions by the afferent nervous system pathways. This is reconnected by activating the proprioceptive system. It reestablishes electrical and chemical communication distally; from the afferent pathways to the central nervous system. This afferent pathway will activate the central nervous system. The patient will be able to use muscles because the efferent pathway is either established for the first time for injuries from before birth, or reestablished since an injury that occurred after birth. Examples of injuries before birth are cerebral palsy and in utero cerebral vascular accident. Examples of injuries after birth are after cerebral vascular accident, traumatic brain injury, and seizure disorders.

This taping method is different from all the previous taping methods because this method is actually activating the central nervous system from the afferent pathway and communication to the motor cortex region of the cerebrum. The resultant cause is either reconnecting or recreating a new efferent pathway for the patient to now use, and for the first time in their life no matter what their age is. The taping method is actually redefining the way that the entire nervous system works. It is possible to have synaptogenesis or neurogenesis occur from activation only of the afferent nervous system.

The new physiological concept in conclusion, from this taping method, is that you do not have to have the origination of the signal coming from central nervous system, specifically the motor cortex of the cerebrum via the efferent pathway to command a muscle, for example, the biceps brachii to flex. This taping method starts the origination of the signal from the afferent nervous system via the proprioceptive system, that signals to the motor cortex and then through the efferent pathway to bring about the muscle tone. This is a brand-new physiological concept that in summary, states that muscle tone or initiation of a muscle contraction or inhibition of a muscle contraction can originate from the afferent pathway! A specific example is of the specifically taping the biceps brachii into an elicitation pattern. Previously, the biceps brachii that was in a reflex pattern caused by a central nervous system injury, and not functionally used throughout a person's life span after this injury. The tape activated proprioceptors that are now sending new signals to the central nervous system. The central nervous system responds to the afferent input then sends a new efferent signal. This is either new efferent pathway, or reestablished efferent pathway. This pathway is now permanently established or reestablished. The taping method, activating through the afferent pathway is allowing the brain to precisely locate the muscle (or more specifically the motor units of that muscle) that were lost after the central nervous system injury. The afferent pathway is full of proprioceptors that inform the brain exactly where all the structures are in the motor unit by communication of many different mechanoreceptors also known as proprioceptors. This activation that tells the brain specifically where these structures are again allows the reestablishment of the entire nervous system loop to occur in the motor units that have been activated by the tape.

Another example is the neurological patients that were stuck in nonintegrative primitive reflexes are now able to start to integrate these for the first time in their life. Or for the first time since their central nervous system injury occurred, after receiving this taping method.

There is a difference in the taping pattern noted in how large muscles or large muscle groups versus small muscle or small muscle groups are elicited. There are three different elicitation patterns. There is one pattern for small muscles, or small muscle groups. There are two elicitation patterns for large muscle or large muscle groups. The inhibition pattern is the same pattern regardless of the muscle or muscle group size. There is only one inhibition pattern. The specifics about which anatomical and physiological structures are being activated, and how will they are being activated will be discussed in detail later in this paper. This activation of these structures is the key to changing the muscle tone, and therefore changing and correcting the muscle imbalances.

Briefly describing the inhibition taping process is noted as follows. The inhibition taping process occurs first to relax the muscle tone. The order is from proximal to distal and lateral to medial in the human body. The tape is applied in parallel to the muscle fibers in the muscle belly. More adhesive tape, thicker tape and more layers, as the patient tolerates, are added to increase pressure and to increase activation of the proprioceptors to get the desired inhibition results. The activated proprioceptor is the muscle spindle fiber. There is only one method of inhibition.

Specifically, summing up the components this is a taping method with many different aspects. Explaining the components of this tape method are noted as follows: This taping method is one in which the practitioner applies medical adhesive tape to the skin, without penetrating the skin, to activate proprioceptors and mechanoreceptors to control tone in a skeletal muscle that has the following components: a lateral and medial surface, a proximal and distal myotendinous junction, Golgi tendon organs, Ruffini's endings, Interstitial type III and IV muscle receptors.

There are different patterns of application of the tape to cause different outcomes. The first described method will cause a muscle contraction. This application of the tape encloses a section of the muscle that will cause increased tension in the involved motor units. The application of the tape will surround a muscle and apply pressure to the muscle which will cause the activation of Ruffini's endings, and interstitial type III and IV muscle receptors. This application of tape will cause the muscle fibers to contract.

The second method of application of tape will cause an inhibition to muscle tone. The practitioner will apply the tape in parallel to activate the muscle spindle fibers, that contain nuclear bag and nuclear chain fibers. This tape will immobilize the nuclear bag and nuclear chain fibers which will then inhibit transmission of sensory information to the central nervous system. This inhibition will cause the motor neuron to stop firing, and therefore the extrafusal muscle fibers will no longer contract. The muscle tone and therefore muscle contraction will be inhibited.

The fourth method of application will cause elicitation in skeletal muscle tone in small muscles or small muscle groups. These muscles have a lateral and medial surface, as well as a proximal and distal myotendinous junction. The practitioner will apply medical adhesive tape in series at the proximal myotendinous region first. The next step is to apply the tape at the lateral surface of the proximal portion of the muscle. This tape will join up with the tape applied in series across the myotendinous junction at an angle. Next the practitioner will apply the medical tape to the medial surface of the proximal portion of the muscle, joining the tape applied in series across the myotendinous junction at an angle. The tape will then be applied in series to the distal myotendinous junction of the muscle. The lateral surface of the distal portion of the muscle will be taped next. This tape will join the tape applied in series across the myotendinous junction of the muscle. The final step is applying the tape to the medial distal portion of the muscle which joins the tape that was applied in series across the myotendinous junction.

The fifth method of application of tape will cause an elicitation of muscle tone in large muscles and large muscle groups. The practitioner will apply a method that forms a web of tape section that will join the original origin of the muscle. This method will enclose the entire muscle and will elicit skeletal muscle tone in large muscle and large muscle groups. There will be the following components: the muscle will have a lateral surface, a medial surface, a distal portion, and a proximal myotendinous junction. The practitioner will apply medical tape to the origin in series along the myotendinous junction, and selecting a new point of origin. Next the tape will be applied laterally from this myotendinous junction along the muscle going toward the new insertion. The tape will then be applied medially from the myotendinous junction along the muscle going toward the created insertion, forming an angle with the lateral tape. The tape will now be encasing the part of the muscle to be elicited and form an angle, and/or several angles. The final step is applying the tape from lateral to medial to join the new insertion. The tape will form an angle encasing the distal portion of the muscle.

The sixth method of application of tape will cause an elicitation of a large muscle or large muscle groups. The practitioner will form a web of tape section that will join up the original insertion and enclose the entire muscle, and elicit skeletal tone. There will be the following components: muscle with a lateral and medial surface a distal portion and a distal myotendinous junction. The practitioner will apply the medical tape laterally to medially to form an angle at the new origin. Next the tape will be applied laterally along the muscle from the new origin going towards the insertion. The tape will then be applied medially from the new origin going towards the insertion along the muscle. This will form an angle with the lateral pieces of tape, which will encase part of the area to be elicited. The final step is applying the tape from lateral to medial to join the insertion, taping towards the insertion such that the tape forms an angle encasing the distal portion of the muscle.

The seventh method of application of tape will cause an elicitation of a large muscle or large muscle groups. The practitioner will apply the tape to outline the original muscle. This outline will reside within the muscle itself. The first step is to select the points of origin and insertion. The new origin will be created. This is created by applying the tape first proximally at the selected points of origin. The tape will extend laterally from the new point of origin to the new insertion. The tape will end at the new points of insertion; next the tape will be applied medially from the new point of origin going towards the new insertion, and will end at the new points of insertion. The tape will create the new insertion. This insertion will extend from lateral to medial to create a new smaller version of the muscle; this is located within the muscle itself.

Specific parameters of the taping method include adding layers of tape to increase the efficacy of the taping method. The practitioner applies additional layers of tape in a predetermined pattern to the area of the muscle or muscle group.

Specific parameters of the taping method to control skeletal muscle tone, specifically with elicitation of the muscle, that has a myotendinous junction, must have the following components: a myotendinous junction, Golgi tendon organs, affected motor units. The application of medical tape by the practitioner in series along the myotendinous junction will cause activation of the Golgi tendon organs.

Specific parameters of the taping method to control skeletal muscle tone in a muscle, specifically with elicitation of the muscle that does not have a myotendinous junction, must have the following components: Ruffini's endings, interstitial type III and IV muscle receptors, and affected motor units. The application of medical tape by the practitioner by applying lateral pressure by the tape, will elicit increased tension in the muscle. The tension will specifically increase in the involved motor units of the muscle.

In summary, this taping method is what is known as a theoretical method. It is known as theoretical because the physiology is explained to act in a way that has never been explained previously in any medical literature. It is also considered theoretical because it is predictable since the outcome is known. This method is precise activating very specific structures. The brain needs to have exact and correct feedback to work properly. The other methods are not theoretical or predictable secondarily to the random patterns. The key to this working is that the brain is getting extensive, correct and exact feedback from the afferent structures in exactly the way they were meant to communicate with the brain. This also explains why there are long term results. This taping method is the only "lock and key" taping method that is exact and precise to signal to the brain that allows the exact and correct efferent response. The new pathways can be established because the brain found out exactly where the motor units are located. This taping method corrects muscle tone and therefore corrects muscle imbalance to allow a more normal movement pattern.

DETAILED DESCRIPTION

The novelty in this invention is specifically the pattern of the taping method. The pattern is very precise in the way the pattern is to activating specific physiological structures. These structures in turn cause the resulting muscle tone changes. The muscle tone changes will be either in inhibition or elicitation of muscle tone.

Specifically, with the inhibition process, the pattern is to place the tape on the human body which in turn causes pressure. Pressure activates the specific physiological structures that directly affect muscle tone. The tape is specifically applied to the specific muscle that you want to inhibit. The tape is applied in parallel to the muscle spindle fibers as well as in the muscle belly of the muscle. Explanation of this specific inhibition pattern is noted as follows. This is specific to the application based on the location and function of the structures affecting the muscle tone. More specifically, this pressure that is caused by the application of the tape that is applied in parallel with the muscle fibers, which are also known as the extrafusal muscle fibers. The muscle spindle fibers, (the intrafusal fibers), are also located in parallel with the muscle fibers. The tape must be applied in parallel to activate the structures in the muscle spindle fiber that will affect muscle tone. This pressure initially activates the muscle spindle fibers. These structures specifically respond to stretch. Their physiologic function is to sense the change in muscle length as well as sense the change in the rate of muscle length. The application of additional layers of tape will add more pressure and can be applied if needed to increase the inhibition process. The number of layers of the tape applied is recommended to not exceed five layers. Once the fifth layer is applied and the practitioner is not getting the inhibition results desired, it is recommended to inhibit synergists of the muscle that you are inhibiting. The practitioner can also elicit the antagonist of the muscle they are trying to inhibit. The specific order of the application of the tape in inhibition is to apply the tape to the most proximal muscle first. The tape is applied lateral to medial in the muscle belly and avoiding the myotendinous junction. Additional layers are added as needed following the same order as the initial application.

There are two reflexes that are in involved with the muscle spindle fibers. The first reflex is the phasic stretch reflex. This reflex is a rapid reflex that will first occur with the application of the tape. A quick stretch that initially occurs when you apply the tape activates the phasic stretch reflex which causes the muscle to contract. This is a very fast reflex that goes directly to the spinal cord this then causes the muscle (agonist) to contract and the antagonist to relax or be inhibited. This is a very brief and slight response that lasts about a second because it is such a mild application of pressure with using tape that the practitioner may see a very minimal response, and sometimes the practitioner cannot detect this response with their eyes.

The next reflex is going to occur, since the tape is still placed on the muscle. This reflex is known as the tonic stretch reflex. This reflex is a slow reflex and goes directly to the brain. It is a long and sustained response. The muscle spindle fiber that is constantly contracting and relaxing to give feedback is now in a fixed position, or immobilized, that is caused by the application of the tape. This fixed position no longer allows the muscle spindle fiber, especially the nuclear chain that is able to respond to sustained stretch (a specific structure in the muscle spindle fiber) to sense a pull on its polar attachments. Therefore, the nuclear chain can no longer send input to the structure that will sustain the muscle tone or contraction of the muscle. The nuclear bag also can no longer send input. The neuron that is responsible for having the extrafusal muscle fibers contract is known as the alpha motor neuron. The alpha motor neurons, since they are no longer receiving input form the nuclear chain (or nuclear bag to a lesser degree) stop sending impulses to the brain, specifically the motor cortex. Therefore, with the impulses stopped, there will no longer be a muscle contraction. This is isolated only to the motor unit that is being inhibited. A muscle does not contract as a whole unit, but rather in individual motor units. The tape will keep the motor unit of the muscle it is placed on inhibited or relaxed.

The human body works in many feedback loop systems. This is an example at work in the musculoskeletal portion of the human body. Without feedback from the changing position of the muscle spindle fiber, especially the nuclear chain, there is no activation of the alpha motor neuron and therefore no muscle contraction in the muscle unit that it innervates. This taping method is directly interfering with this feedback loop system and allows controlling muscle tone in the process. Emphasis is placed on the exact pattern of the application of the tape that causes this physiological response to occur every time the tape is applied. The specific parameters of the taping process for inhibition, such as the duration the tape is left on the skin to cause a permanent relaxation response is varied. The longer the tape is left on for the maximum up to seven days, the more ingrained and integrated the new response will become in the nervous system. The longer the taping method is implemented the more integration that will occur in the nervous system. The more acute injuries will require much less time to get results, versus the more chronic injuries that can take a much longer time to get results. The more acute the injury is, the more neuroplasticity that exists. The results are also more pronounced on younger patients. The more pressure that is applied by the tape either by increased adhesiveness or thickness of the tape, the more effective the inhibition process is.

Specifically, with the elicitation process, the pattern is to place the tape on the human body which in turn causes pressure. Pressure activates the specific physiological structures that directly affect muscle tone. The tape is specifically applied to the specific muscle that you want to elicit. There are differences in how you elicit smaller muscles, or small muscle groups versus larger muscles of large muscle groups.

The elicitation process of a smaller muscle, or small muscle groups; the tape is applied in series along the myotendinous junction of the muscle. These exist both proximally and distally in the muscle or muscle group. Specifically, the practitioner will be taping the myotendinous junction near the origin and insertion of the muscle or muscle group. The tape must be applied in series along the myotendinous junction. Additional tape is applied laterally and medially along the muscle, or muscle group intersecting the tape that was applied along the myotendinous junction forming an angle that looks like a "v". This occurs both proximally and distally in the muscle, again near their origin and insertion. There is not a specific angle since it is dependent on the structure of the muscle. The placement of the tape however is along the edge of the muscle, or muscle group both laterally and medially. If you are not getting enough recruitment of the muscle tension next you will apply additional tape added again as needed to increase the pressure and therefore increase the activation. The practitioner can apply as many layers as needed up to five layers. More layers of tape are equal to more increased pressure. These proprioceptive structures are all activated by pressure. The specific order of the sequencing of applying tape of elicitation for a small muscle, or muscle group is as follows: 1) Apply the tape in series the proximal myotendinous junction. 2) Apply the tape to the lateral surface of the muscle or muscle groups, joining the tape applied in series across the myotendinous junction. 3) Apply the tape to the medial surface of the muscle, or muscle groups, joining the tape applied in series across the myotendinous junction. 4) Apply the tape in series the distal myotendinous junction. 5) Apply the tape to the lateral surface of the distal portion of the muscle, or muscle groups, joining the tape applied in series across the myotendinous junction. 6) Apply the tape to the medial surface of the distal portion of the muscle, or muscle groups, joining the tape applied in series across the myotendinous junction. 7) Apply additional layers of tape as needed to get the desired results typically up to five layers.

These additional layers will be applied in the same sequence as previously listed. There will be an angle formed at each end of the muscle that was taped. The practitioner can also elicit synergists when applicable to increase the desired results, as well as inhibit the antagonist.

The specific parameters of the taping process for elicitation such as the duration that the tape is left on to cause a permanent excitatory response is varied. The longer the tape is left on for the maximum up to seven days, the more ingrained and integrated the new response will become in the nervous system. The longer the taping method is implemented the more integration that will occur in the nervous system. The more acute injuries will require much less time to get results, versus the more chronic injuries that can take a much longer time to get results. The more acute the injury is, the more neuroplasticity that exists. The results are also more pronounced on younger patients. The more pressure that is applied by the tape either by increased adhesiveness or thickness of the tape, the more effective the elicitation process is.

Elicitation of a large muscle or large muscle groups; there are two ways to perform elicitation of a large muscle or large muscle group. This is depending on the structure of the muscle or muscle group. However, in both methods the entire "muscle" must be encased by applying adhesive tape to produce enough muscle tension in every direction. Both elicitation processes still follow the same sequence of going proximal to distal and lateral to medial when applying the tape.

The first method occurs in a large muscle or large muscle groups. This taping method is specifically able to elicit skeletal muscle tone in the affected motor units, specifically in large muscle, or large muscle groups, by the application of medical adhesive tape in the following pattern: 1) Select either the insertion or the origin of the large muscle, (or large muscle group) that has the most accessible and largest area of the myotendinous junction available. 2) Apply the tape to the most proximal region first. This region can either be the created origin or the original origin. 3) If it is the original origin that was selected, apply the tape in series along the myotendinous junction, and select the new points of insertion. 4) Apply the tape laterally from the myotendinous junction along the muscle going towards the created insertion. 5) Apply tape medially from the myotendinous junction along the muscle going towards the created insertion, forming an angle with the second piece and encasing part of the area to be elicited. 6) Apply going from lateral to medial as many pieces of tape it takes to join up to the origin always taping towards the new insertion. 7) Tape is applied at the newly formed insertion forming an angle, and encasing the entire area of the muscle to elicit. A continuation of the tape has now been formed as it includes the original origin of the muscle to enclose the entire "new muscle" that is now formed.

This first method can also occur when the practitioner selects the insertion. The pattern will slightly change. The process is noted as follows, and the application of medical adhesive tape in the following pattern: 1) Select either the insertion or the origin of the muscle (or group of muscles) that has the most accessible and largest area of the myotendinous junction. 2) Apply the tape to the most proximal region first. This region can either be the created origin or the original origin. 3) If it is the original insertion that was selected, a new origin is created 4) Select new points of origin. 5) Apply the tape to the new points of origin laterally along the muscle going towards the insertion. 6) Apply the tape to the new points of origin medially along the muscle, going towards the insertion, forming an angle with the first piece and encasing part of the area to be elicited. 7) Apply tape going from lateral to medial as many pieces of tape it takes to join up to the insertion always taping towards the insertion. 8) At the insertion, apply the tape in series along the myotendinous junction taping until whole myotendinous area is taped. A continuation of the tape has now been formed as it joins up with the newly formed origin and encloses the entire "new muscle" that is now formed. The practitioner can also inhibit the antagonist synergists to increase the desired results. There may also be some synergists that could be elicited if they were not all encompassed in the elicitation process.

The second option is to create both a new origin and insertion of the muscle. The practitioner is creating a "new muscle". In this method the practitioner will take out a smaller part of the larger muscle. This occurs by placing tape in an outline of the original muscle. The entire "new muscle" is outlined. Simply stated it is a smaller version of the muscle itself. This taping method is specifically able to elicit skeletal muscle tone in the affected motor units, specifically in large muscles or large muscle groups, by the application of medical adhesive tape in the following pattern: 1) Apply the tape by creating a small outline of exactly the same shape of the original muscle or muscle group within the muscle or muscle group itself; 2) Points of origin and insertion are selected; 3) Apply the tape first proximally creating the new origin, starting at the selected points of origin; 4) Apply this tape laterally coming from the new points of origin going towards the new insertion, ending at the new points of insertion; 5) Apply the next piece of tape medially coming from the new point of origin going towards the new insertion, ending at the new points of insertion; 6) Apply the tape creating the new insertion from the selected points of insertion from lateral to medial; 7) Completion of the application creates a new smaller version of the muscle or muscle group itself located within the muscle or muscle group. Additional tape may need to be applied before the completion of step 7 depending on the size of the large muscle or large muscle group being elicited. The practitioner can also inhibit the antagonist synergists to increase the desired results. There may also be some synergists that could be elicited if they were not all encompassed in the elicitation process The same parameters exist in both elicitation processes that were mentioned in the inhibition process as well as in the elicitation process for small muscles or small muscle groups. Repeating these parameters again is as noted. The specific parameters of the taping process for elicitation such as the duration that the tape is left on to cause a permanent excitatory response is varied. The longer the tape is left on for the maximum up to seven days, the more ingrained and integrated the new response will become in the nervous system. The longer the taping method is implemented the more integration that will occur in the nervous system. The more acute injuries will require much less time to get results, versus the more chronic injuries that can take a much longer time to get results. The more acute the injury is, the more neuroplasticity that exists. The results are also more pronounced on younger patients. The more pressure that is applied by the tape either by increased adhesiveness or thickness of the tape, the more effective the elicitation process is.

The first option is attempted first to get an elicitation of the muscle tone. If this option fails then the second option will be initiated. The reason that there are exceptions to elicitation with large muscles is that the length tension relationship is a huge factor, and there must be enough tension to cause a contraction. The length or distance on large muscles are shortened by creating a new origin, or insertion or by creating both a new origin and insertion if the first option did not work to elicit a muscle contraction. It is also noted that the small muscle or small muscle group may also be totally enclosed as a last result to get an elicitation response. This is very rare that this would occur, and is discouraged from general practice, secondarily to it being beneficial to the patient to put as little tape as possible on the patient to get a desired response. It is mentioned just as a very last resort, and not commonly practiced.

The elicitation process, also known as the process to increase muscle tone, is more complicated than the inhibition process. The key to elicitation is based on the physiological process of how a muscle contracts. The length tension property in getting a muscle to contract is critical. The elicitation process is to increase the tension in the muscle, to allow a muscle to increase tone, and set it up to allow a contraction to occur. There are several physiological structures involved in the elicitation process. This is very different from the inhibition process that has only one structure involved. The length-tension property takes into account muscle size, volume and length of the muscle. The larger the muscle the more difficult it is to increase tension. Therefore, the smaller the muscle the easier it is to increase tension. It is for this reason that there are some differences in the elicitation process of larger muscles verse smaller muscles. The larger muscles require additional recruitment of muscle tension, producing physiological structures and properties. The following physiological structures are involved in the elicitation process: Golgi tendon organs, Paciniform corpuscles, Pacinian corpuscle, Ruffini endings, interstitial Type III and IV muscle receptors, and the extrafusal muscle fibers themselves, with their inherent ability to contract. Each structure will be described in detail and their role in eliciting increase in muscle tone that is required for a muscle to contract.

Specific details on the physiological mechanism that occur to elicit increased muscle tone will be explained in detail. The application of tape in series along the myotendinous junction will cause an elicitation the Golgi tendon organs. These structures sense muscle tension as well as the rate of change of muscle tension. Initially the phasic reflex is known as the clasp-knife reflex or autogenic inhibition. This reflex inhibits the muscle it is receiving the information from. The clasp-knife reflex only works when there is a rapid change in tension as a protective response. It is a phasic reflex that goes directly to the spinal cord. This phasic reflex is an inhibitory response.

Studies also support that Golgi tendon organs are not just inhibitory. There are studies that show that the Golgi tendon organs are activated during ambulation in humans. This is considered to be a reflex reversal and autogenic inhibition is suppressed. This is suppressed by inhibiting the 1b interneuron. This interneuron when it is suppressed stops the inhibition process of a muscle contraction. Therefore, it now is allowing a muscle to contract. This reveals that the Golgi tendon organs are involved in eliciting a muscle contraction. When the tape is applied in series along the myotendinous junction the Golgi tendon organs that house the Type 1b afferent nerve causes an activation of this sensory nerve. This nerve sends an afferent impulse directly to the motor cortex in the cerebrum. This allows the brain to know exactly the location of this muscle, specifically the motor units of that muscle. The pressure is steady and light. This pressure activates the tonic reflex involved in ambulation. This in turn allows for a recruitment of muscle tension. There is also a phenomenon known as the spike train response. This response is being activated that allows for additional recruitment of other Golgi tendon organs in the region, to assist with the muscle contraction. This would occur with a constant light pressure applied that elicits the tonic reflex.

In summary, both the inhibition taping method of the muscle spindle fibers and the elicitation taping method of the Golgi tendon organs are activating a slow, tonic reflex. These tonic reflexes go directly to the brain, specifically the motor cortex. This is why there is a motor effect, the increase or decrease in muscle tone, as well as a long-term effect. It is directly affecting the brain, which has the proven ability of neuroplasticity. This is not the typical phasic reflexes these two structures are very well known and documented in the medical literature. This is the atypical tonic reflexes that are activated in this taping process.

The tape applied in series along the myotendinous junction; also activate the Paciniform corpuscles that are also activated by pressure. These are mechanoreceptors. The Paciniform corpuscles sense rapid pressure changes and vibration that contribute to kinesthetic sense. The known response of these structures is that they contribute to kinesthetic sense as well as a role in movement. These are located in the myotendinous junction as well as the joint capsules. These locations are also where the Golgi tendon organs are located. There is little information about this mechanoreceptor. It is likely that these structures are assisting the Golgi tendon organs, and assisting in additional aid to help the brain find the muscle.

The Pacinian corpuscle is also a mechanoreceptor. It is located in the deep skin both hairy and nonhairy regions, especially in tendinous sites, the deep portion of joint capsules, and spinal ligaments. These structures respond to rapid deep touch and vibration. The activation of these structures contributes to a kinesthetic sense. The application of tape applies pressure and activates these structures. The activation of these will further help the brain locate the muscle. These would be active underneath the tape that is applied all along the skin.

The Ruffini endings are mechanoreceptors. These respond to sustained pressure especially laterally applied tape. These are located in deep skin, ligaments of peripheral joints, joint capsules and dura mater, and other tissues associated with regular stretching. The tape that is applied laterally in the elicitation process would be activating these Ruffini endings. These are known to have a role in movement control. The activation of these would further help to exactly locate the muscle and help the brain find the muscle to assist in muscle contractions. These structures are more critical to the elicitation taping process since they respond to sustained pressure which would be the tape that is applied. The tape is left on for long periods of time allowing the Ruffini endings to continually activate. They are also critical for the lateral and tangential pressure applied by the tape.

Interstitial Type III and IV muscle receptors. These receptors are interstitial muscle receptors. These respond to both rapid and sustained pressure changes. The tape is applied in any direction these mechanoreceptors are activated beneath the tape. They are actually located almost everywhere in the body (they are found in bones). They exist in fascia. These are the most abundant mechanoreceptor. They are known to respond as a mechanoreceptor. Therefore, once activated by the tape they assist the brain in finding exactly where the muscle and muscle extrafusal fibers are located.

Muscle fibers (extrafusal) are themselves inherently contractile. Extrafusal muscle fibers are designed to contract easily. They are noted to have optimal length-tension relationship to allow a contraction to occur. The application of tape surrounding a muscle applies pressure to the muscle and sets up the muscle fibers themselves to contract. The application of the tape for elicitation of large muscles, or large groups of muscles requires an enclosure of the "new muscle". This is setting up pressure within the encased region to assist with increasing tension.

There are additional items to consider when taping the muscle to produce either an inhibition or elicitation response in the muscle. There are many different types of adhesive medical tape that the practitioner can select to perform this taping method. The selection of medical adhesive tape must take into account the patient's skin sensitivity. The first layer of tape, especially, must account for skin sensitivity. There are tapes that are hypoallergenic. It is recommended to perform an allergy test prior to application of the tape to ensure a safe treatment. Additional layers of tape placed on top are not as critical to assess the type of adhesive, secondarily to not having direct contact with the skin. The additional application of tape is synonymous to additional application of pressure. The more adhesive properties the tape has translate to more pressure that will be applied to the proprioceptors and mechanoreceptors. All the structures that are activated in this taping method are activated to or respond directly to pressure. It is important not to select any adhesive medical tape that is elastic in its properties in any way. If a tape has elasticity, it greatly compromises the effect of pressure, and therefore the entire effect on trying to obtain either elicitation of inhibition.

The amount of tape applied is to produce an effect should be to apply as little of tape as possible to decrease the chance of skin irritation. If the desired results are not obtained, then additional layers of tape can be applied. It is in general recommended not to exceed five layers for either the elicitation or inhibition process, however this is not mandatory. These parameters were set to assist with increase efficiency in the taping process. The recommendation for inhibition once the practitioner reached 5 layers is to next inhibit the synergist to obtain the desired results. The recommendation for elicitation once the practitioner reaches five layers is to elicit synergists. There is also the option to tape antagonist with both inhibition and elicitation and this will be covered later.

The direction of the tape applied is going from proximal to distal in the human body. The human nervous system is what is specifically being affected through this taping method. This system of nerve innervation also starts proximally to distally. The effect of the application of the tape starts to affect the nervous system proximally first. These affects will trickle down and can affect the next muscle the practitioner has selected to tape. This may affect the muscle tone very favorably and require less tape as the process of taping is moved more distally. The direction also must be lateral to medial when applying tape to a muscle. The reason it is applied laterally first is this is a less sensitive region. This helps to desensitize the patient being taped when taping less sensitive regions first.

Application of the tape in regards to sensitive areas would be to tape the most sensitive region last. The reasoning behind this sequence is to again allow the patient to adapt to the pressure of the tape and allow the integration process to begin. The sensitive region needs to be taped last to allow the effectiveness of the tape in other regions to occur. This is especially true if the patient is unable to tolerate the more sensitive regions, and the taping needs to be abandoned in the sensitive regions. The whole taping process would be abandoned if starting in the sensitive region first. The most sensitive region that would be taped is the face. The next most sensitive region is the neck. The next region would be the soles of the feet and palms of the hands. It is also important to ask the patient that is being taped what regions are most sensitive to them. Each individual is different, and may have different regions that they would consider sensitive. If the patient is unable to communicate this, ask someone who is familiar with the patient.

The process that is required to perform first would be the inhibition process. All the muscles and regions selected for inhibition needs to be performed first. The reason for starting with the inhibition process is to allow relaxation of the patient and decreased muscle tone. Once the muscle tone has been decreased it is much easier to access regions that require elicitation. It is best for the patient to enable them to relax at having a procedure performed on them. It is also best for the practitioner making the elicitation process easier and having the patient more relaxed.

The amount of time that the tape is left on will vary. The initial allergy testing of the tape begins prior to beginning the actual treatment the tape will be left on the back for 12 to 24 hours. The wearing time for the initial treatment session will be 48 hours and will increase up to seven days. The practitioner will decide the amount of time that is optimal after the initial treatment session. The tape cannot be left on any longer than seven days. The skin could start to breakdown after seven days and this could injure the patient. There must be a two-day period of no tape on the skin before reapplication of the tape. This is necessary to allow the tissue to have contact with the air and become dry.

The frequency of application of the tape is determined by the patient's response. The initial allergy testing does not interfere with application occurring the very next day if the tests come back as normal. The tape will initially be applied on a once a week frequency. The tape can be applied more than once a week if it should come off from contact with water or by sweating. The tape can be applied after a 48-hour rest, once the tape came off. The exception to this rule is tape that is applied to either the plantar surface of the feet or palms of the hands. These regions can be taped daily, as long as excessive, moisture is not collecting, or skin breakdown occurring.

The practitioner must determine if application of the tape to the skin is appropriate. The skin must be in what is considered a normal state. The skin needs to be dry, free of any type of abrasion, wound, bruising or any type of irritation. The skin cannot be inflamed or swollen. The skin must be checked after each application of tape, to make sure it is in the previous normal state, before attempting to apply additional tape.

An extensive medical history of the patient must be taken to determine if they are a candidate for the taping process. The patient's age and past medical history must be known. This medical history also needs to include a medication list. This is important because certain medications can cause increased skin sensitivity. Antibiotics and chemotherapy drugs are two well-known drugs that can affect skin sensitivity. The practitioner must be aware of all the medications that can cause skin sensitivity. MD clearance is required before proceeding with taping if the patient is on drugs that increase skin sensitivity. A patient that has any skin or vascular disorder must have their physician's clearance before proceeding with the taping process. Various medical factors must be taken into consideration before proceeding with the application of tape. Allergies that the patient currently has must also be known. Especially important is if the patient has any adhesive allergies. Other allergies that are of importance are latex, rubber, avocado and banana allergies. The latex and rubber could be found in the tape. If a patient has a banana or avocado allergy they are more likely to have latex allergies.

The actual property of the muscles must be considered before proceeding. There are 17 different properties of the muscles or muscle groups to take into consideration before proceeding with the application of adhesive medical tape.

The first property is the surface area of the muscle or muscle group. The larger the surface area of the muscle, the more difficult it is to elicit muscle tone. The surface area affects the length tension relationship of the muscle. There are three elicitation processes to choose from to elicit a muscle contraction. If the surface area is large, the practitioner may need to choose from the two options when eliciting a large muscle or large muscle group. This will also make it more difficult for inhibition, secondarily to a larger surface area. The application of more tape to increase the pressure to activate the inhibition of muscle tone may be required. The consideration of inhibiting a synergist might also be required. This also is one explanation of why it is more effective to perform this taping method on infants and children. They have smaller muscle surface area. This will enable a better length tension relationship to allow a contraction. This will also make it more effective to inhibit the muscles.

The second property of the muscle or muscle groups is to consider the volume of the muscle or muscle group. The larger the volume of the muscle, the more difficult it is to elicit muscle tone. The volume of a muscle also affects the length-tension relationship. The other factor to consider with the volume of the muscle is that a muscle contracts by motor units. Therefore, if a muscle has a large volume only the surface area of the muscle motor units will be affected. This also explains why it is easier and more effective to perform this taping method on infants and children. They are small and have smaller muscle volume. This will enable a possible elicitation of all of the motor units in the muscle, or at least recruit in more motor units of the muscle.

The third property of the muscle or muscle group to consider is the exact shape of the muscle or muscle groups. The shape of the muscle must be known to enable the correct placement of the tape. The tape is placed along the muscle or muscle groups laterally and medially with elicitation. The length tension relationship must also be considered. This is also important with the inhibition process. The practitioner must locate the exact area of the muscle belly to enable proper inhibition taping.

The fourth property of the muscle or muscle group to consider is the action that the muscle or muscle group performs. The practitioner needs to be aware of the full range of motion movement of these muscles. The way the tape is applied, and what position the part of the body that is being taped is important. Specifically, if a muscle being taped extends a joint, and this joint also can flex. It is important to place this body part in a position that will allow the movements, without being restricted by the tape applied.

The fifth property of the muscle or muscle group to consider is the actual length of the lever arm involved in the movement of the joint that the muscle is attached to. The longer the lever arm, the more difficult the elicitation of the muscle tone to occur. A long lever arm requires a powerful muscle or group of muscles to move it. The practitioner needs to consider the three options for elicitation, and which one would best fit the mechanical situation of the lever arms. The inhibition process will also be more difficult with a longer lever arm again secondarily to the size and power of the muscle and/or muscle groups involved.

The sixth property of the muscle or muscle group to consider is where the origin and insertion of the muscle are, and how far apart they are in relation to one another. Therefore, if the origin and insertion are far apart or span across multiple bony structures, this makes the elicitation process more difficult. The practitioner needs to consider if the option of changing the insertion or origin is required to get a proper elicitation. The second option of making a smaller muscle also needs to be considered.

The seventh property of the muscle or muscle group is to consider the location of the myotendinous region; and therefore, the location the Golgi tendon organs which are oriented in series. The Paciniform and Pacini corpuscles are also located in the myotendinous junction. The practitioner needs to observe if they are located close enough together to perform the first elicitation process. If they are not, then the practitioner must select which region has the most available area of the myotendinous junction to keep. The practitioner needs to create a new origin or insertion. The practitioner must also consider if this region is prominent enough at all, and may need to select the third elicitation option. The location of the myotendinous junction is also critical for the inhibition process. When applying the tape for inhibition it is critical to keep the tape out of the myotendinous junction, so as to not accidentally also start an elicitation process.

The eighth property of the muscle or muscle group is to consider is direction of the muscle fibers, specifically the extrafusal muscle fiber, and therefore the location of the muscle spindle fibers. The tape must be applied in the same direction of the extrafusal muscle fibers. This was previously explained in detail.

The ninth property of the muscle or muscle group to consider is the location and distribution of mechanoreceptors, and proprioceptors. This is critical especially in the elicitation process. They are the following: muscle spindle fibers, Golgi tendon organs, Paciniform corpuscles, Pacinian corpuscle, Ruffini endings, and interstitial type III and IV muscle receptors. This was previously explained in detail.

The tenth property of the muscle of muscle groups is to consider agonist/antagonist relationship. This is critical in both the elicitation and inhibition taping process. The agonist will be the original muscle that the practitioner either wants to elicit or inhibit. If the results are not being obtained after a reasonable amount of tape application to the muscle, then the option to involve the antagonist must be considered.

If the practitioner wants to inhibit a muscle contraction, and decrease the tone, and is unable to get the desired effects, the option to elicit the antagonist is available. This will assist in two ways. First physiologically, when the practitioner elicits the antagonist it will inhibit the agonist. The second way is that by eliciting the antagonist it will increase the muscle tone, and elicit a stronger contraction encouraging a lengthening or stretching, relaxation of the agonist and a stretching of the overall, muscle belly.

If the practitioner wants to elicit an agonist and is not able to get the desired effects, then the inhibition of the antagonist is an option. This will assist also in two ways. First physiologically, when an antagonist is inhibited the nervous system elicits the agonist. The second way is that by inhibiting the antagonist it will decrease the muscle tone and elicit a weaker muscle tone allowing the agonist to overcome it and increase the ability to contact.

The eleventh property of the muscle or group of muscles to consider is the agonist/synergist relationship. If the practitioner is trying to elicit an agonist and is not able to get the desired effect, then eliciting and recruiting in synergists will assist in getting the desired movement. Synergists work together in the musculoskeletal system to aid in being able to work in unison to get the desired movement pattern. If the practitioner is trying to inhibit an agonist and is not able to get the desired effects, inhibiting the synergists will assist in getting the desired movement. Synergists work together and by inhibiting the synergists as well this will assist in getting the desired movement pattern.

The twelfth property of the muscle or group of muscles to consider is the location and presence of vital structures such as veins, arteries, and nerves. The practitioner must have knowledge of other physiological structures that could react, or be affected by the taping process in some way. There are fragile structures that need to be avoided such as vessels. The taping process needs to avoid these structures to keep the patient safe, and allowing normal physiological responses to occur, and not be interfered by the taping process.

The thirteenth property of the muscle or muscle group to consider is identifying the muscle imbalances that exist. This is a very involved and complicated procedure especially with neurological patients. There are many factors involved in this process that need to be observed. The practitioner needs to be very well educated and trained in identifying neurological deficits. The following is a list of items to consider, however it is not fully inclusive: primitive reflexes, integrated versus nonintegrated reflexes, central nervous system injury reflexive patterns, compensatory movement patterns, synergy patterns, weak versus strong muscles, tight versus loose muscles, and skeletal structure based on structure of the bones. Some bony pathology to observe and consider are the following: genu valgus, genu varus, scoliosis, kyphosis, pes planus, and consider past musculoskeletal injuries.

The fourteenth properties of the muscle or muscle group to consider are specifically lateral pressure required for the elicitation taping process. This is the activation of Ruffini's endings, and interstitial Type III and IV muscle receptors. However, take note that all of the mechanoreceptors respond to pressure. The two listed respond especially to the lateral pressure. Another item to consider is the inherent property for muscles to contract. The lateral pressure applied to pinch the muscle on both the lateral and medial side of the muscle assists in eliciting a muscle contraction, secondarily to the inherent property.

The fifteenth properties of the muscle or muscle group to consider are enclosure needed for large muscles or muscle groups. They must be enclosed to get elicitation of Ruffini's endings, interstitial type III and IV muscle receptors. The enclosure also activates the Paciniform corpuscles and possibly Pacinian corpuscles. These structures all assist to get the proper length tension relationship of the muscle. The muscle fibers are also increasing in the tension inherently themselves and are primed to contract. It was mentioned that small muscle and small muscle groups can be enclosed for elicitation. This also is utilized as a last resort and is not the common practice for elicitation of the smaller muscles.

The sixteenth property of the muscle or muscle group to consider is pressure required. Pressure is equal to the number of layers of tape required getting the proper results. This was previously covered and there are no specific limits to how many layers of tape need to be applied to get an elicitation or inhibition. The recommendation is not to exceed five layers for either elicitation or inhibition to be most efficient in practice. Other strategies were already covered to assist with either elicitation or inhibition.

The seventeenth property of the muscle of muscle group to consider is overall length tension relationship of the entire muscle in relation to itself, and the lever arms involved for the movement. The muscle requires a specific optimal length tension in order to contract. The muscle is made up of motor units. Motor units are what contract. Each motor unit contracts in a way that is referred to as an all or nothing contraction. There is no such thing as a partial motor unit contraction, and therefore the length tension must also be correct or optimal to work.

The actual property of the tape must be considered before proceeding. There are eight different properties of the tape to take into consideration before proceeding with the application of adhesive medical tape.

The first property of the tape to consider is adhesiveness of the tape required. The more adhesive property of the tape will translate to more pressure being applied. The practitioner will select the tape based on the need for the amount of pressure to elicit the desired results. Infants up to toddlers cannot have strong adhesive tape because of their delicate skin. The tape adhesions that can be tolerated are either paper tape or cloth tape. The paper tape has the least amount of adhesion followed by the cloth tape. For the purposes of taping the following classification system was developed to gauge the delicate nature of human skin. Infant are classified up to age one. Toddlers are classified up to age three. Children also have delicate skin and cannot tolerate tape that has a lot of adhesion. They can tolerate paper tape, cloth tape and typical athletic tape. Children are classified from age three to seven. The tapes all listed paper, cloth and athletic do not require an undercoat because the adhesive property is not severe enough to require a protective undercoat. The order of least adhesive to most adhesive are noted as follows: paper, cloth, athletic. The most adhesive tape are name brands of adhesive sports tapes, some examples are Endura®, Leukotape® and Anchor® rigid strapping tapes. There are also other sports tapes that also have strong adhesive properties. All of these sports tape require an undercoat to protect the skin.

The second property of the tape to consider is stretchiness of the tape, and if undercoat tape required. To properly perform this taping method, the tape utilized cannot have any stretchiness at all. If the tape has any elasticity at all it will affect the ability to apply pressure. None of the tape can have any stretchy properties. An undercoat tape is only required if the tape selected has a strong adhesive property. The undercoat should be hypoallergenic.

The third property of the tape to consider is breathability of the tape. This is specifically addressing the undercoat tape. The undercoat tape needs to have some ventilation to allow for longer wearing time since the tape that is applied on top of the undercoat has extensive adhesive properties and is denser. The other named less adhesive tape is paper, cloth, and athletic tape.

The fourth property of the tape to consider is thickness of the tape. The thicker the property of the tape will translate to more pressure that is applied. The practitioner would select a thicker tape to apply when selecting to apply more pressure.

The fifth property of the tape to consider is width and length of the tape. The practitioner needs to select the proper width and length to properly cause a desired activation. The smaller muscles must have the proper tape to not go too far into the muscle to interfere with activation, or too far into the myotendinous junction to interfere with inhibition. The tape parameters must fit the muscle size/parameters.

The sixth property of the tape to consider is substances in the tape. It is important to consider the allergies a patient might have. All tape must be allergy tested on the patient before attempting to use the tape for treatment. The questions to ask are the following: Is the tape latex free or not? Is the tape hypoallergenic? Does the tape contain rubber? Does the tape have any toxic substances? It is recommended to thoroughly examine all substances in the tape before selecting it as a possible tape to utilize.

The seventh property of the tape to consider is the amount of tape required to do a proper taping to muscle or muscle groups. Larger amounts of the tape are required at broad surface areas, and to bring the edges closer together. The direction is superior to inferior and lateral to medial or reverse. Lateral pressure must be also maintained. Note that with the larger muscles, the whole muscle (or "new" smaller version of the muscle) must be enclosed by the tape. This was described in detail earlier.

The eighth property of the tape to consider is proper sequencing to apply the tape: beginning with inhibition taping process first, followed by elicitation taping process. Tape first going from proximal to distal, and then followed by lateral to medial application of the tape. Sensitive structures are taped last. This was revealed in detail previously.

BRIEF EXPLANATION OF THE DRAWINGS

The illustrations of all the figures are showing in detail all the taping methods in a step by step taping process that were discussed in this paper. Specifically, there are a total of four different taping methods. One taping method is the inhibition taping process, and three of the methods are elicitation taping processes. The illustrations are revealing the inhibition taping method on small muscles, and large muscles. The illustrations also reveal the elicitation process on small muscles as well as on large muscles and large muscle groups. There is not an illustration of the elicitation of small muscle groups since it is performed just like the elicitation on a small muscle. The first elicitation method where the practitioner chooses an origin or an insertion, only one way was selected for the illustrations. The illustrations show the selection of the original insertion of the quadriceps femoris muscle group.

There is only one inhibition taping method process. This is displayed in the illustrations of two different muscles. The small muscle group illustration is of the biceps brachii. The large muscle illustration is of the latissimus dorsi. The inhibition method is the same regardless of the muscle size, or group of muscles. The inhibition was shown on small and large muscles for clarification, even though all the inhibition is the same method. The inhibition process visually looks different when looking at a large versus a small muscle.

Figure 1:
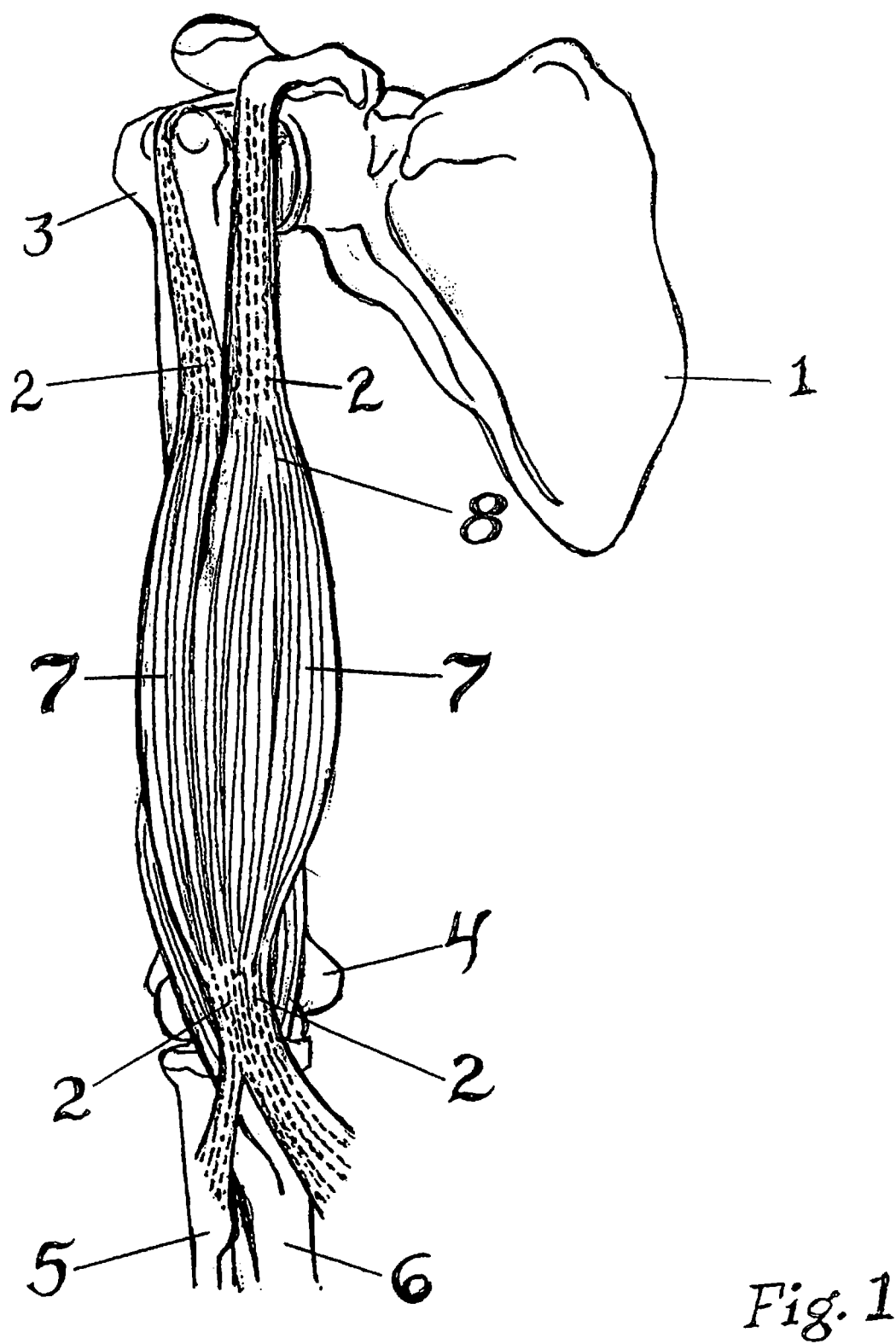

There are three elicitation taping method processes. The first elicitation process is eliciting a small muscle or small muscle group. Elicitation of the small muscle was chosen and is displayed in the illustrations specifically of the biceps brachii muscle. The second elicitation process, eliciting a large muscle or large muscle group is displayed in the illustrations specifically of the quadriceps femoris group, which is considered a large muscle group. This second method is the method of elicitation that the practitioner creates a new origin. The third and final elicitation taping method, displayed is specifically of the latissimus dorsi muscle which is considered a large muscle. This third elicitation method is the method in which a new muscle, a smaller version of the muscle itself is created. The myotendinous region for reference of taping is displayed as small dots. It is worth noting that either of these elicitation processes can occur in a large muscle or large muscle group; however, one was selected to show the specific sequencing. Clarifying this point, the latissimus dorsi could also be elicited by selecting a new insertion. The quadriceps muscle could also be elicited by creating a smaller version of the muscle group within itself as well. There are many different angles created when performing an elicitation taping method. There is not a specific angle required, however it is optimal to get angle that forces a pinch to the muscles and also includes any myotendinous junction region that is applicable in the taping.

There are a total of two layers of tape applied in the drawings. This is both for the inhibition and elicitation taping methods. It is noted that there is no limit to the layers applied, however typically up to five is recommended to be efficient.

BRIEF DESCRIPTION OF THE DRAWINGS

FIG. 1. is a drawing of the right upper extremity, biceps brachii muscle. 1. the scapula; 2. myotendinous junction(all dotted lines represent the myotendinous junction); 3. proximal portion of the humerus; 4. medial epicondyle; 5. proximal portion of the radius; 6. proximal portion of the ulna; 7. muscle belly of the biceps brachii muscle; 8. a muscle fiber (extrafusal fiber).

Figure 2:
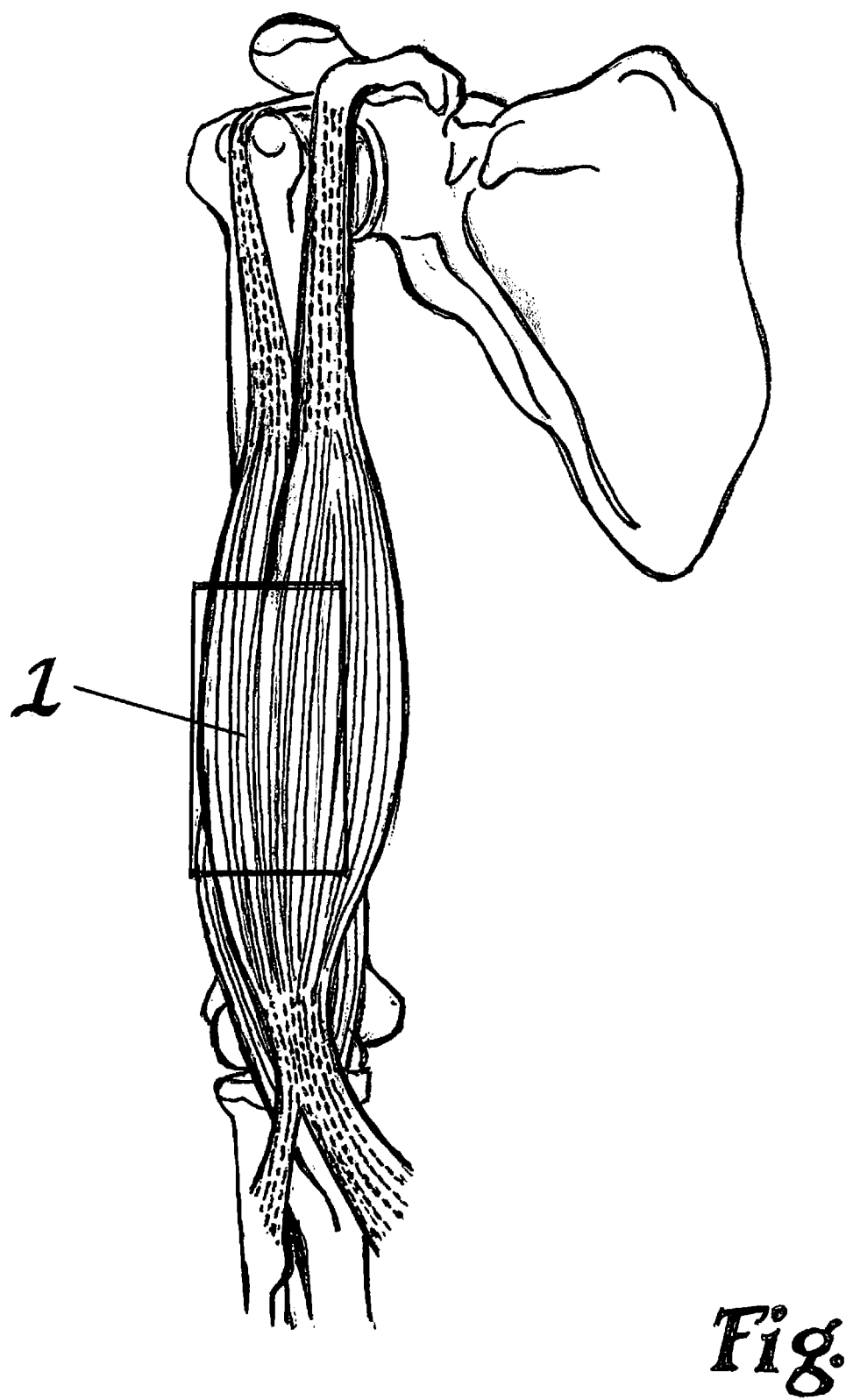

FIG. 2. is a drawing of the application of adhesive medical tape applied to the biceps brachii for the inhibition taping method. There is one layer of the tape that is specifically applied to the belly of the muscle. The tape is applied in parallel to the direction of the muscle fibers. The tape must not enter the myotendinous junction, and be applied only to the belly of the muscle, for any of the inhibition taping.

Figure 3:
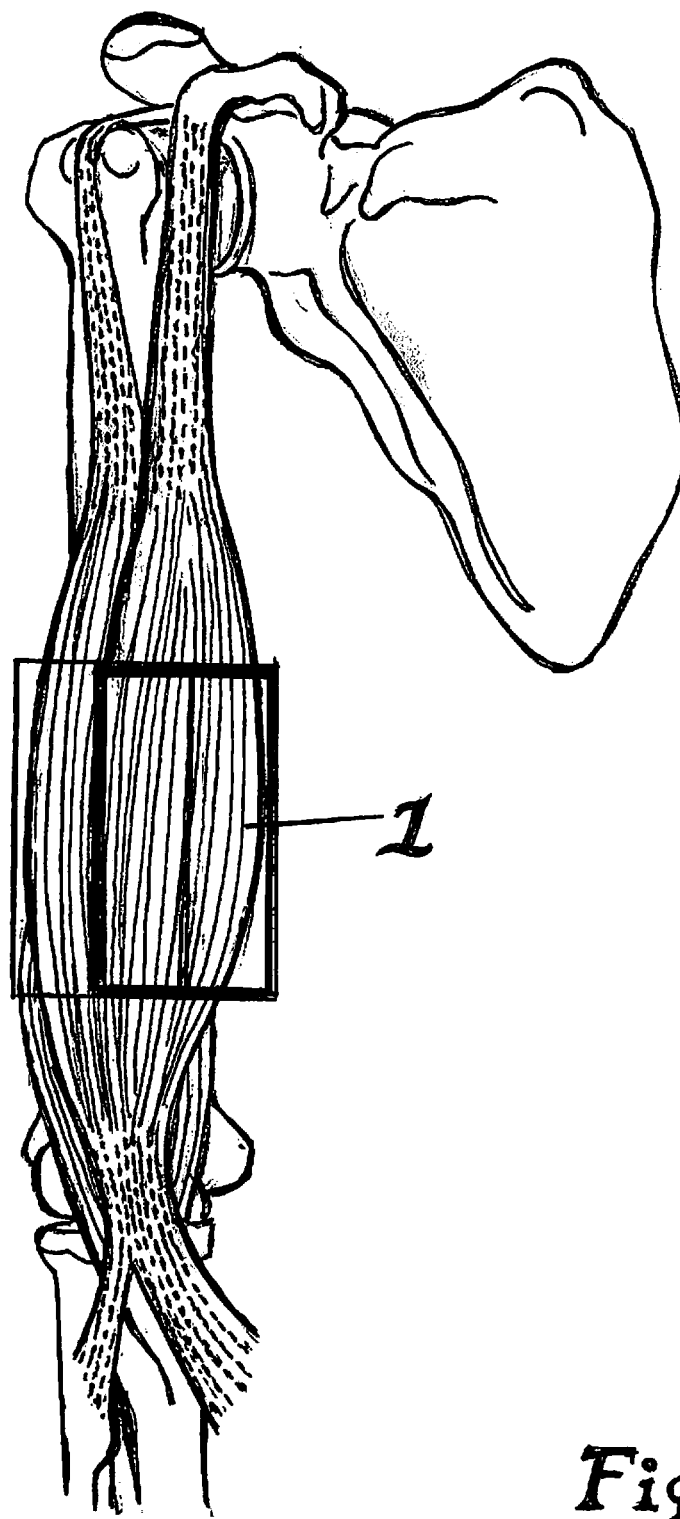

FIG. 3. is a drawing of the application of the adhesive medical tape applied to the biceps brachii for the inhibition taping method. There is one layer of the tape that is specifically applied to the second belly of the biceps brachii muscle ensuring complete coverage of the belly of the muscle. The tape is applied in parallel to the direction of the muscle fibers. The tape must not enter the myotendinous junction, and be applied only to the belly of the muscle. The tape overlaps the first piece applied.

Figure 4:
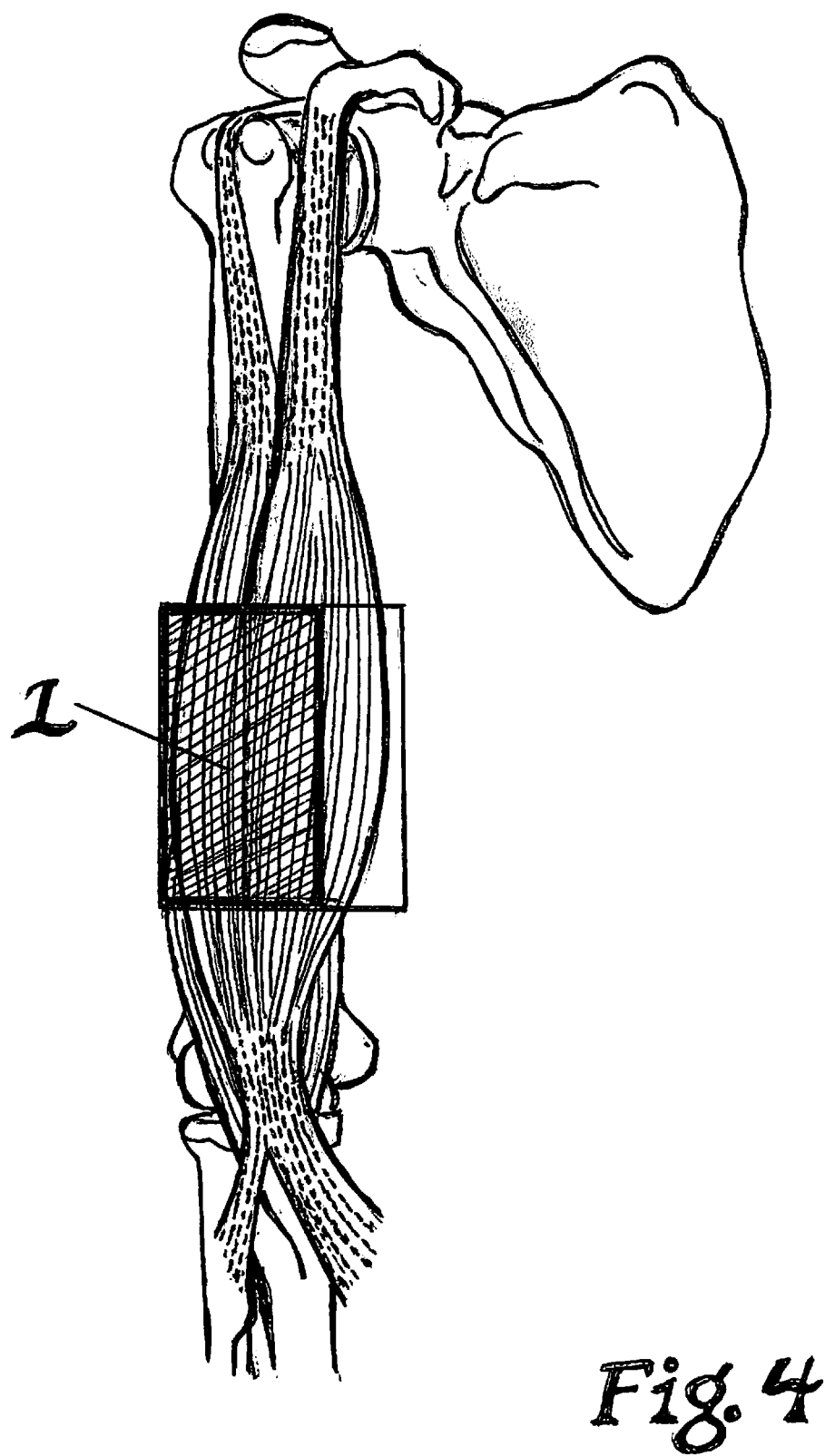

FIG. 4. is a drawing of the application of a second layer of the adhesive medical tape applied to the biceps brachii for the inhibition taping method. This layer of tape is specifically applied over the first layer of the first piece of tape applied.

Figure 5:
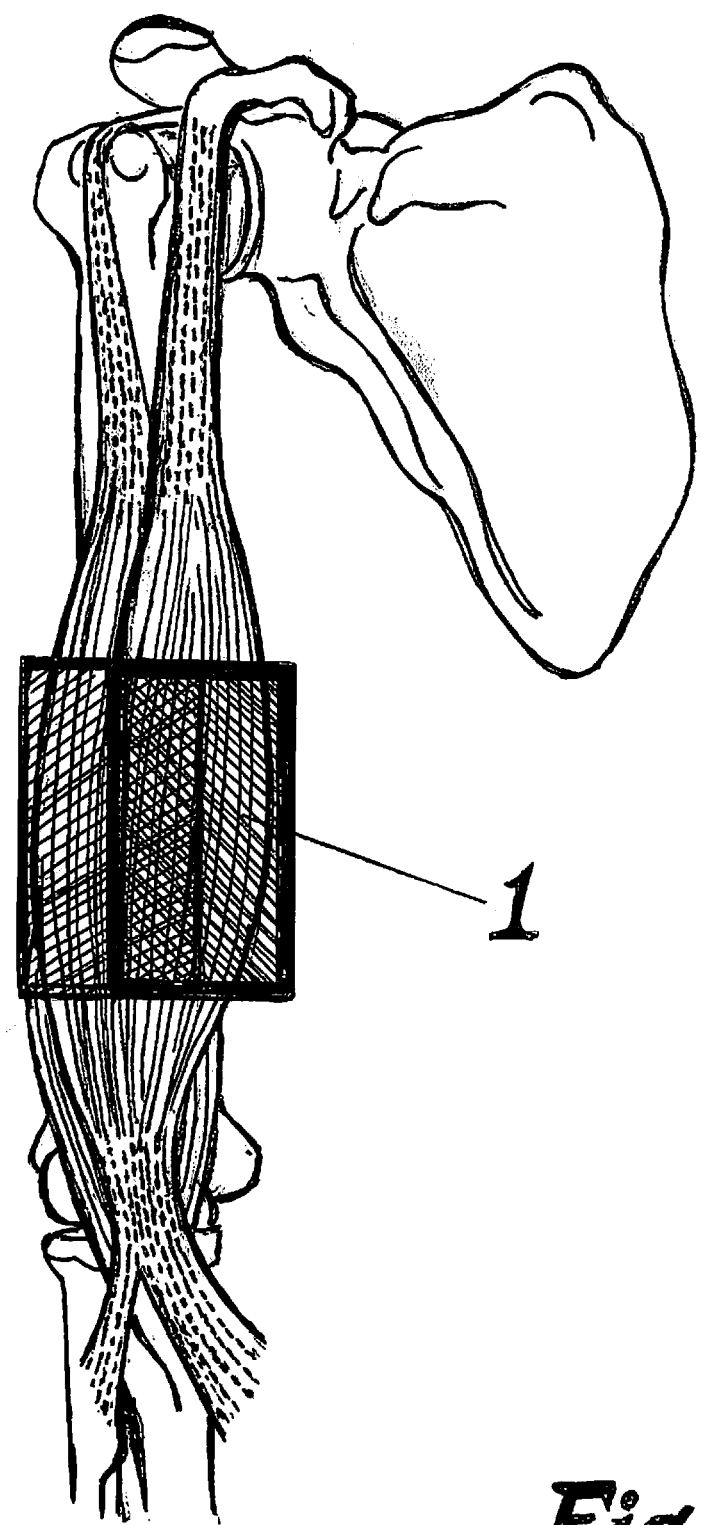

FIG. 5. is a drawing of the application of a second layer of the adhesive medical tape applied to the biceps brachii for the inhibition taping method. This layer of tape is specifically applied over the first layer of the second piece of tape applied.

Figure 6:
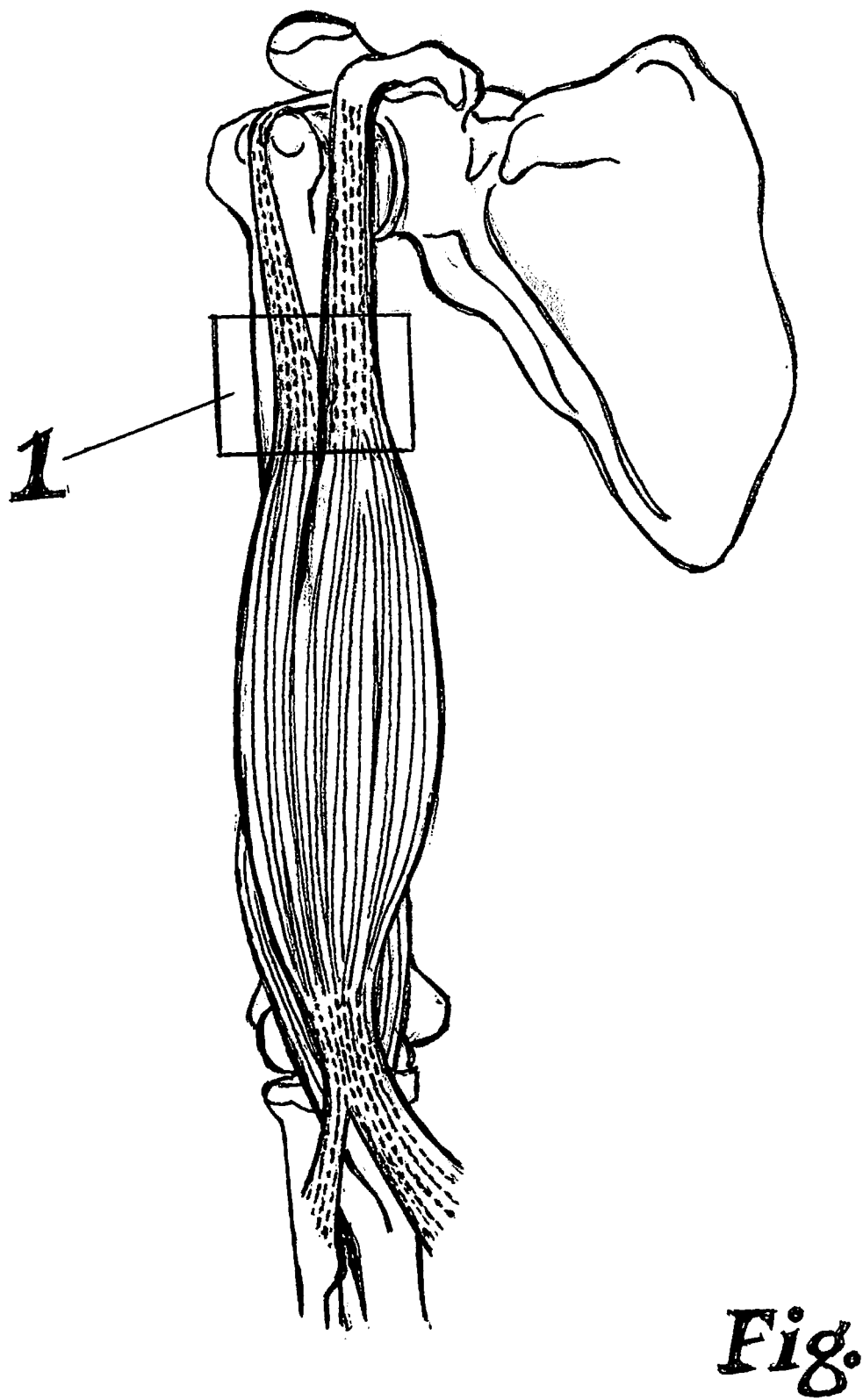

FIG. 6. is a drawing of the application of adhesive medical tape applied to the biceps brachii for the elicitation taping method. The tape is applied in series to the Golgi tendon organs in the myotendinous junction. There is one layer of the tape that is specifically applied to the proximal myotendinous junction of the biceps brachii muscle.

Figure 7:
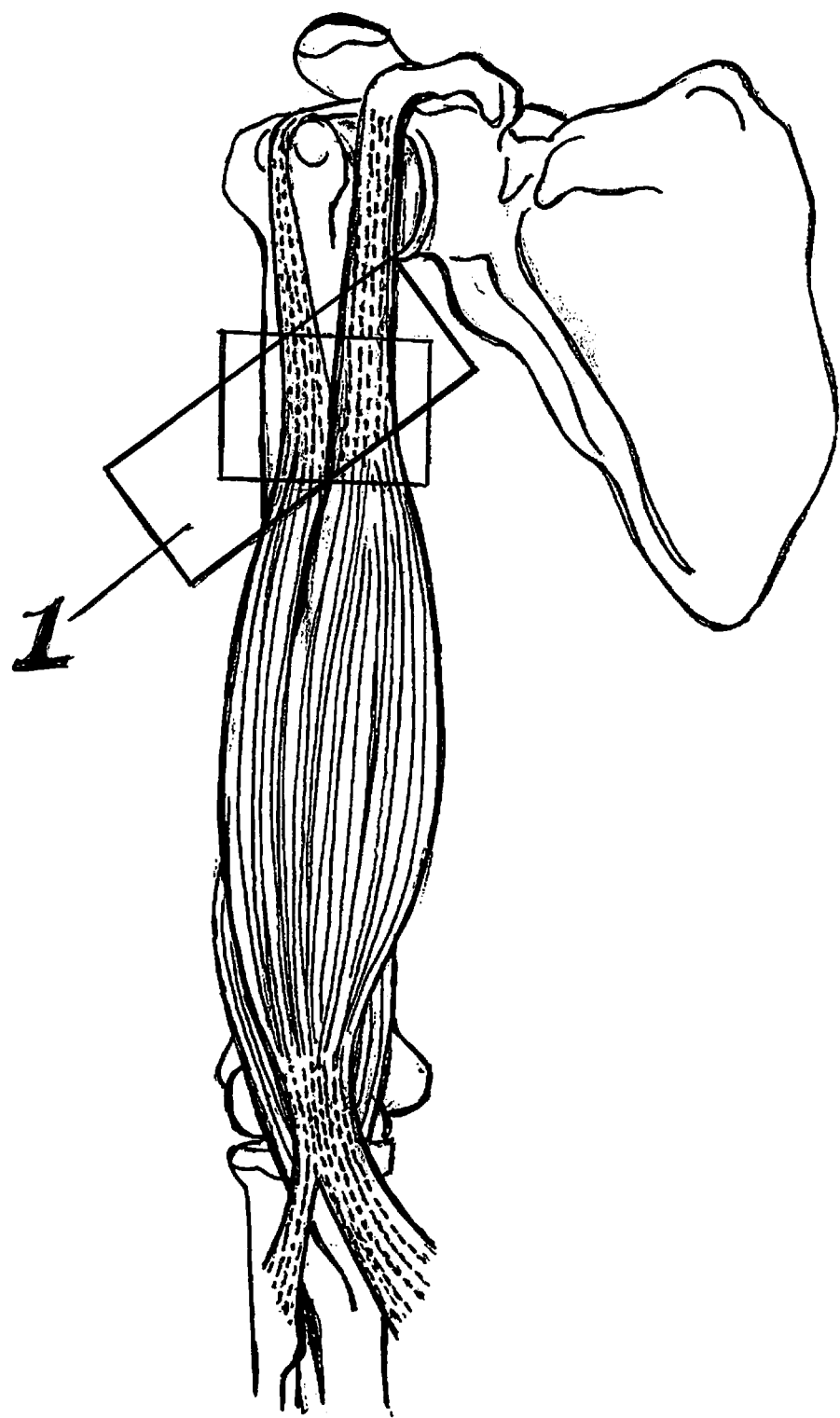

FIG. 7. is a drawing of the application of adhesive medical tape applied to the biceps brachii for the elicitation taping method. The tape is laterally placed along the muscle in the proximal region of the muscle, overlapping the first piece of tape at an angle. It is placed at an angle that will complete a 90-degree angle with the other tape.

Figure 8:
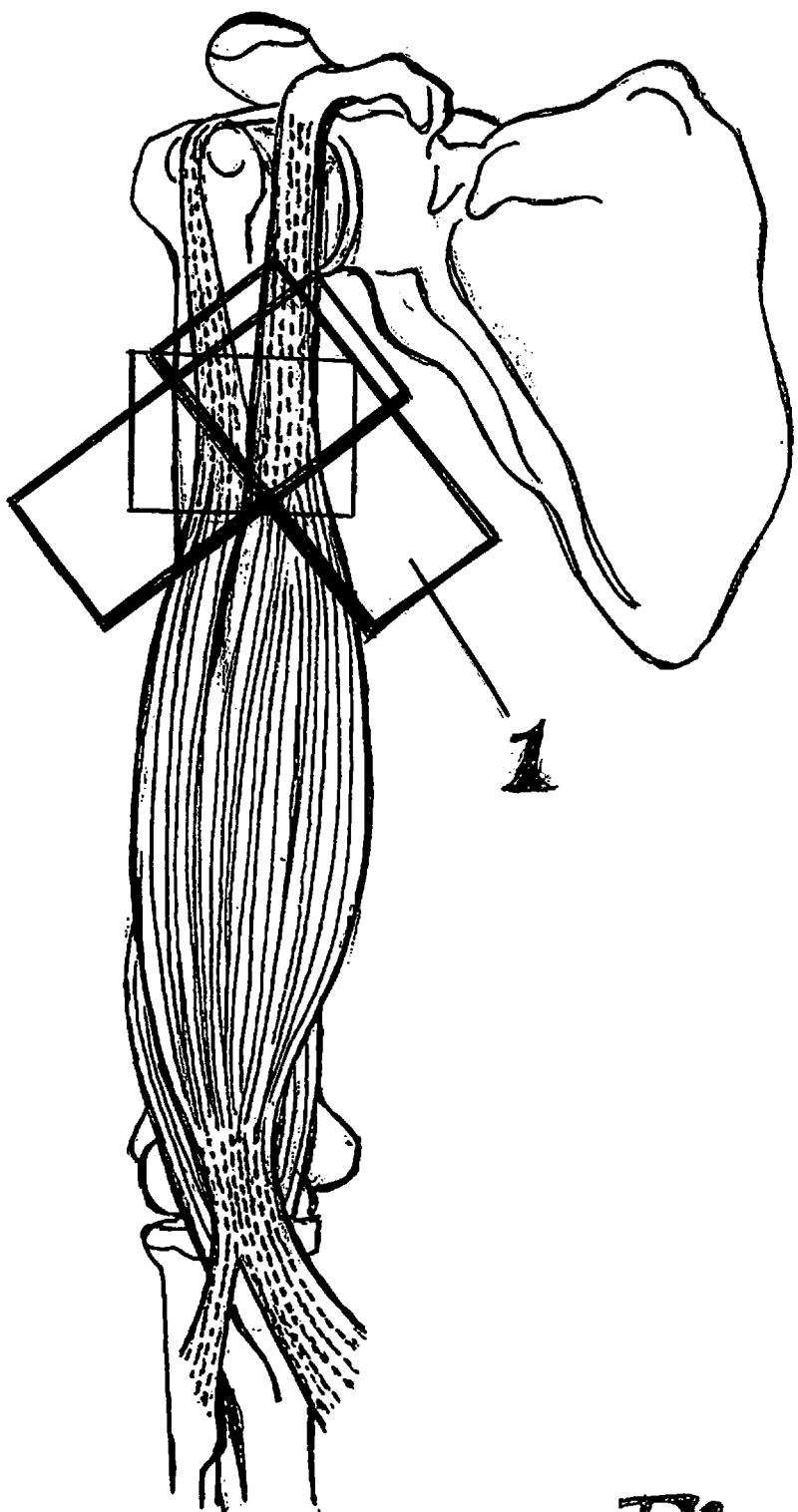

FIG. 8. is a drawing of the application of adhesive medical tape applied to the biceps brachii for the elicitation taping method. The tape is medially placed along the muscle in the proximal region of the muscle, overlapping the first piece of tape at an angle. Note the tape now completes a 90-degree angle.

Figure 9:
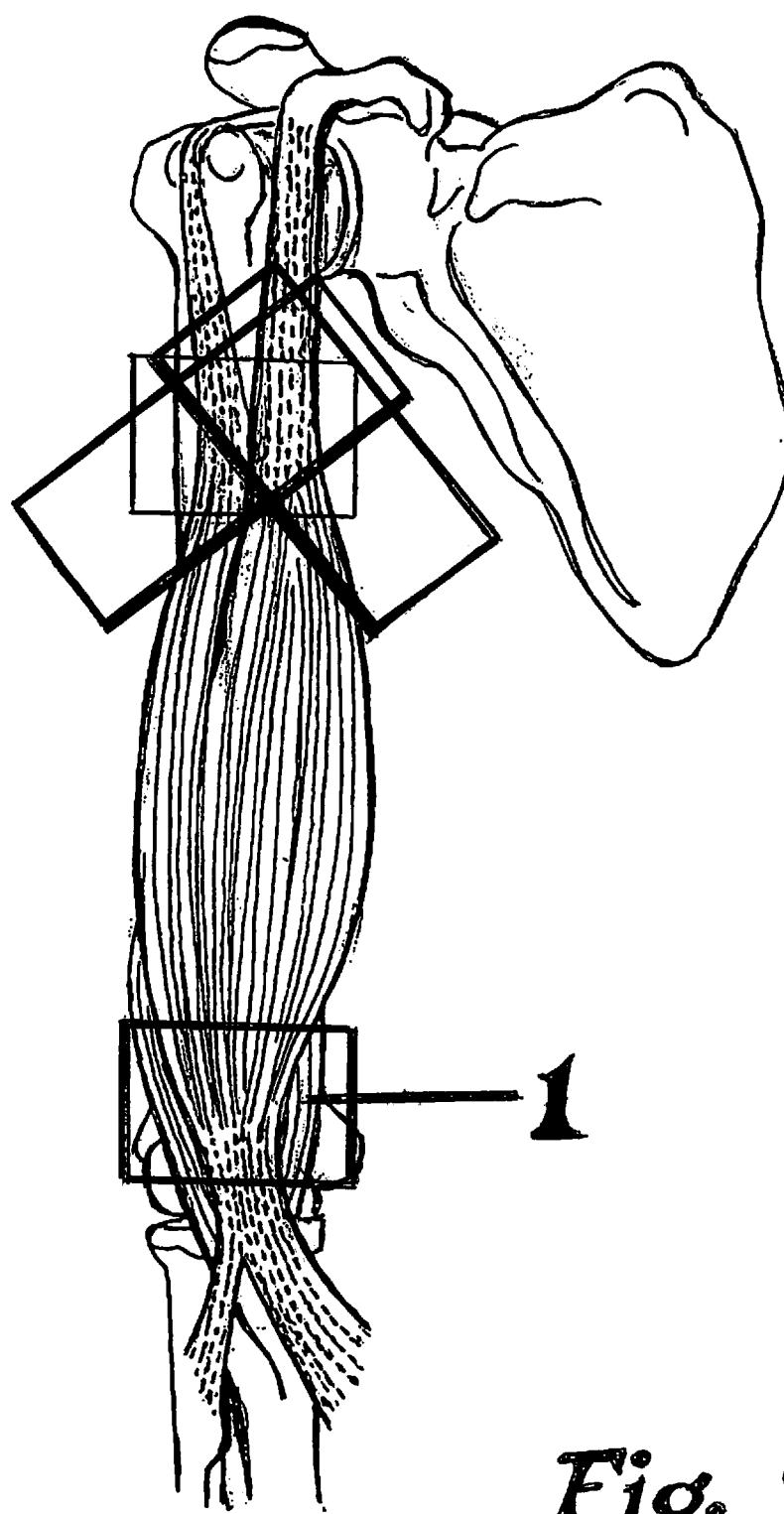

FIG. 9. is a drawing of the application of adhesive medical tape applied to the biceps brachii for the elicitation taping method. The tape is applied in series to the Golgi tendon organs in the myotendinous junction. There is one layer of tape that is specifically applied to the distal myotendinous junction of the biceps brachii muscle.

Figure 10:
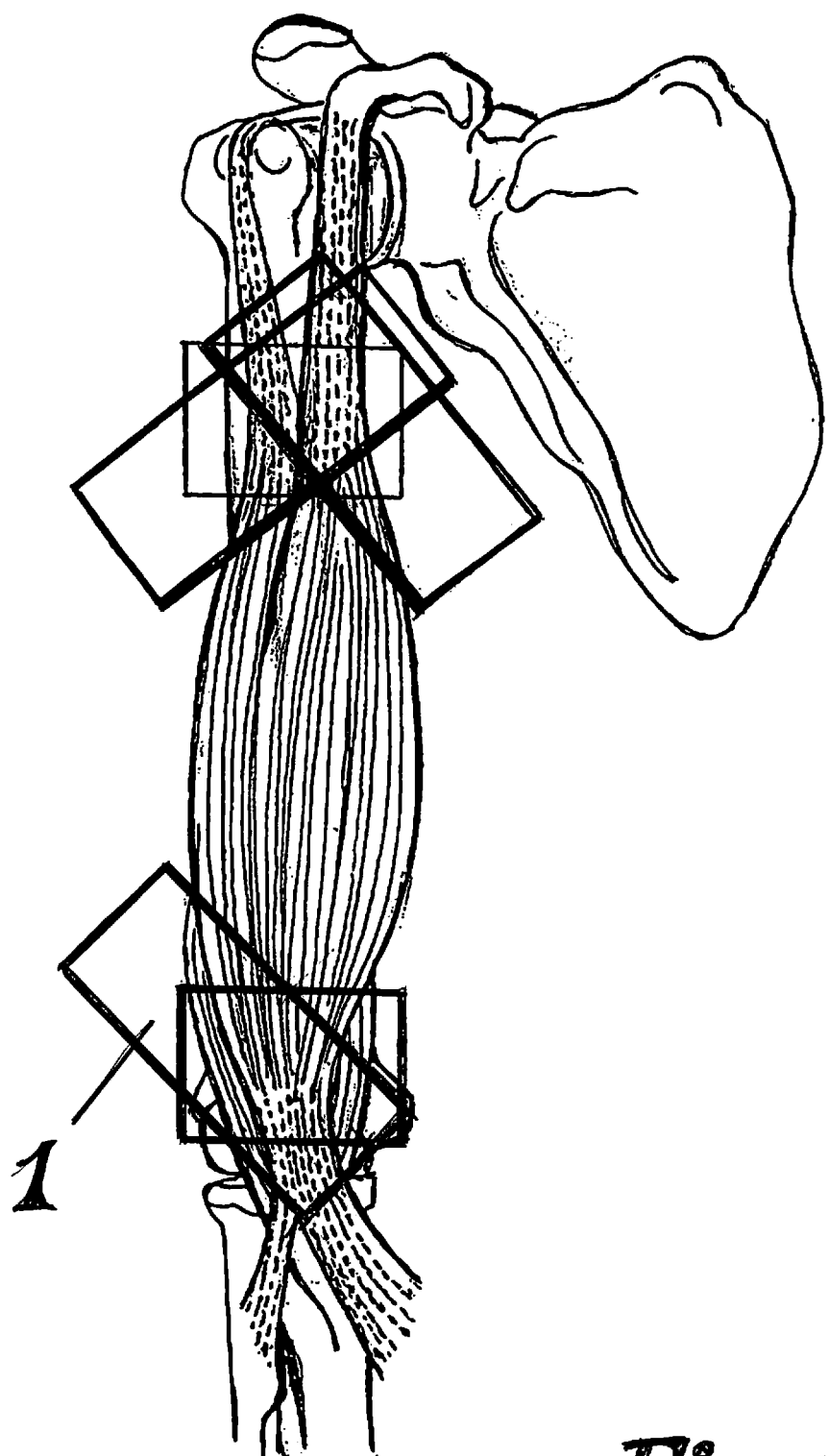

FIG. 10. is a drawing of the application of adhesive medical tape applied to the biceps brachii for the elicitation taping method. The tape is laterally placed along the muscle on the distal region of the muscle, overlapping the second piece of tape placed. It is placed at an angle that will complete a 90-degree angle with the other tape.

Figure 11:
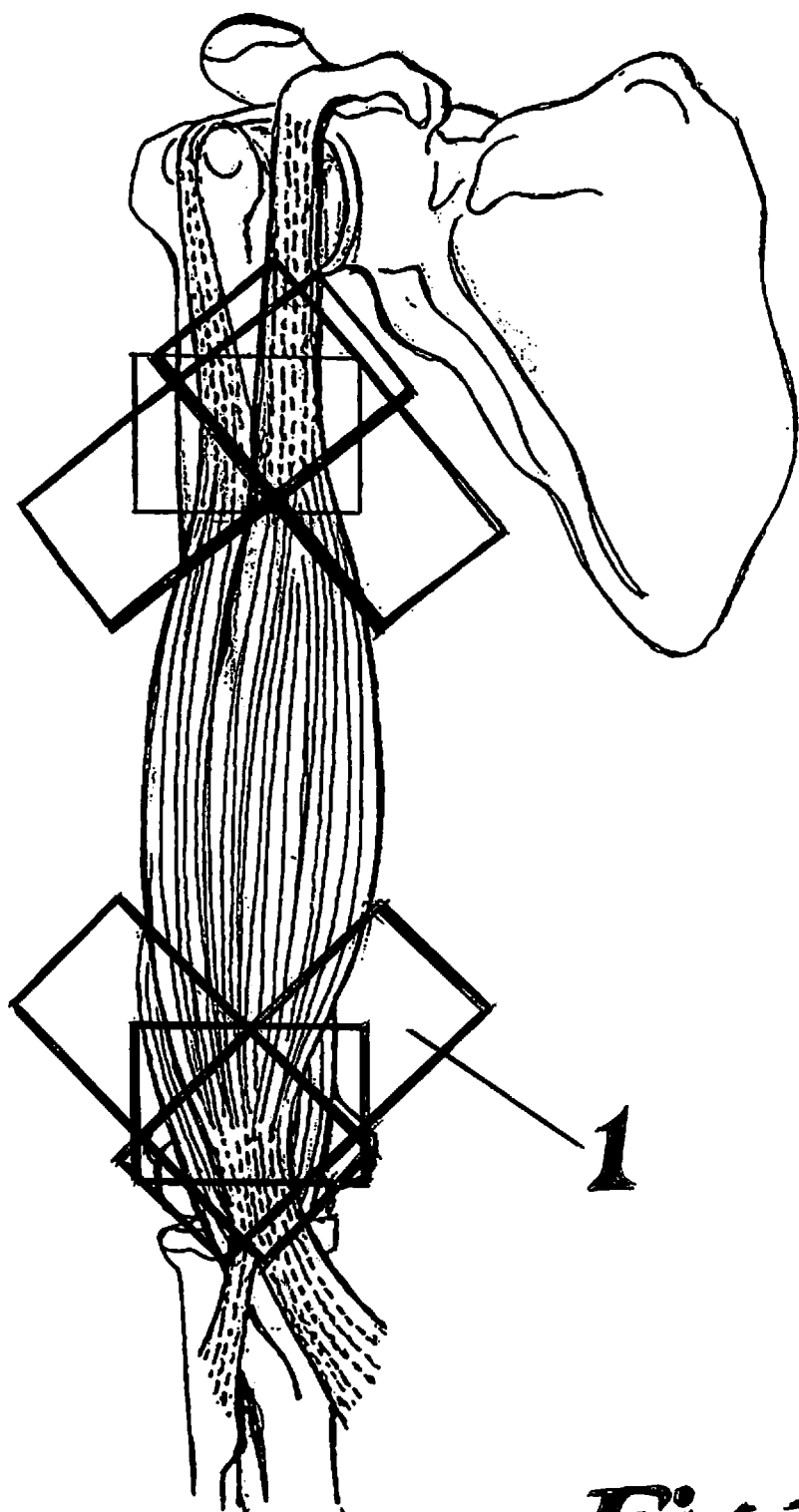

FIG. 11. is a drawing of the application of adhesive medical tape applied to the biceps brachii for the elicitation taping method. The tape is medially placed along the muscle in the distal region of the muscle; overlapping the second piece of tape placed. Noted the tape now completes a 90-degree angle.

Figure 12:
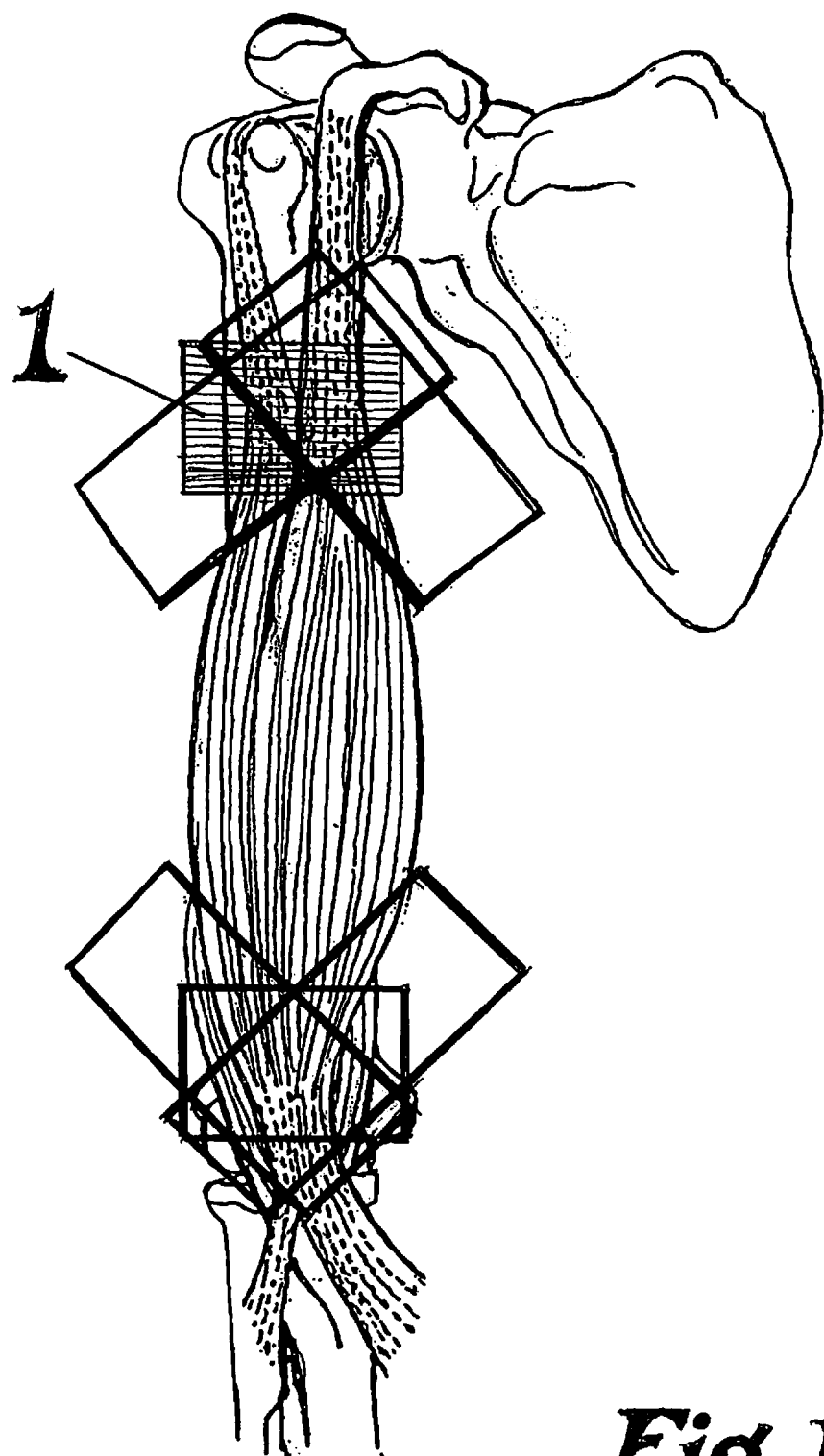

FIG. 12. is a drawing of the application of a second layer of the adhesive medical tape applied to the biceps brachii for the elicitation taping method. This layer of tape is specifically applied over the first layer of the first piece of tape centrally applied.

Figure 13:
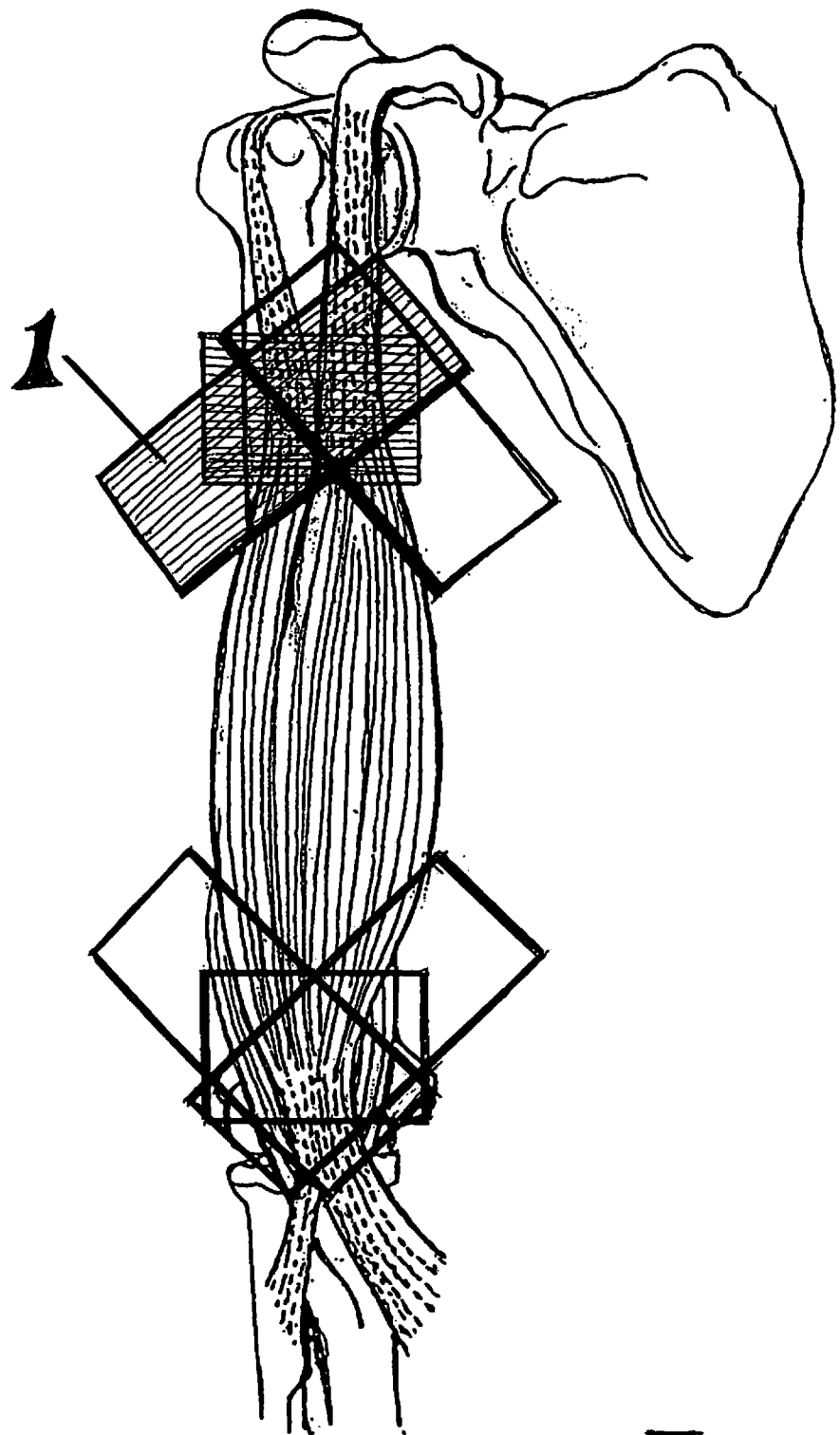

FIG. 13. is a drawing of the application of another of a second layer of the adhesive medical tape applied to the biceps brachii for the elicitation taping method. This layer of tape is specifically applied over the first layer of the second piece of tape laterally applied.

Figure 14:
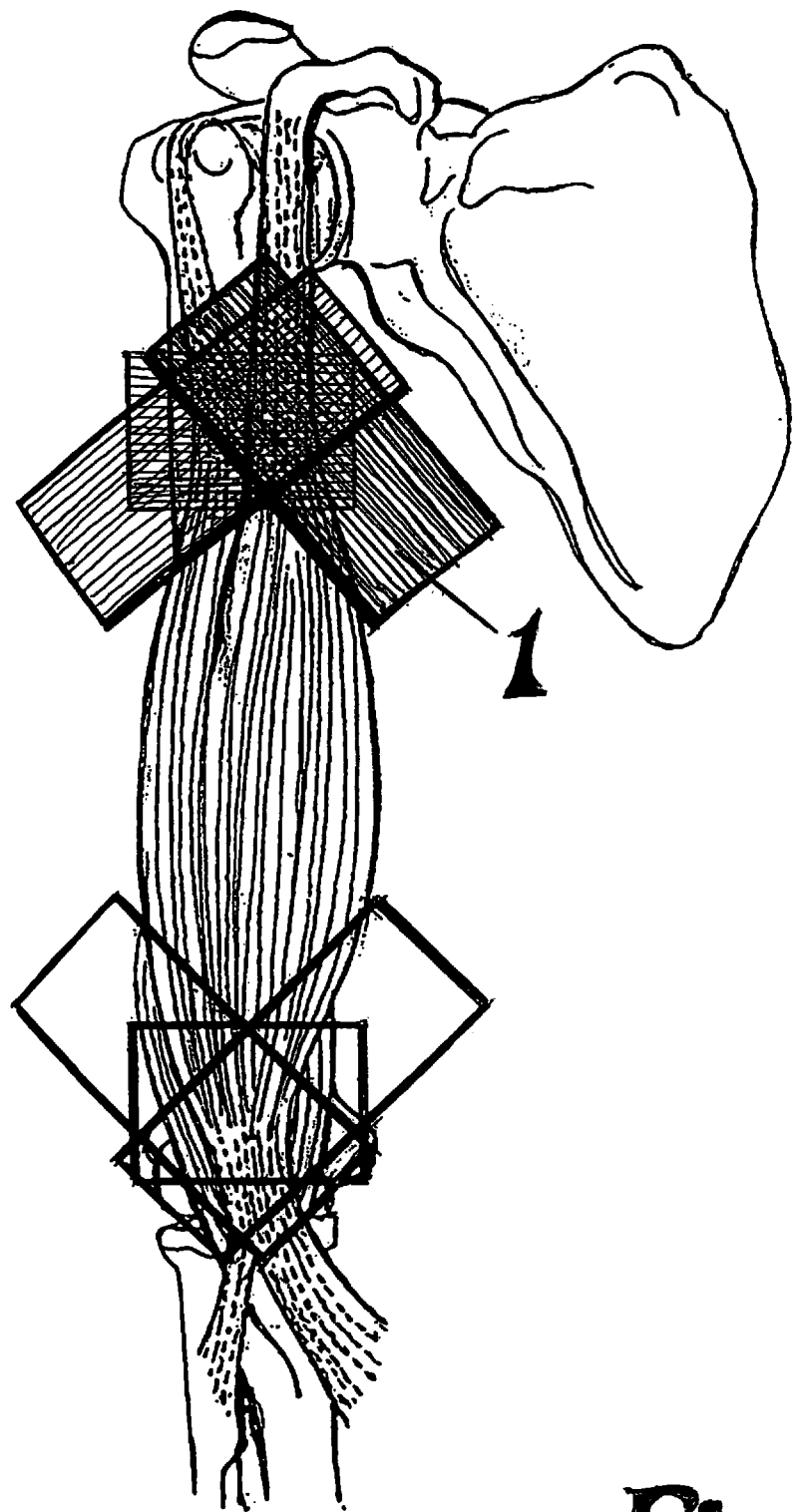

FIG. 14. is a drawing of the application of a second layer of the adhesive medical tape applied to the biceps brachii for the elicitation taping method. This layer of tape is specifically applied over the first layer of the third piece of tape medially applied.

Figure 15:
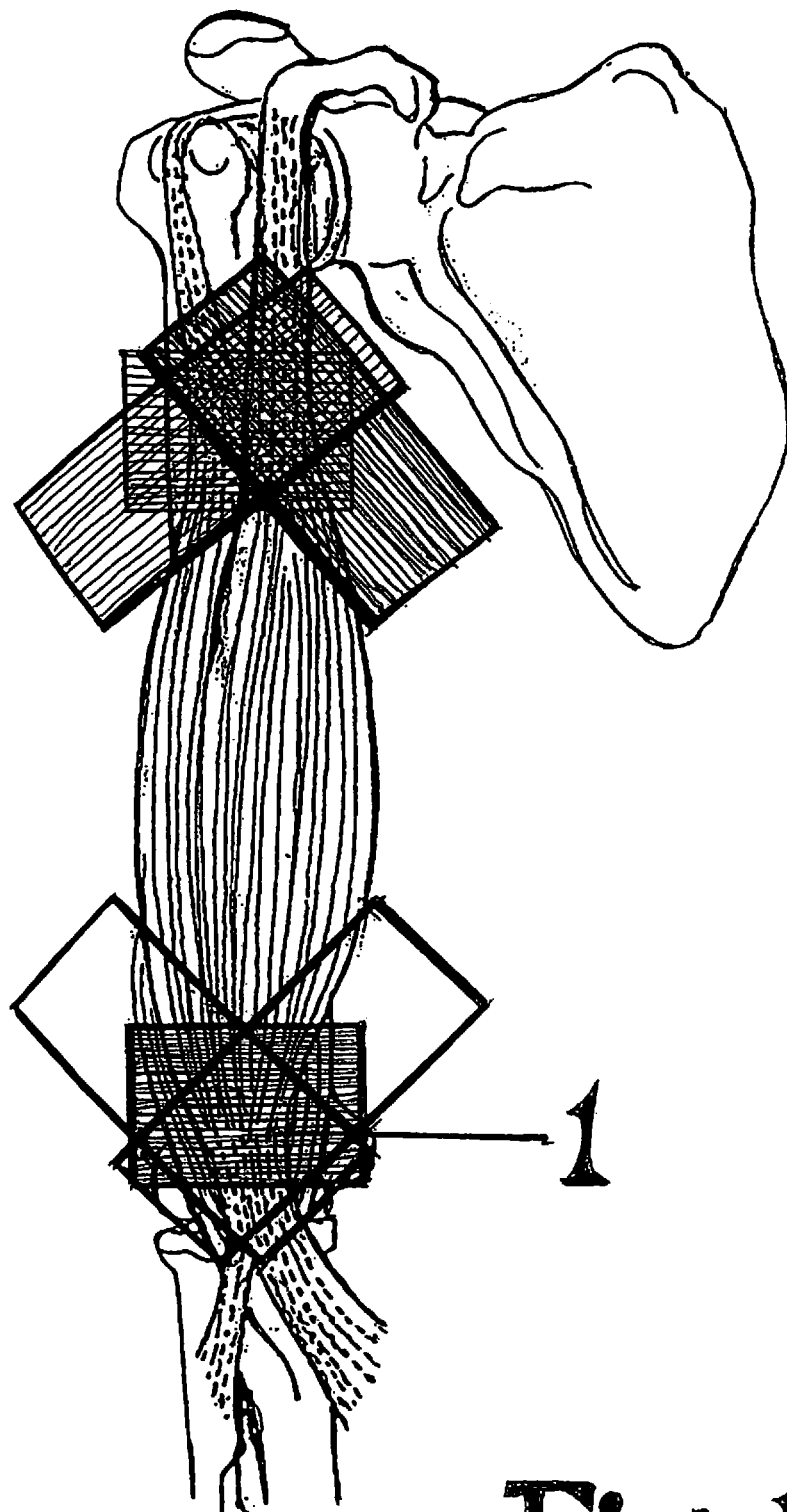

FIG. 15. is a drawing of the application of a second layer of the adhesive medical tape applied to the biceps brachii for the elicitation taping method. This layer of tape is specifically applied over the first layer of the fourth piece of tape centrally applied.

Figure 16:
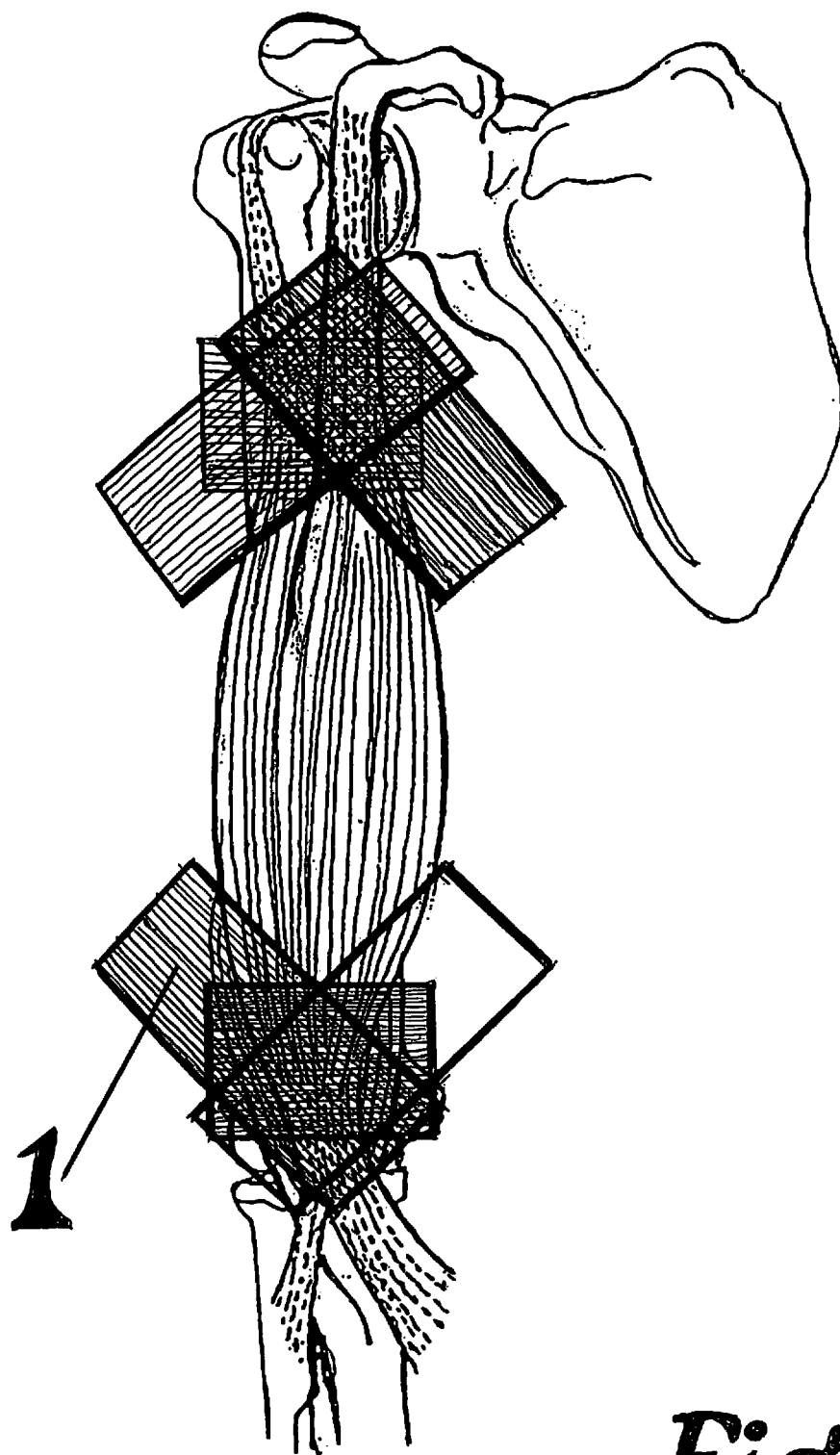

FIG. 16. is a drawing of the application of a second layer of the adhesive medical tape applied to the biceps brachii for the elicitation taping method. This layer of tape is specifically applied over the first layer of the fifth piece of tape laterally applied.

Figure 17:
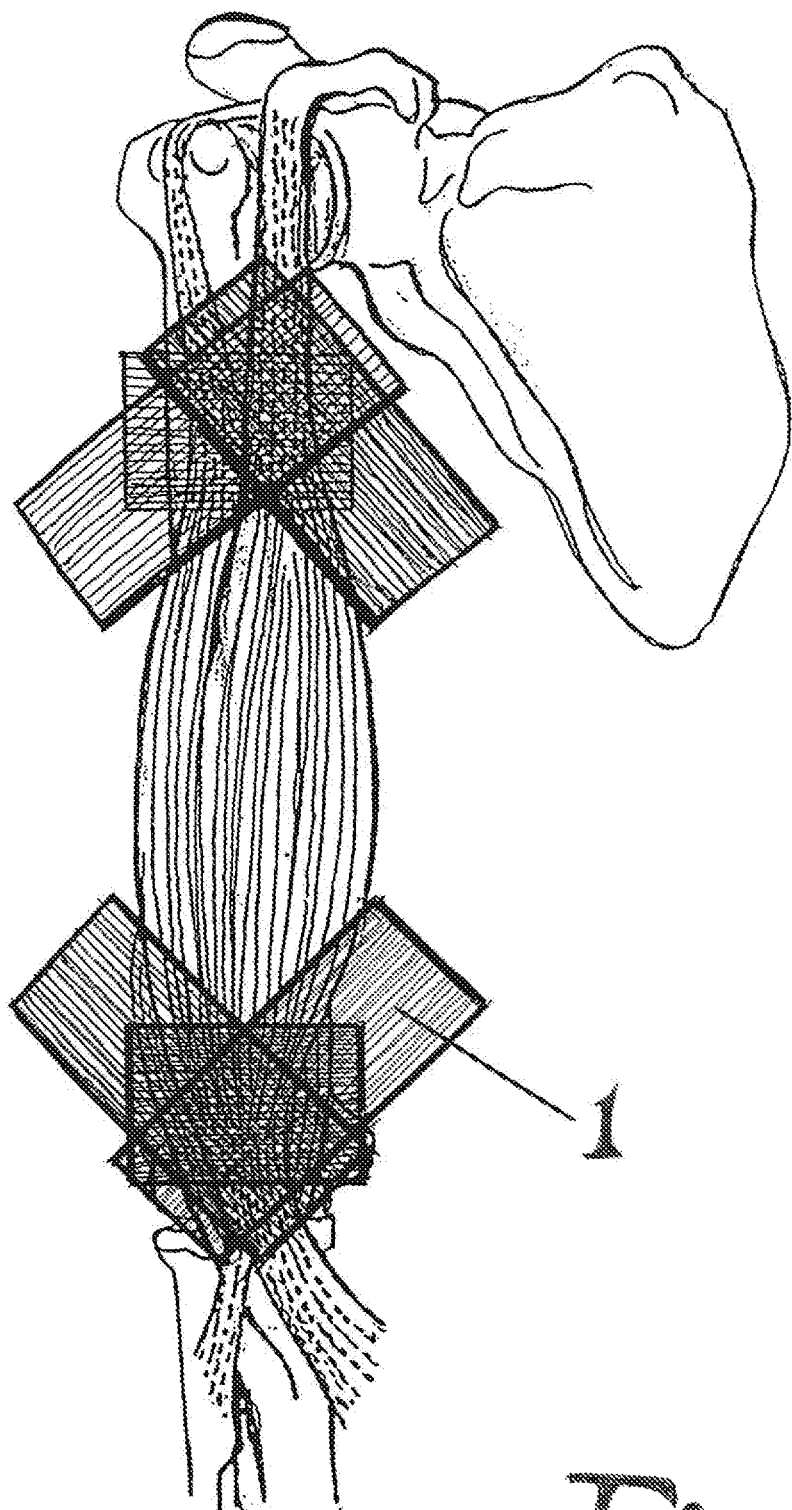

FIG. 17. is a drawing of the application of a second layer of the adhesive medical tape applied to the biceps brachii for the elicitation taping method. This layer of tape is specifically applied over the first layer of the sixth piece of tape medially applied.

Figure 18:
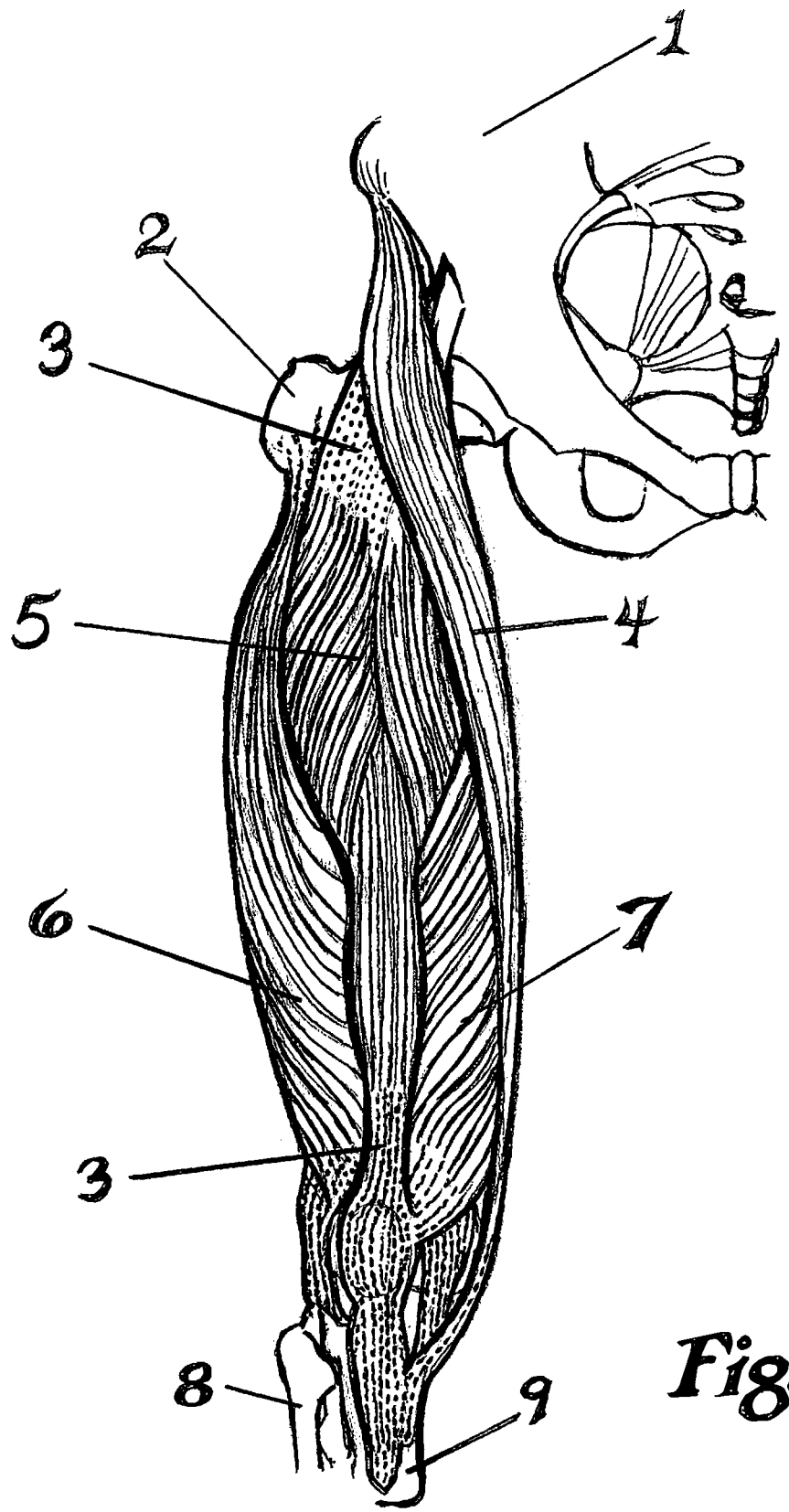

FIG. 18. is a drawing of the right lower extremity quadriceps femoris muscle group. 1. pelvis; 2. greater trochanter; 3. myotendinous junction; 4. sartorius; 5. rectus femoris; 6. a muscle fiber (extrafusal fiber); 7. vastus lateralis; 8. vastus medialis; 9. patella; 10. proximal fibula; 11. proximal tibia.

Figure 19:
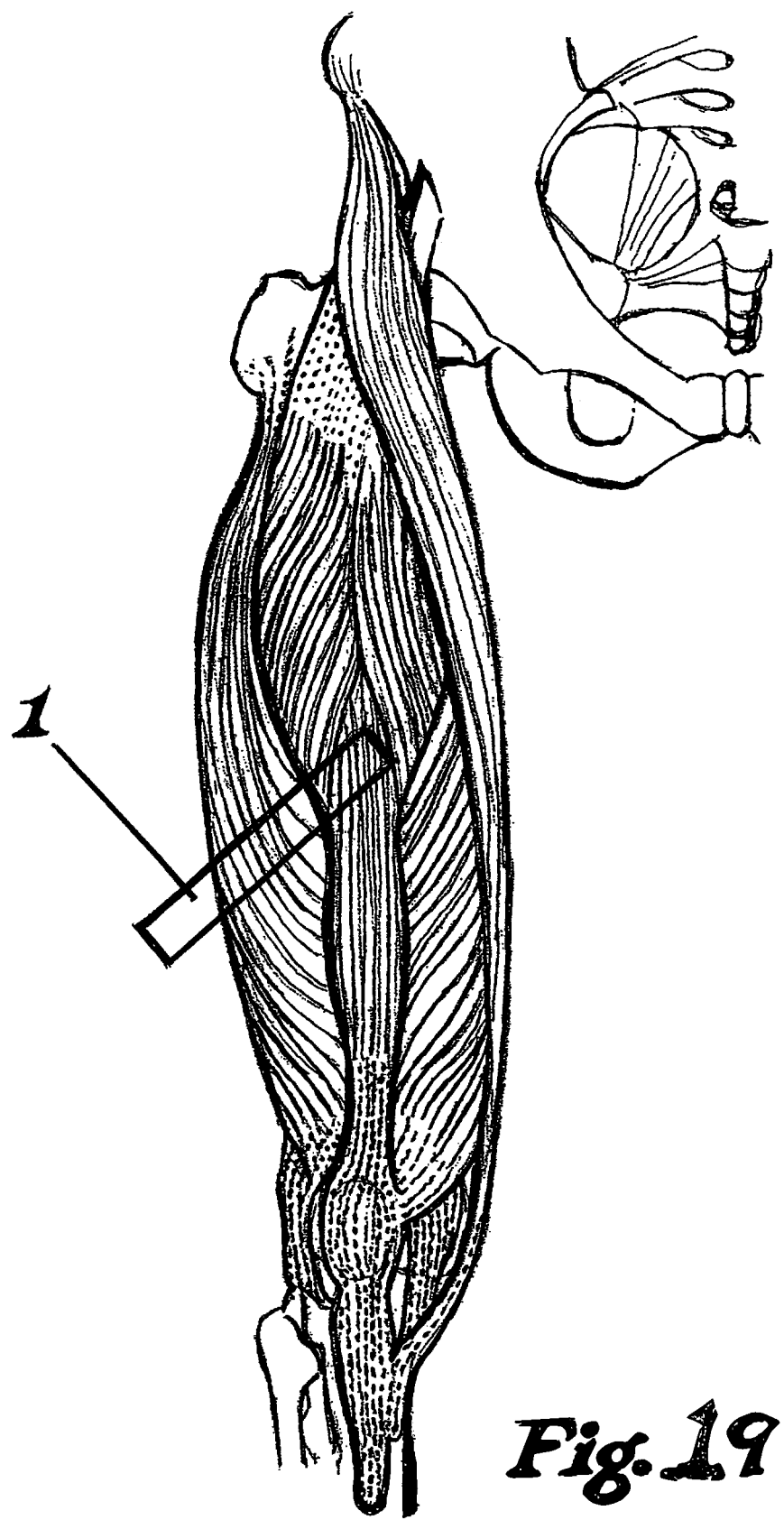

FIG. 19. is a drawing of the application of adhesive medical tape applied to the quadriceps femoris large muscle group for the elicitation taping method of creating a new origin. The tape is applied to make a new origin secondarily to the large size of the large muscle group. The new origin tape is applied at approximately 50% of the muscle group. It is placed at an angle to go along the muscle belly. The first piece of tape is applied laterally from the rectus femoris to the vastus lateralis.

Figure 20:
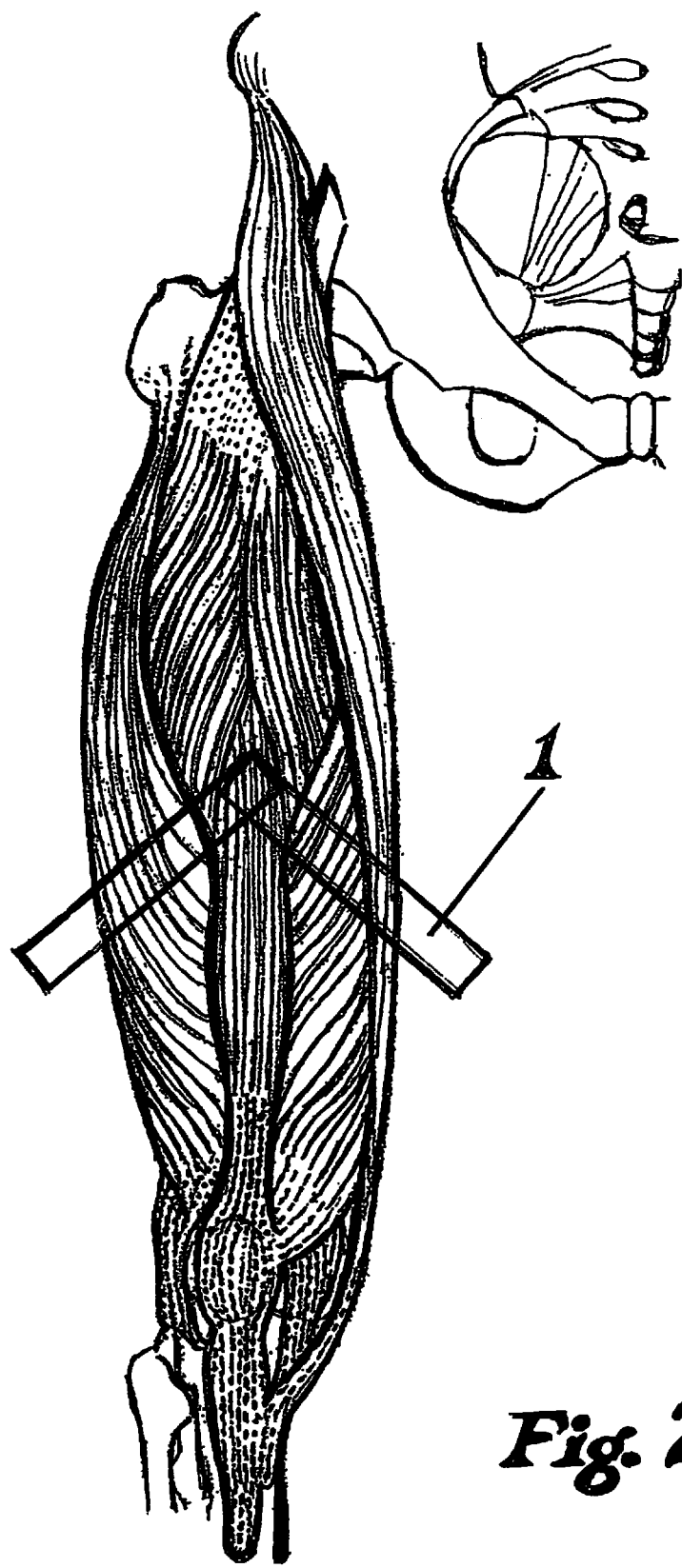

FIG. 20. is a drawing of the application of adhesive medical tape applied to the quadriceps femoris large muscle group for the elicitation taping method. The tape is applied to make a new origin secondarily to the large size of the large muscle group. The new origin tape is applied at approximately 50% of the muscle group. It is placed at an angle to go along the muscle belly. The second piece of tape is applied medially from the rectus femoris to the vastus medialis.

Figure 21:
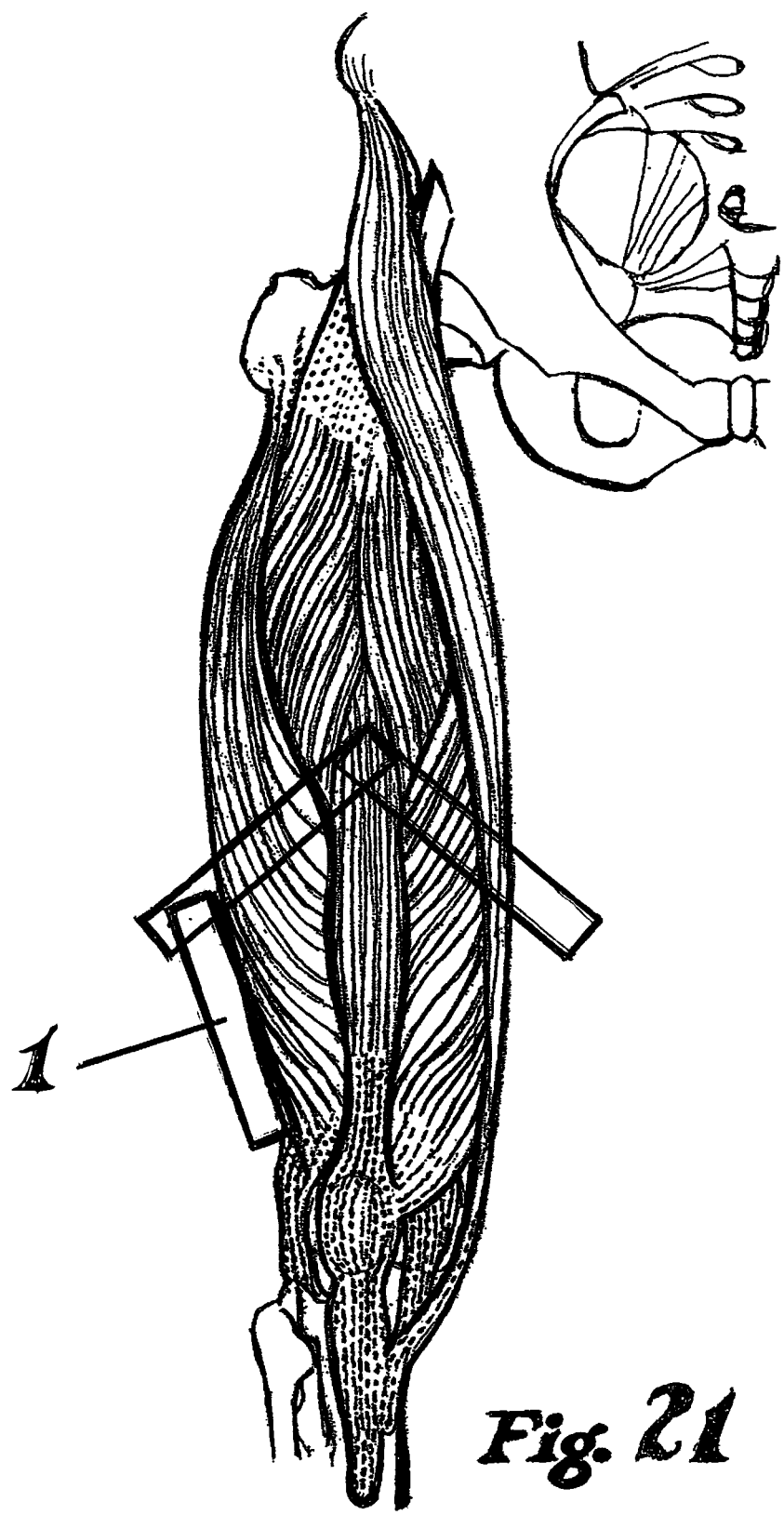

FIG. 21. is a drawing of the application of adhesive medical tape applied to the quadriceps femoris large muscle group for the elicitation taping method. The tape is placed laterally along the muscle of the vastus lateralis to the end of the muscle. The muscle must be outlined for the elicitation.

Figure 22:
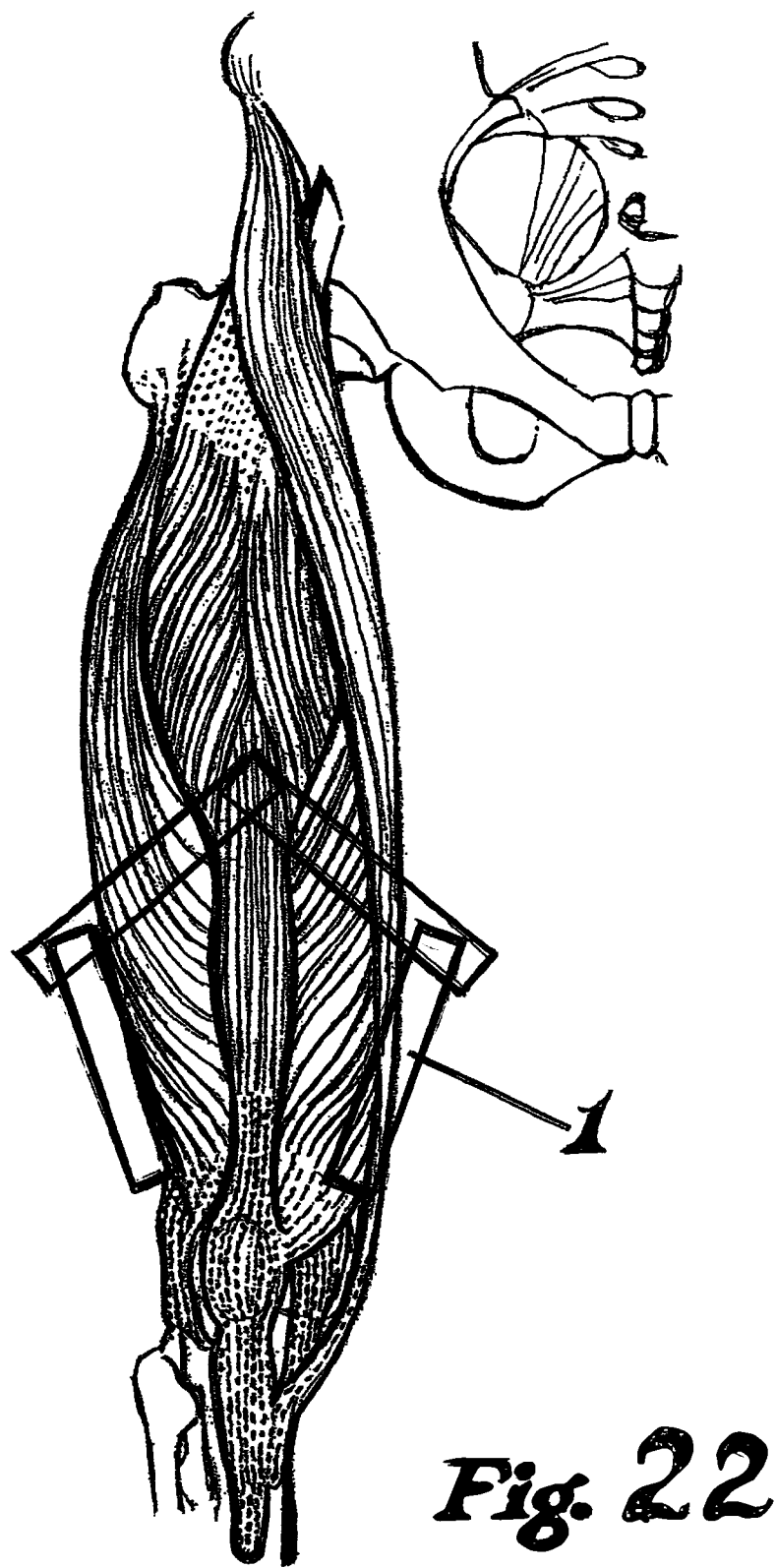

FIG. 22. is a drawing of the application of adhesive medical tape applied to the quadriceps femoris large muscle group for the elicitation taping method. The tape is placed medially along the muscle of the vastus medialis to the end of the muscle. Note it angles in a little more into the muscle secondarily to the sartorius muscle location. The muscle must be outlined for the elicitation.

Figure 23:
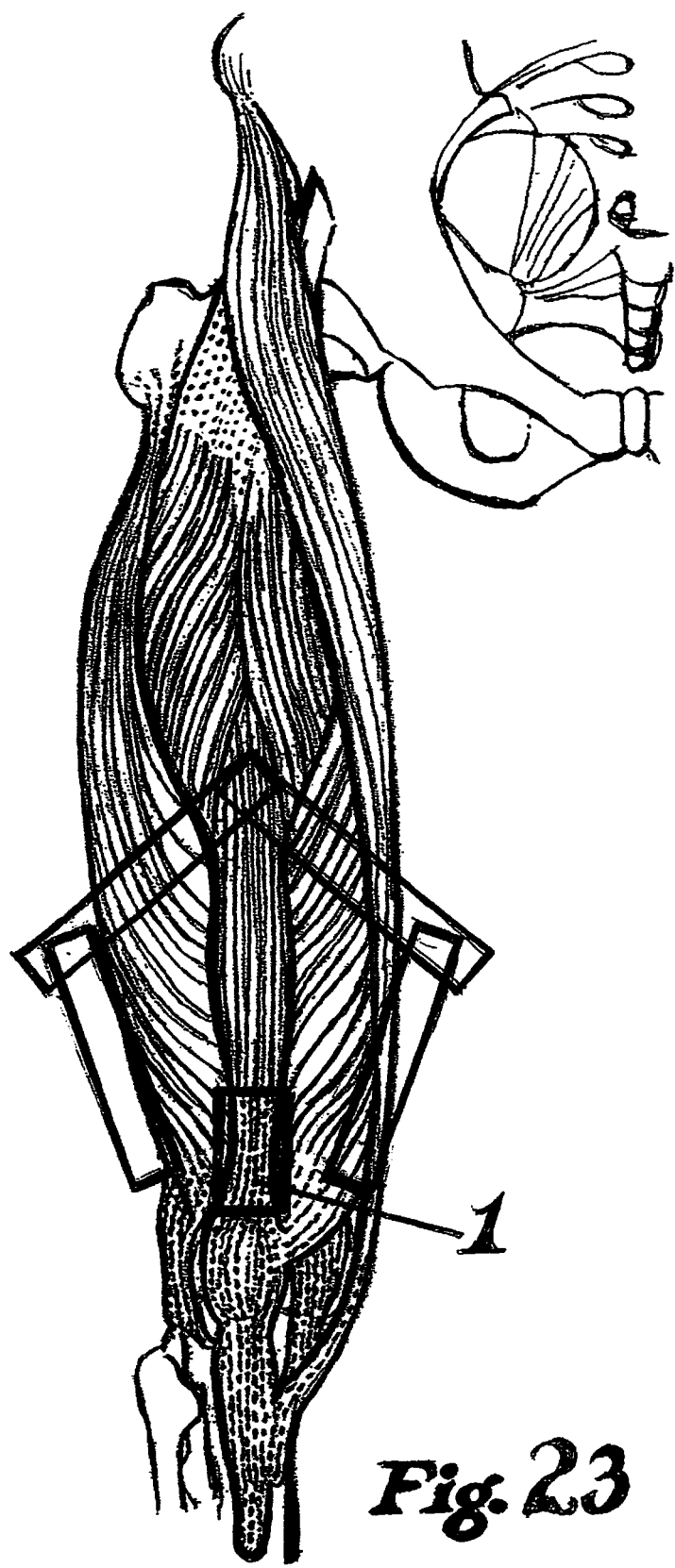

FIG. 23. is a drawing of the application of adhesive medical tape applied to the quadriceps femoris large muscle group for the elicitation taping method. The tape is placed along the muscle of the rectus femoris in series in the myotendinous region of the muscle.

Figure 24:
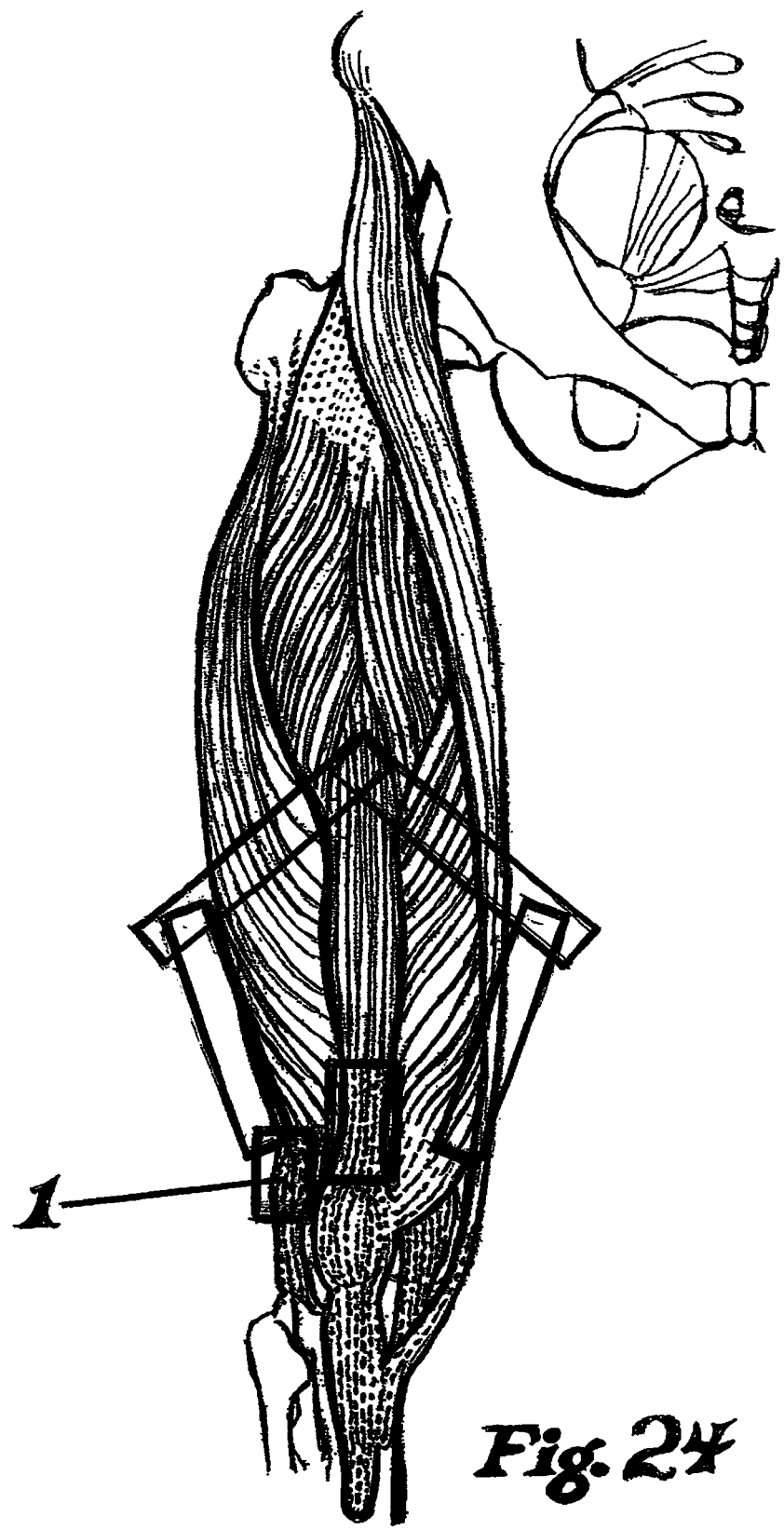

FIG. 24. is a drawing of the application of adhesive medical tape applied to the quadriceps femoris large muscle group for the elicitation taping method. The tape is laterally placed along the myotendinous region, in series and laterally to the patella.

Figure 25:
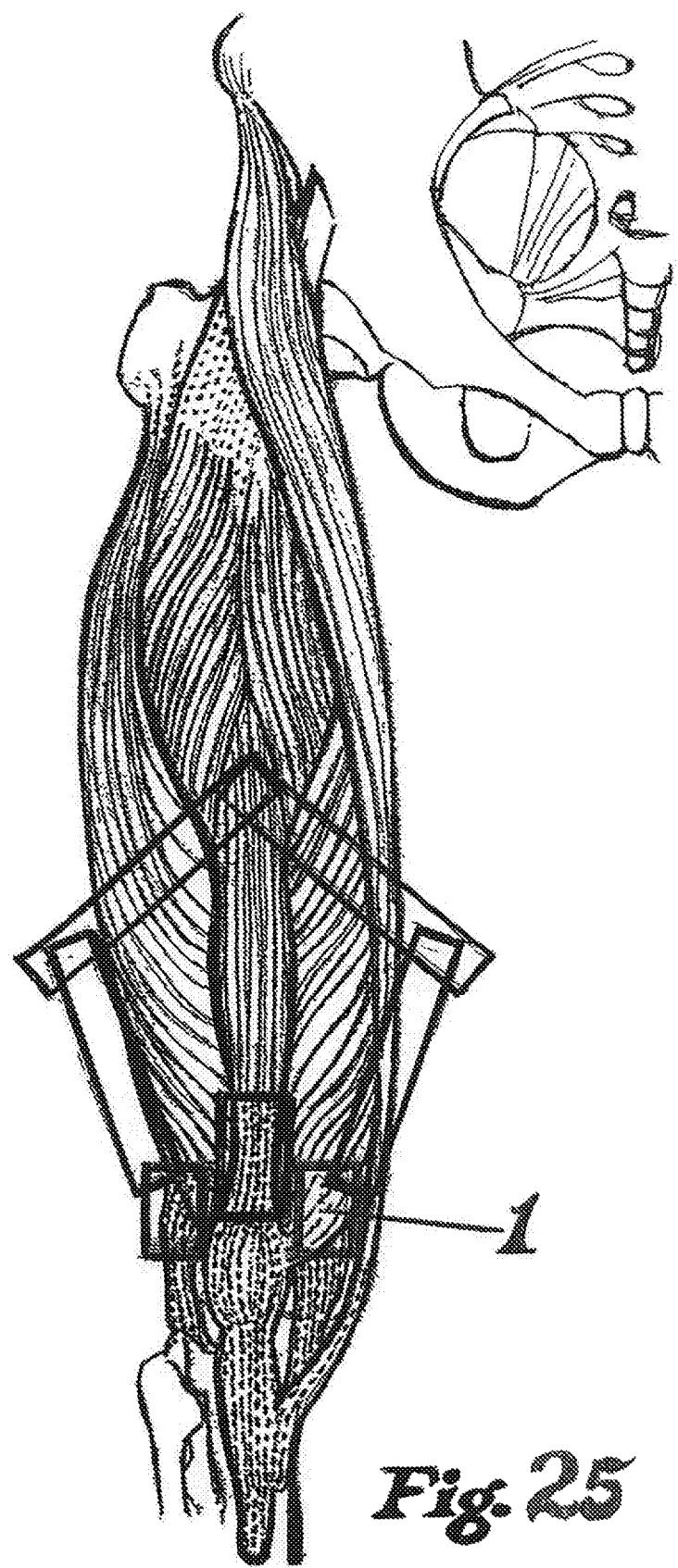

FIG. 25. is a drawing of the application of adhesive medical tape applied to the quadriceps femoris large muscle group for the elicitation taping method. The tape is placed medially along the myotendinous region, in series and medially to the patella.

Figure 26:
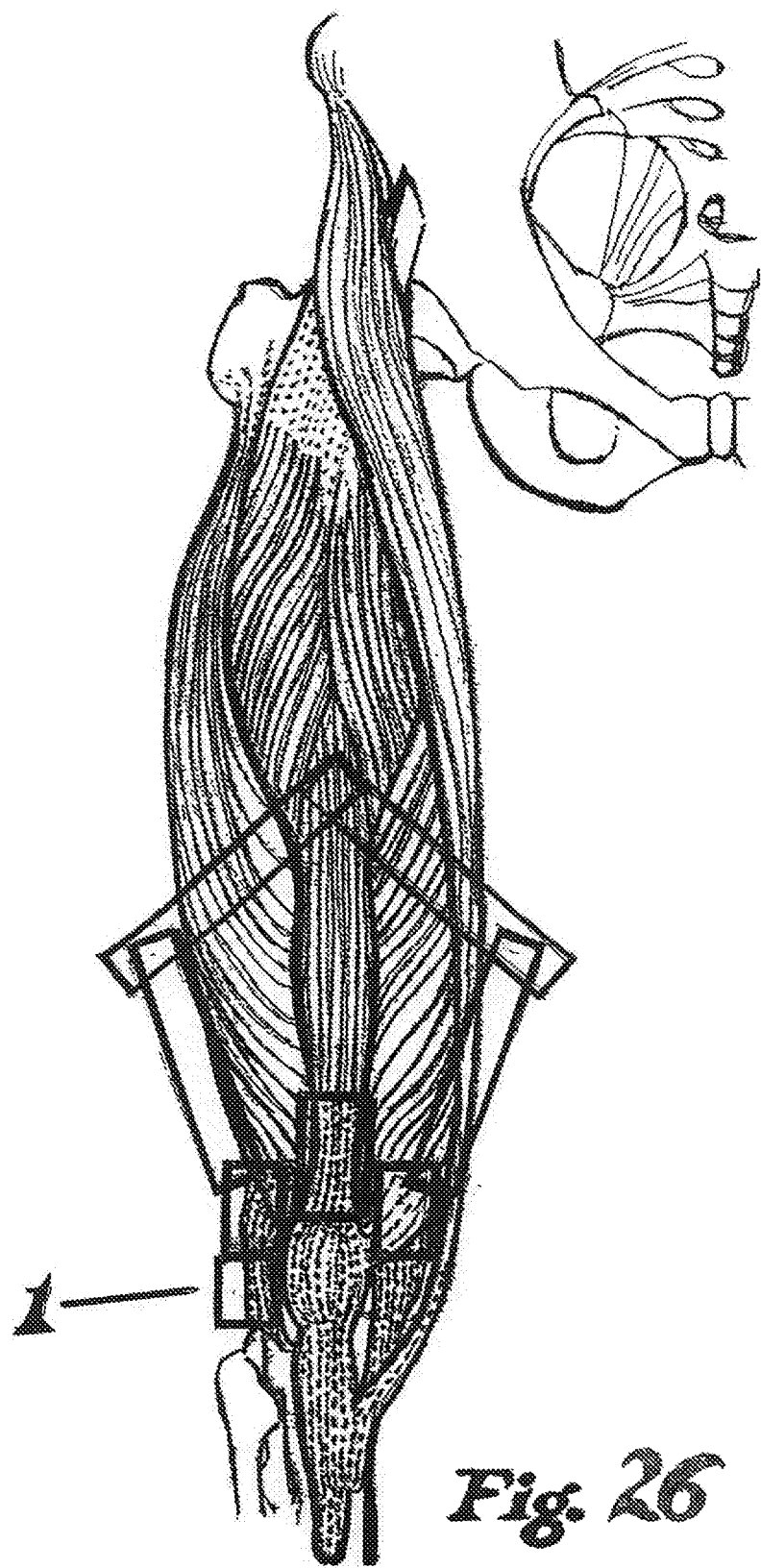

FIG. 26. is a drawing of the application of adhesive medical tape applied to the quadriceps femoris large muscle group for the elicitation taping method. The tape is placed laterally along the myotendinous region, in series and laterally to the patella.

Figure 27:
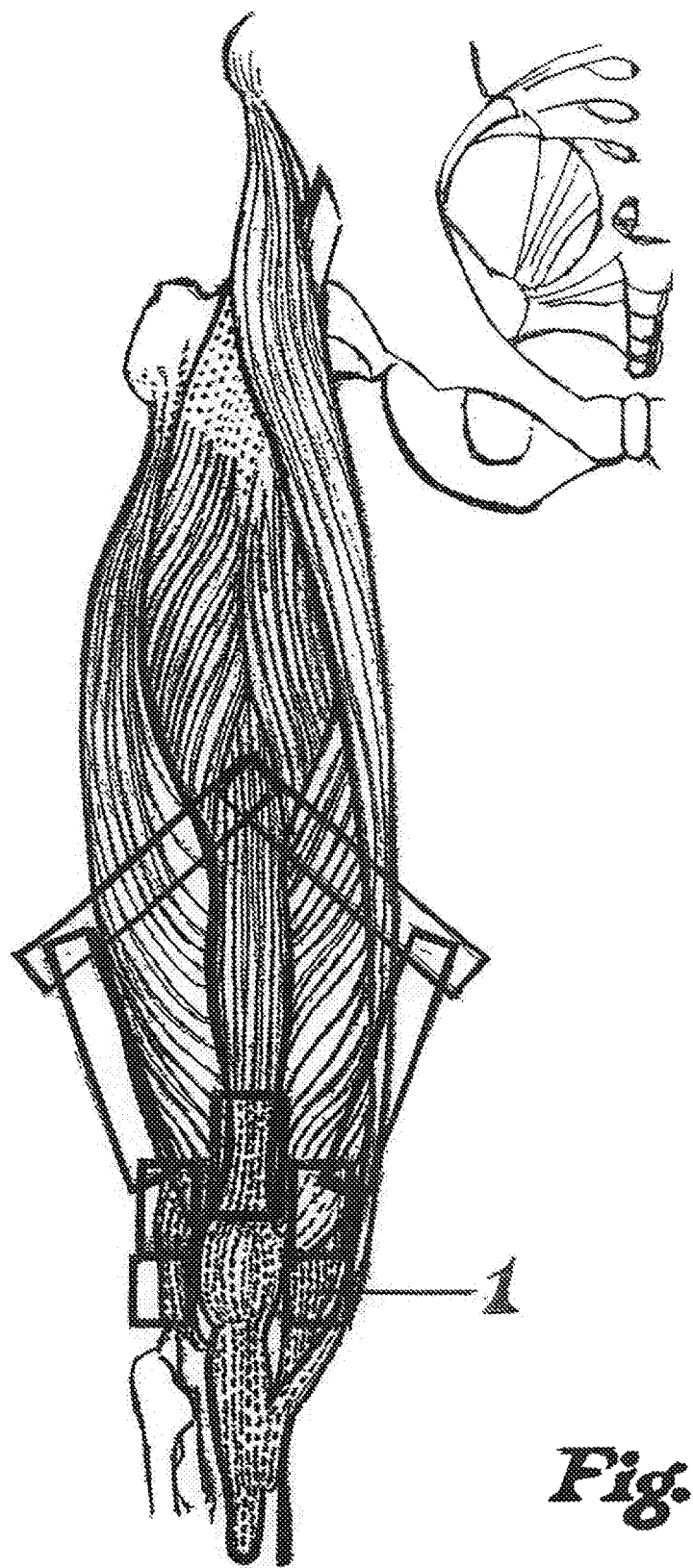

FIG. 27. is a drawing of the application of adhesive medical tape applied to the quadriceps femoris large muscle group for the elicitation taping method. The tape is placed It is placed along the myotendinous region, in series and medially to the patella.

Figure 28:
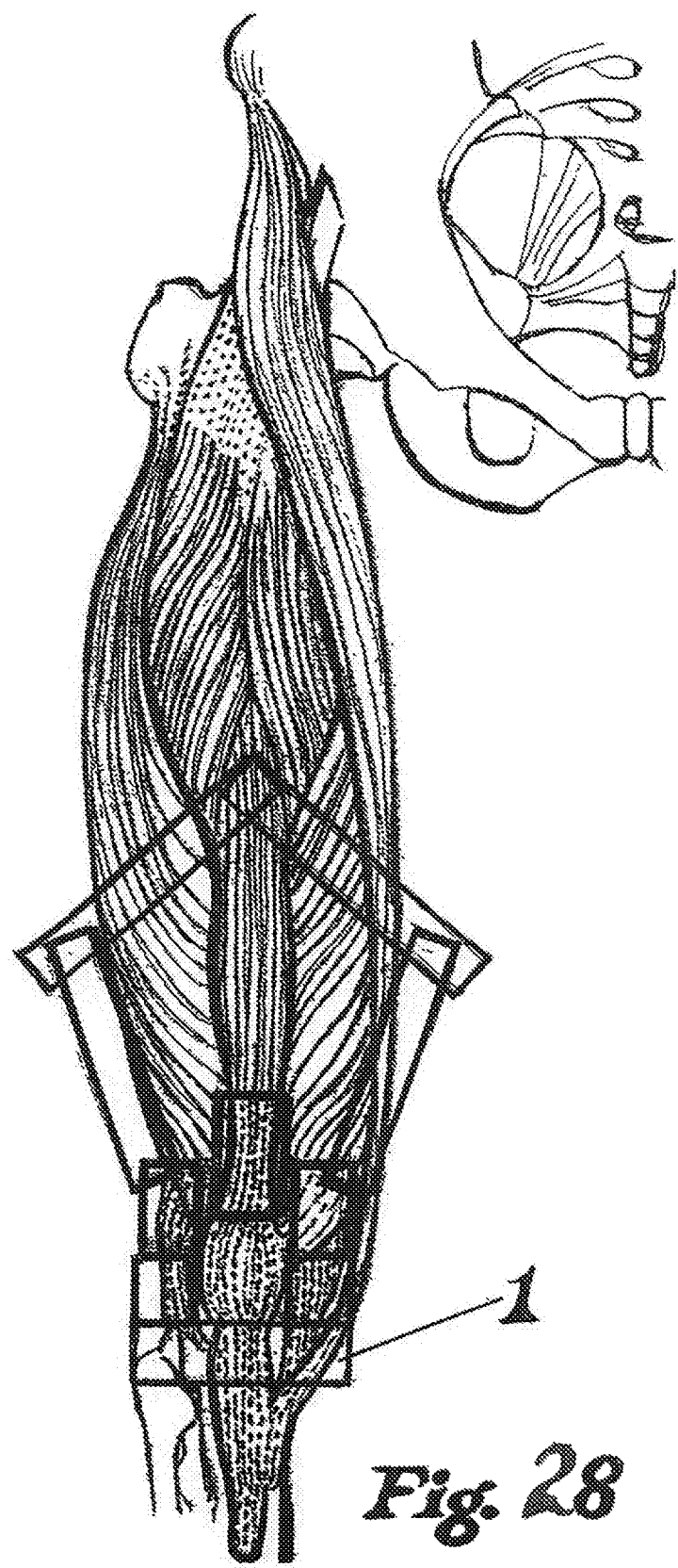

FIG. 28. is a drawing of the application of adhesive medical tape applied to the quadriceps femoris large muscle group for the elicitation taping method. The tape is placed centrally along the myotendinous region, in series and inferior to the patella.

Figure 29:
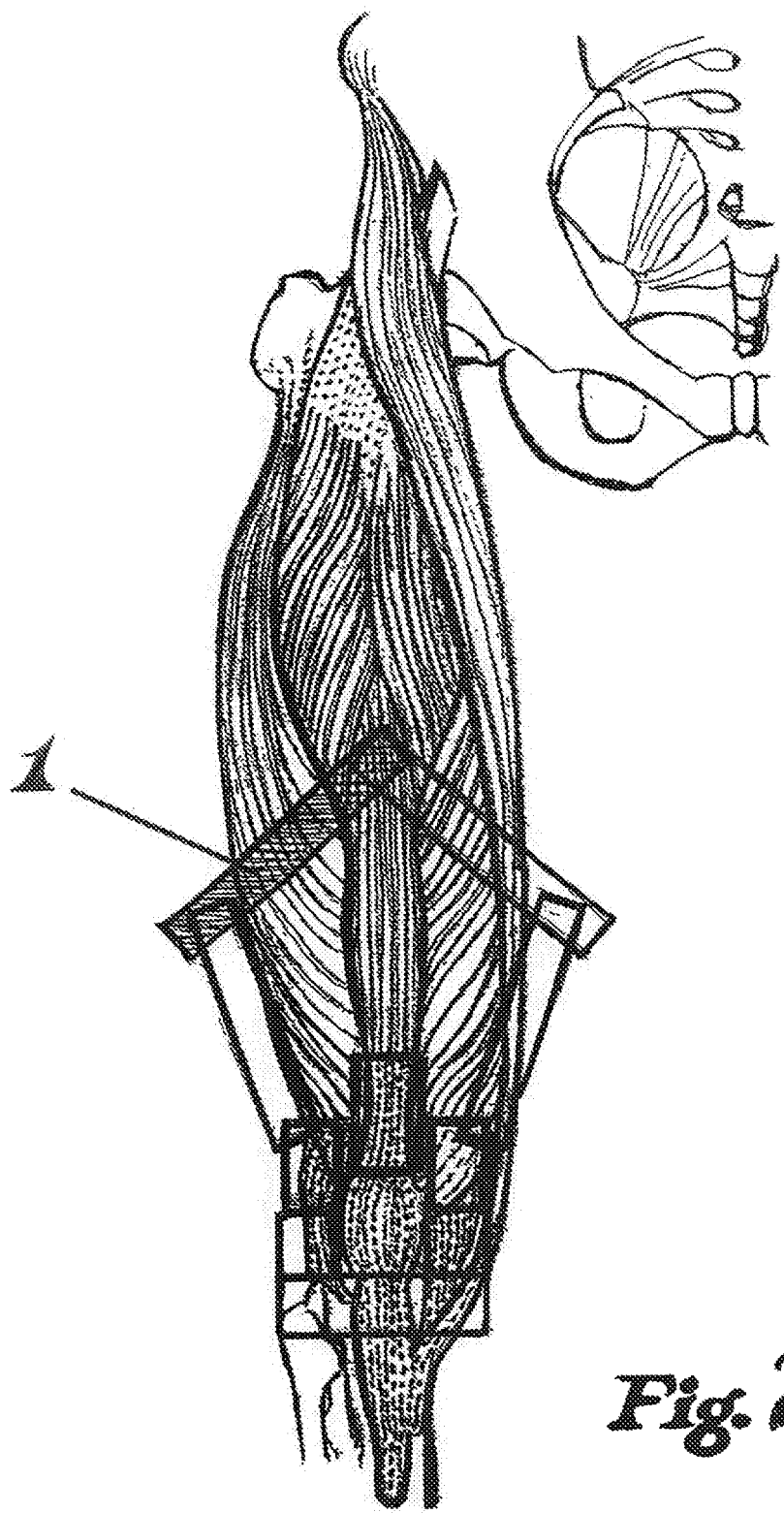

FIG. 29. is a drawing of the application of a second layer of the adhesive medical tape applied to the quadriceps femoris large muscle group for the elicitation taping method. This layer of tape is specifically applied over the first layer of the first piece of tape applied laterally from the rectus femoris to the vastus lateralis.

Figure 30:
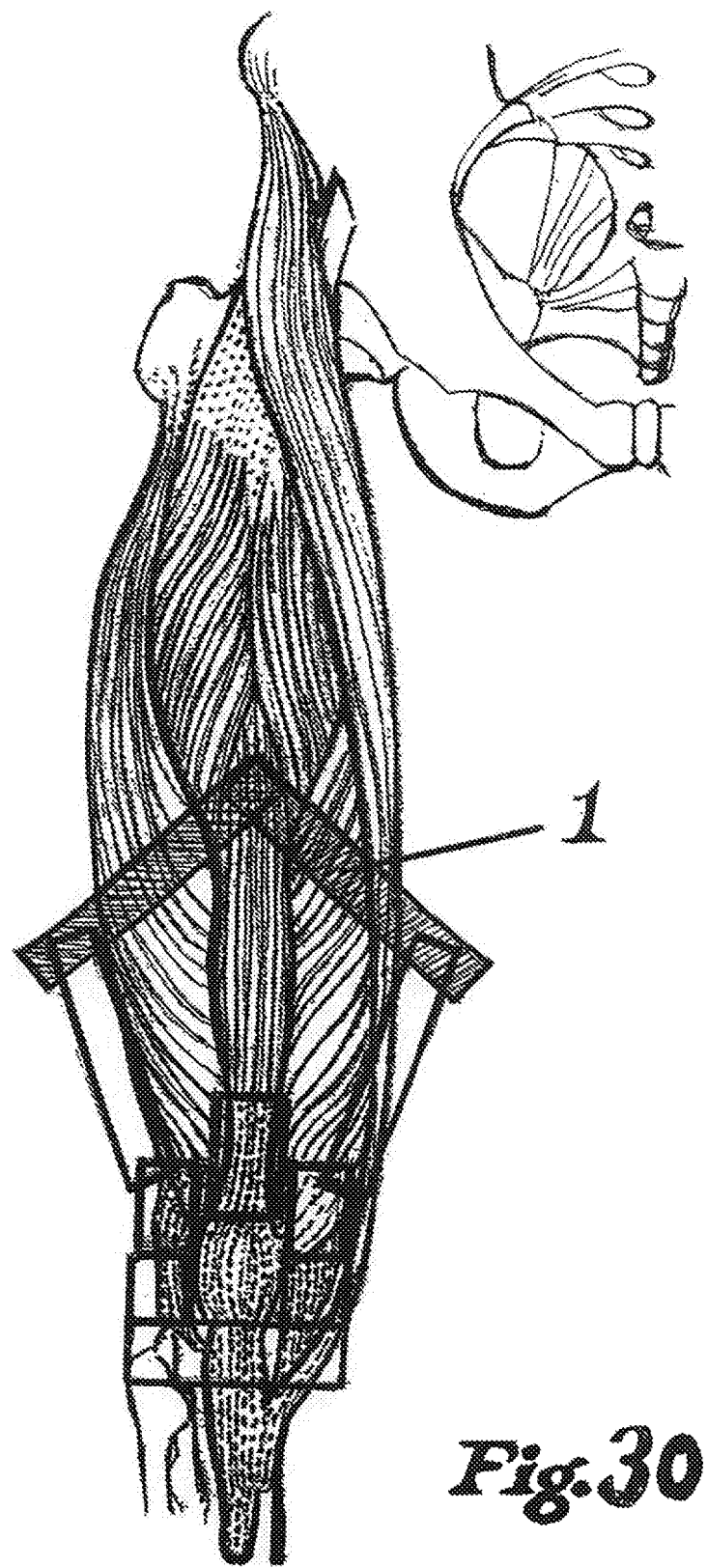

FIG. 30. is a drawing of the application of a second layer of the adhesive medical tape applied to the quadriceps femoris large muscle group for the elicitation taping method. This layer of tape is specifically applied over the first layer of the second piece of tape applied medially from the rectus femoris to the vastus medialis.

Figure 31:
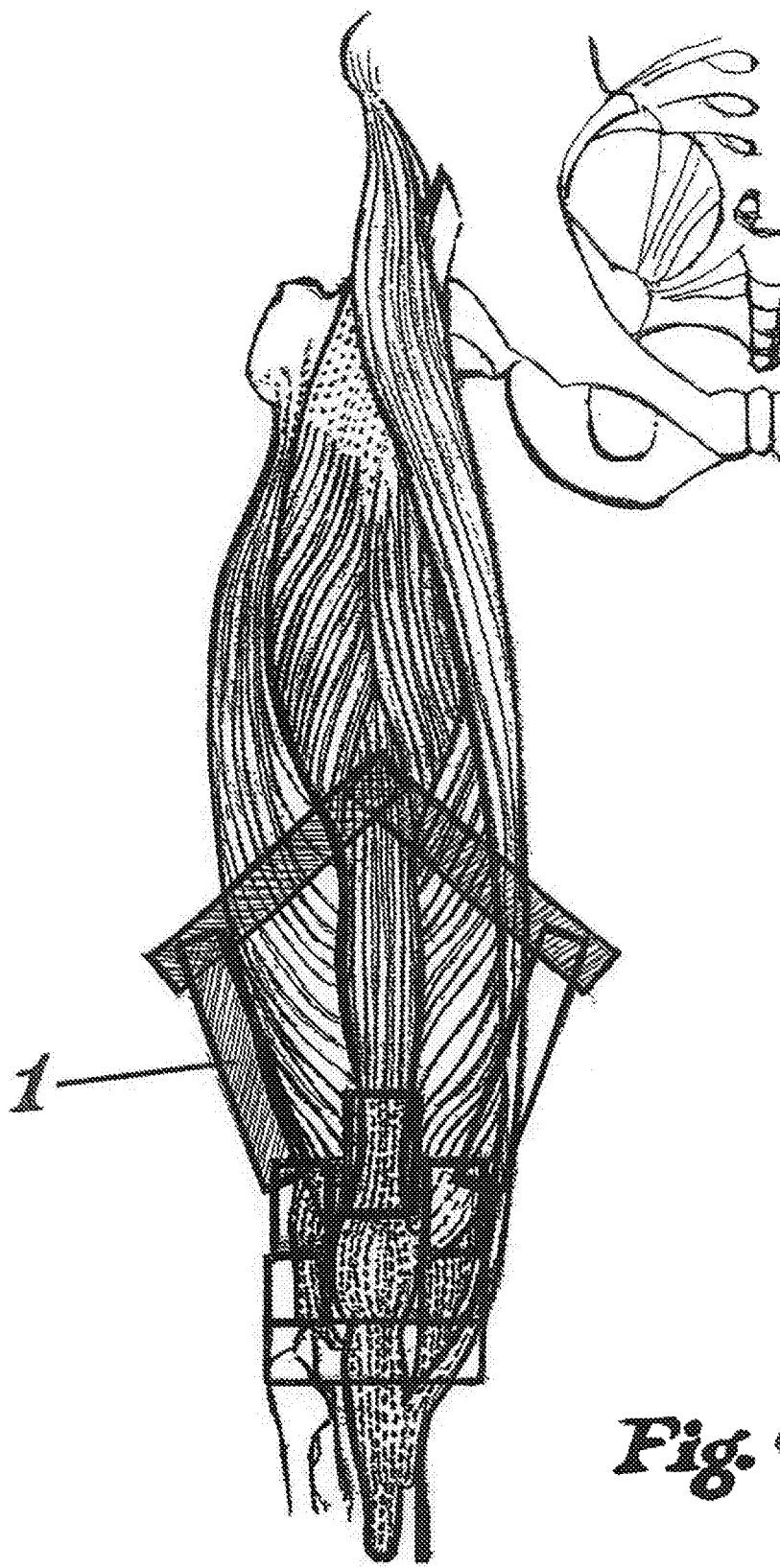

FIG. 31. is a drawing of the application of a second layer of the adhesive medical tape applied to the quadriceps femoris large muscle group for the elicitation taping method. This layer of tape is specifically applied over the first layer of the third piece of tape applied laterally along the muscle of the vastus lateralis to the end of the muscle.

Figure 32:
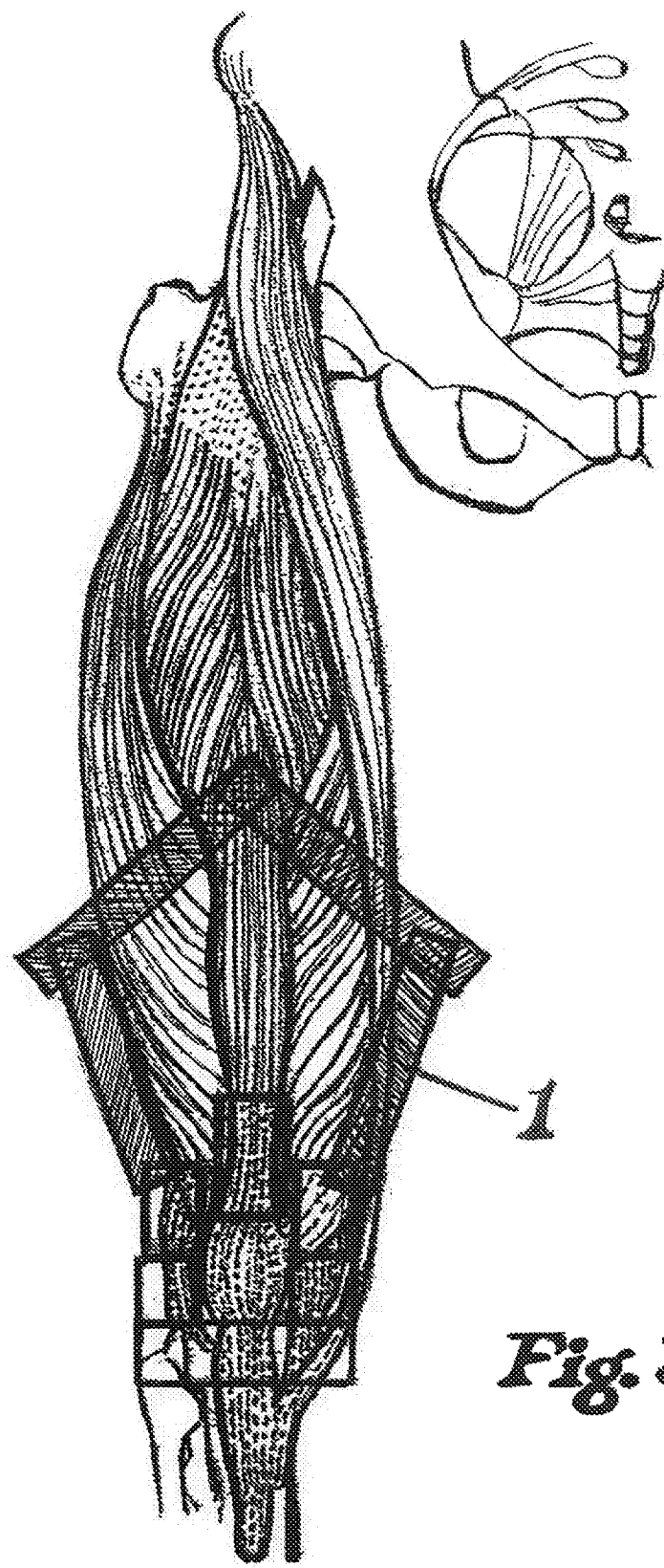

FIG. 32. is a drawing of the application of a second layer of the adhesive medical tape applied to the quadriceps femoris large muscle group for the elicitation taping method. This layer of tape is specifically applied over the first layer of the fourth piece of tape applied medially along the muscle of the vastus medialis to the end of the muscle.

Figure 33:
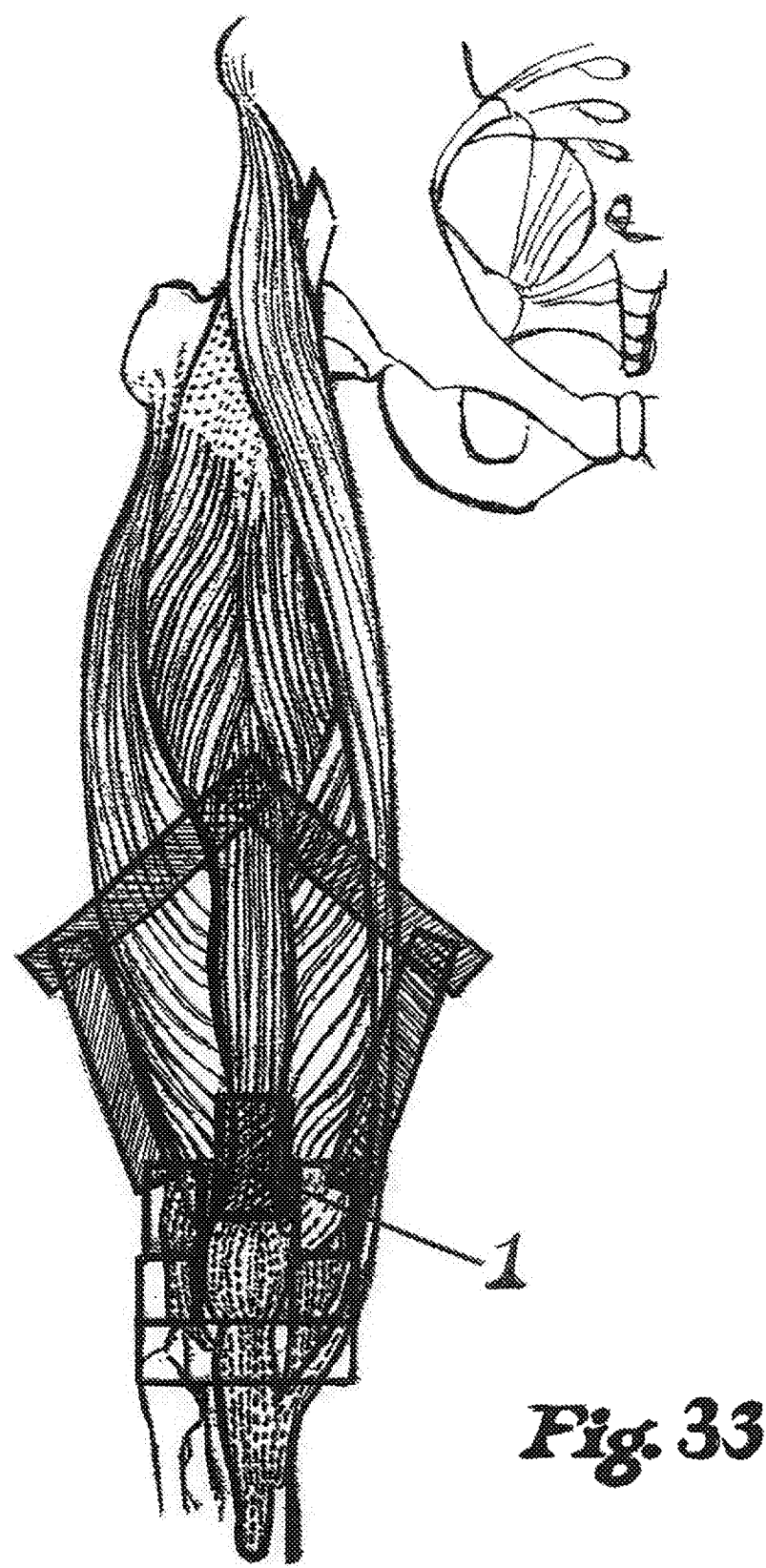
Figure 34:
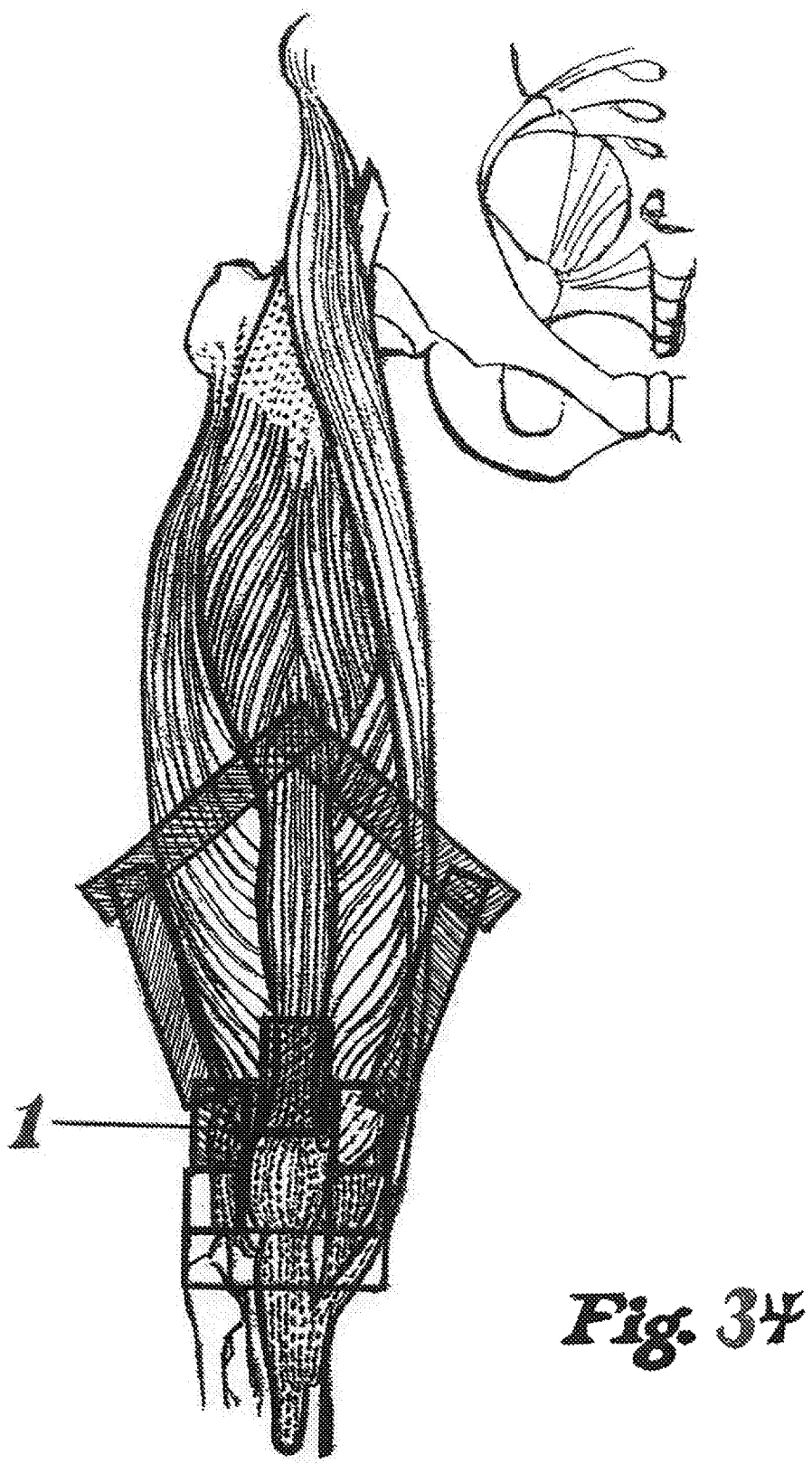

FIG. 33. is a drawing of the application of a second layer of the adhesive medical tape applied to the quadriceps femoris large muscle group for the elicitation taping method. This layer of tape is specifically applied over the first layer of the fifth piece of tape applied centrally along the muscle of the rectus femoris, in series in the myotendinous region of the muscle FIG. 34. is a drawing of the application of a second layer of the adhesive medical tape applied to the quadriceps femoris large muscle group for the elicitation taping method. This layer of tape is specifically applied over the first layer of the sixth piece of tape applied laterally along the myotendinous region, in series and laterally to the patella.

Figure 35:
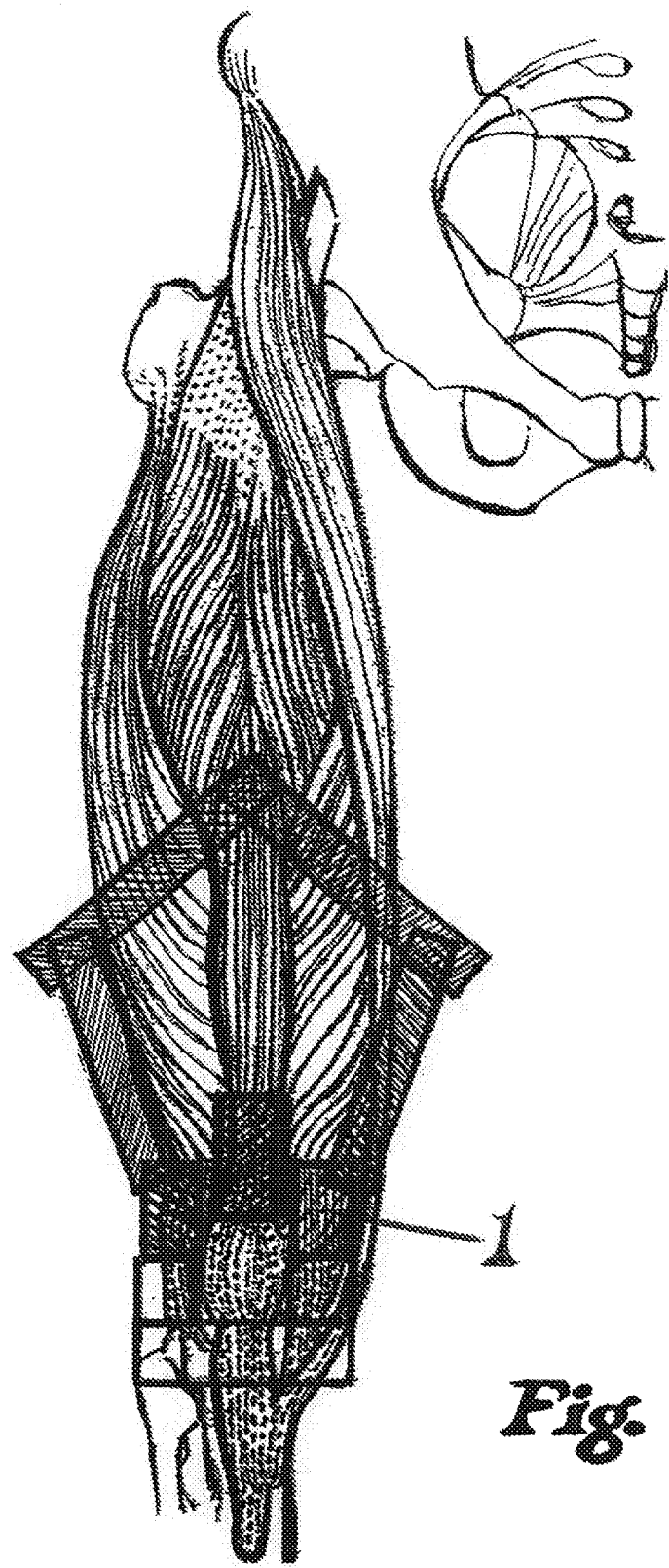

FIG. 35. is a drawing of the application of a second layer of the adhesive medical tape applied to the quadriceps femoris large muscle group for the elicitation taping method. This layer of tape is specifically applied over the first layer of the seventh piece of tape applied medially along the myotendinous region, in series and medially to the patella.

Figure 36:
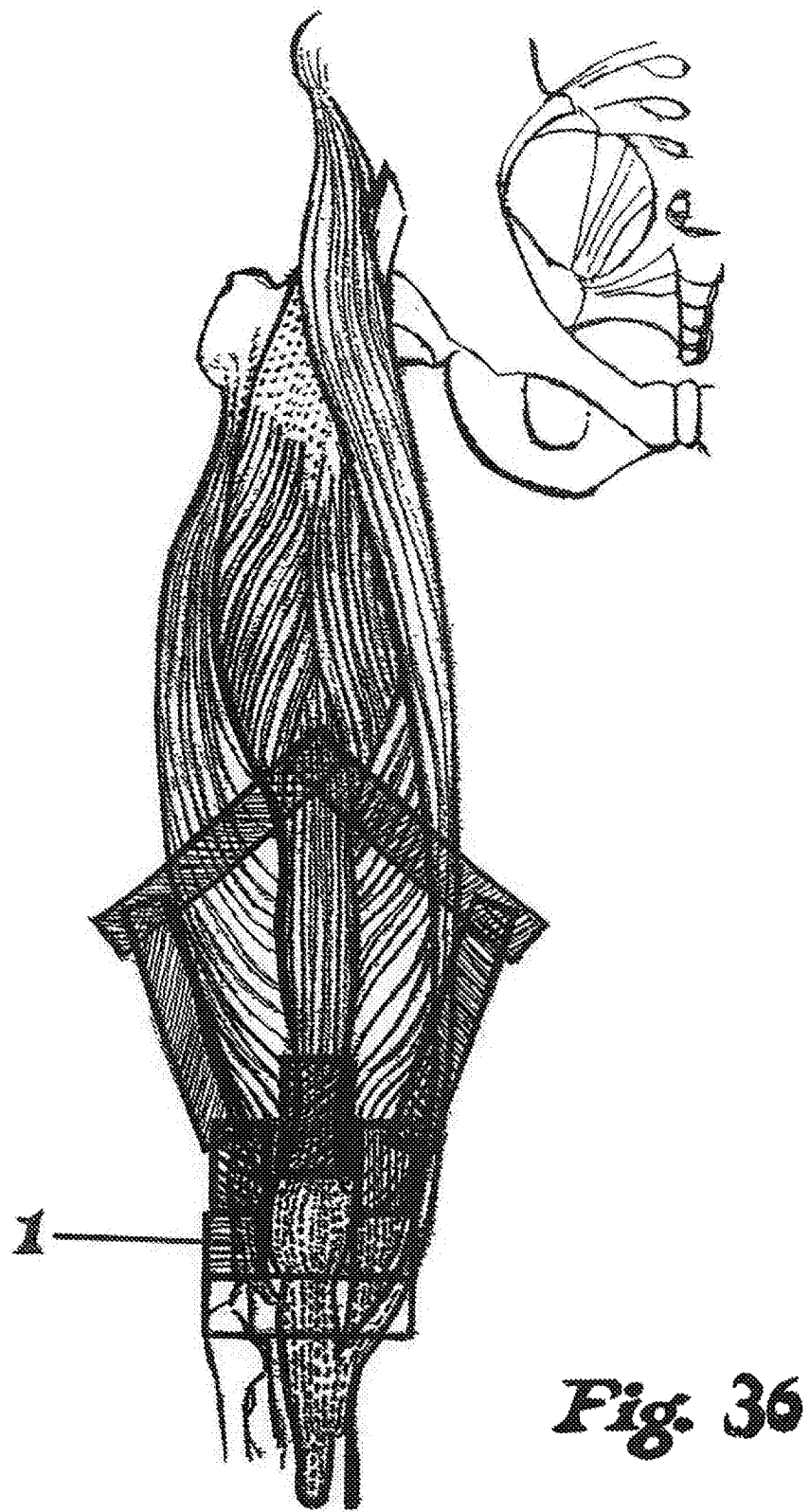

FIG. 36. is a drawing of the application of a second layer of the adhesive medical tape applied to the quadriceps femoris large muscle group for the elicitation taping method. This layer of tape is specifically applied over the first layer of the eight pieces of tape applied laterally along the myotendinous region, in series and laterally to the patella.

Figure 37:
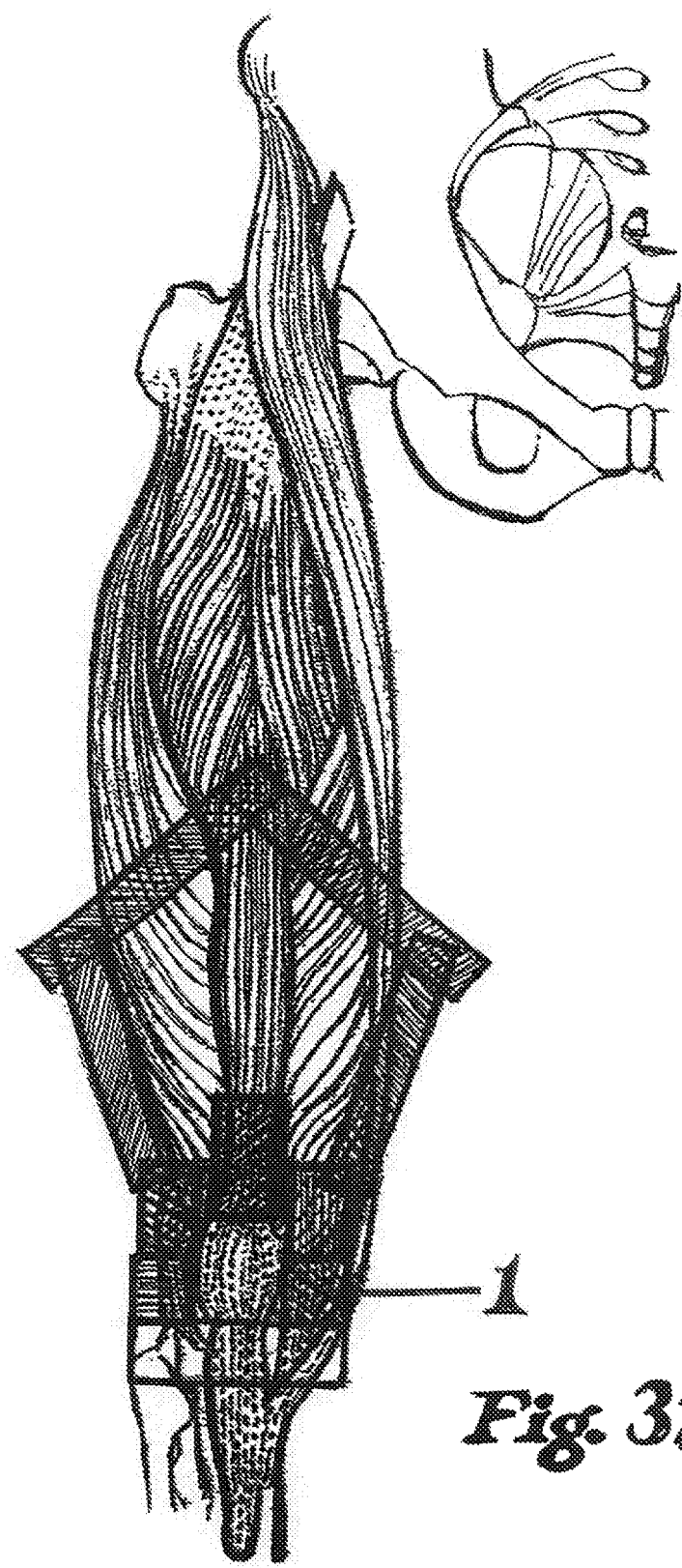

FIG. 37. is a drawing of the application of a second layer of the adhesive medical tape applied to the quadriceps femoris large muscle group for the elicitation taping method. This layer of tape is specifically applied over the first layer of the ninth piece of tape applied medially along the myotendinous region, in series and medially to the patella.

Figure 38:
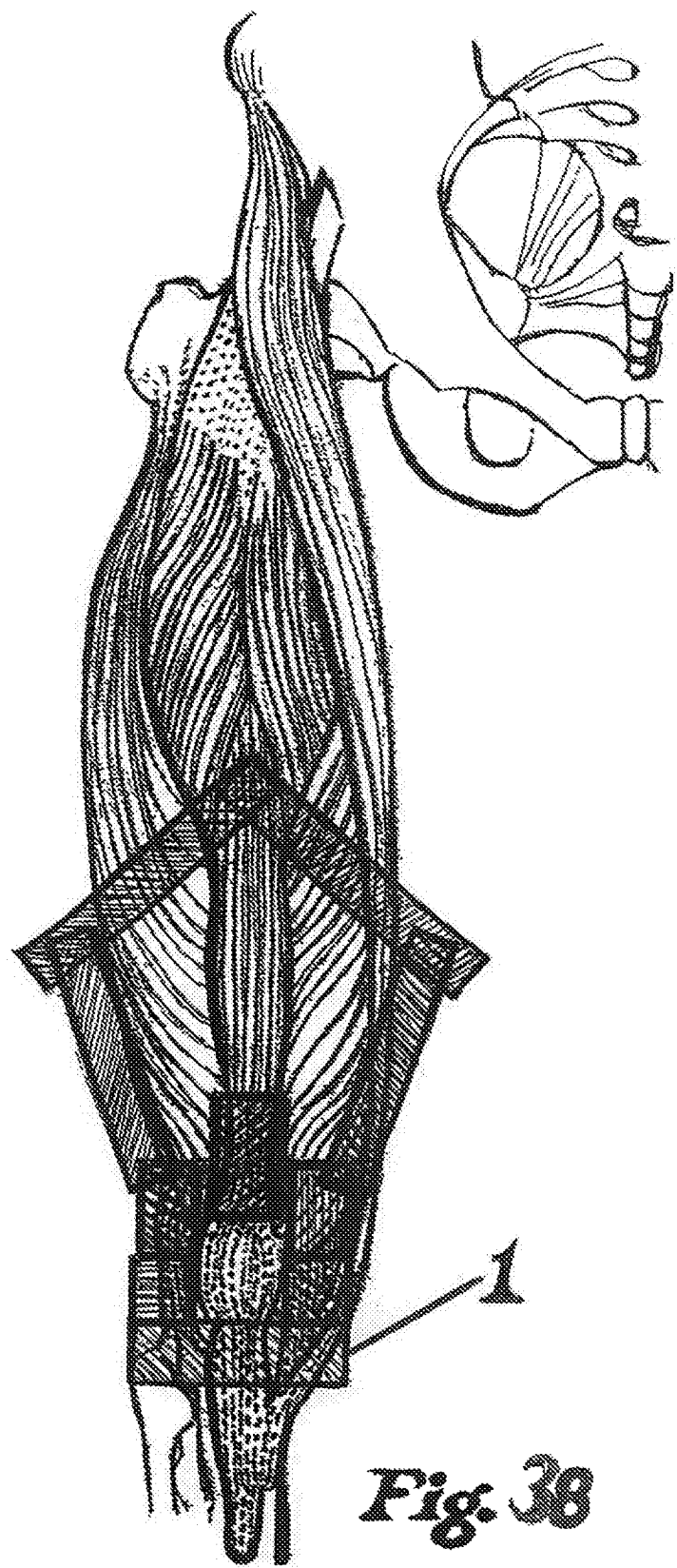

FIG. 38. is a drawing of the application of a second layer of the adhesive medical tape applied to the quadriceps femoris large muscle group for the elicitation taping method. This layer of tape is specifically applied over the first layer of the tenth piece of tape applied centrally along the myotendinous region, in series and inferior to the patella.

Figure 39:
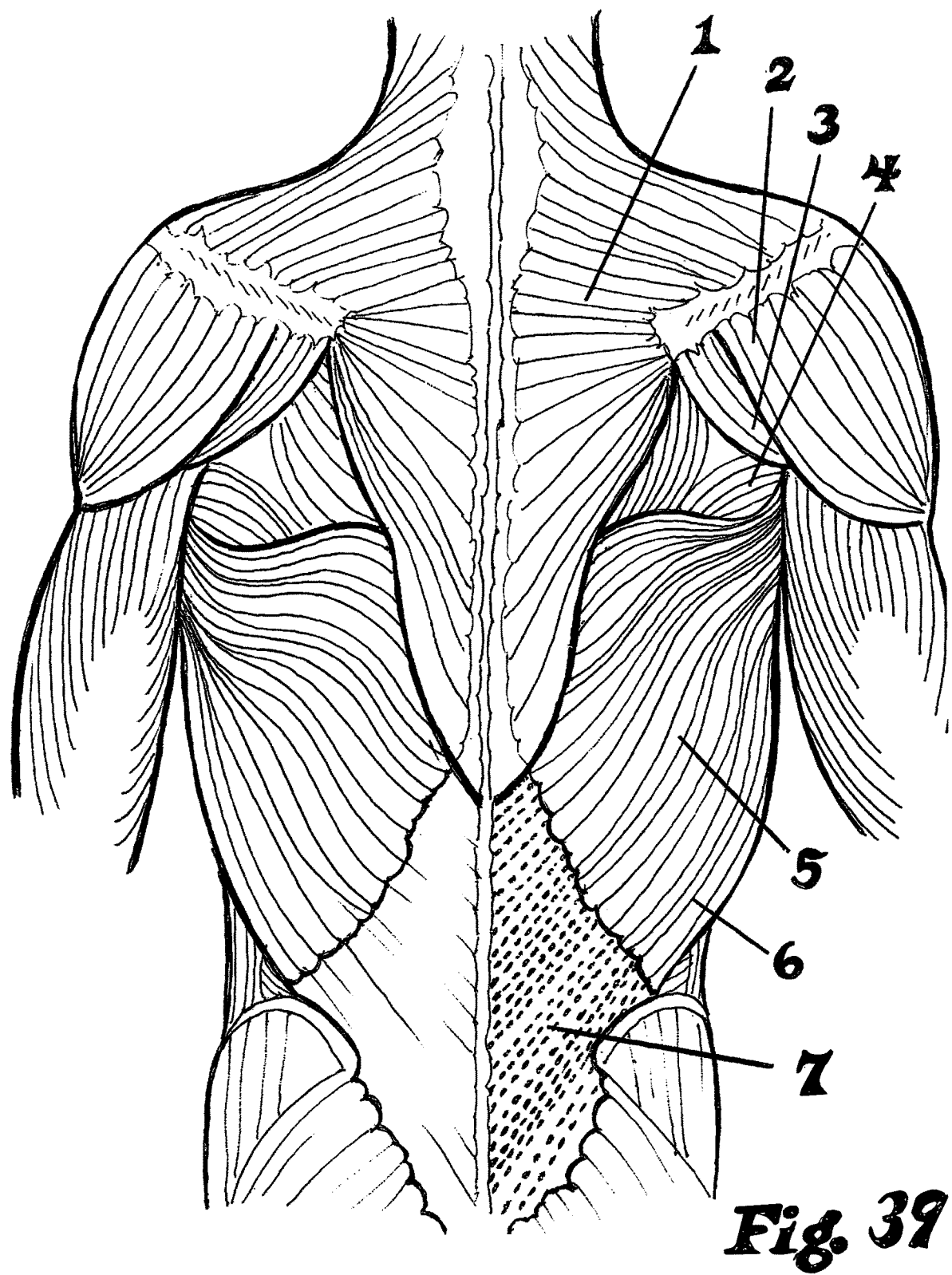
Figure 40:
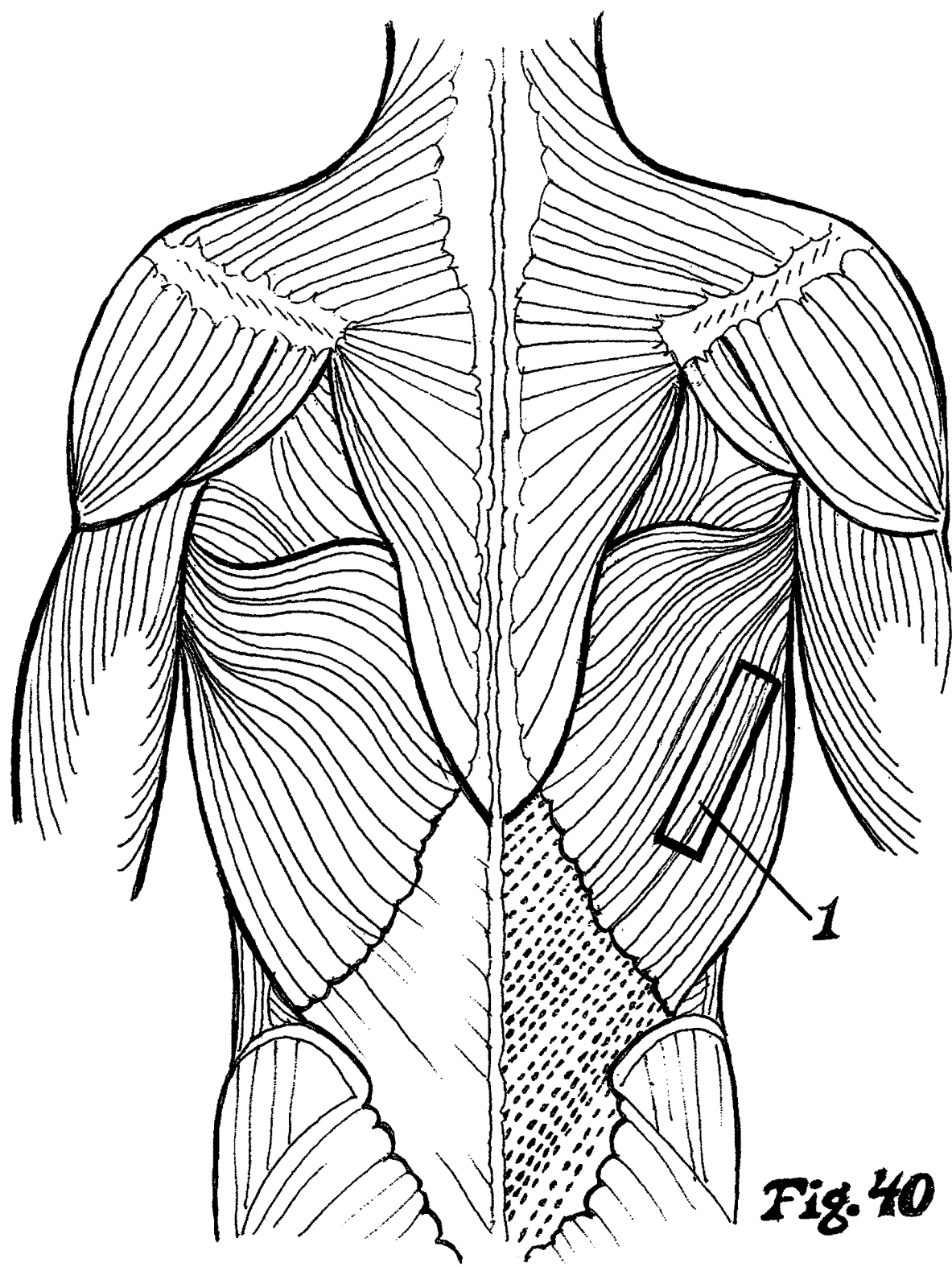

FIG. 39. is a drawing of the latissimus dorsi muscle. The right side of the muscle will be the targeted region for the taping method. 1. trapezius 2. deltoid 3. fibers of posterior deltoid (spinal part) 4. teres major 5. latissimus dorsi. 6. muscle fiber (extrafusal fiber) 7. myotendinous junction FIG. 40. is a drawing of the application of adhesive medical tape applied to the latissimus dorsi for the inhibition taping method. 1. The first piece of tape is applied laterally along the muscle in parallel to the muscle fibers in the belly of the muscle.

Figure 41:
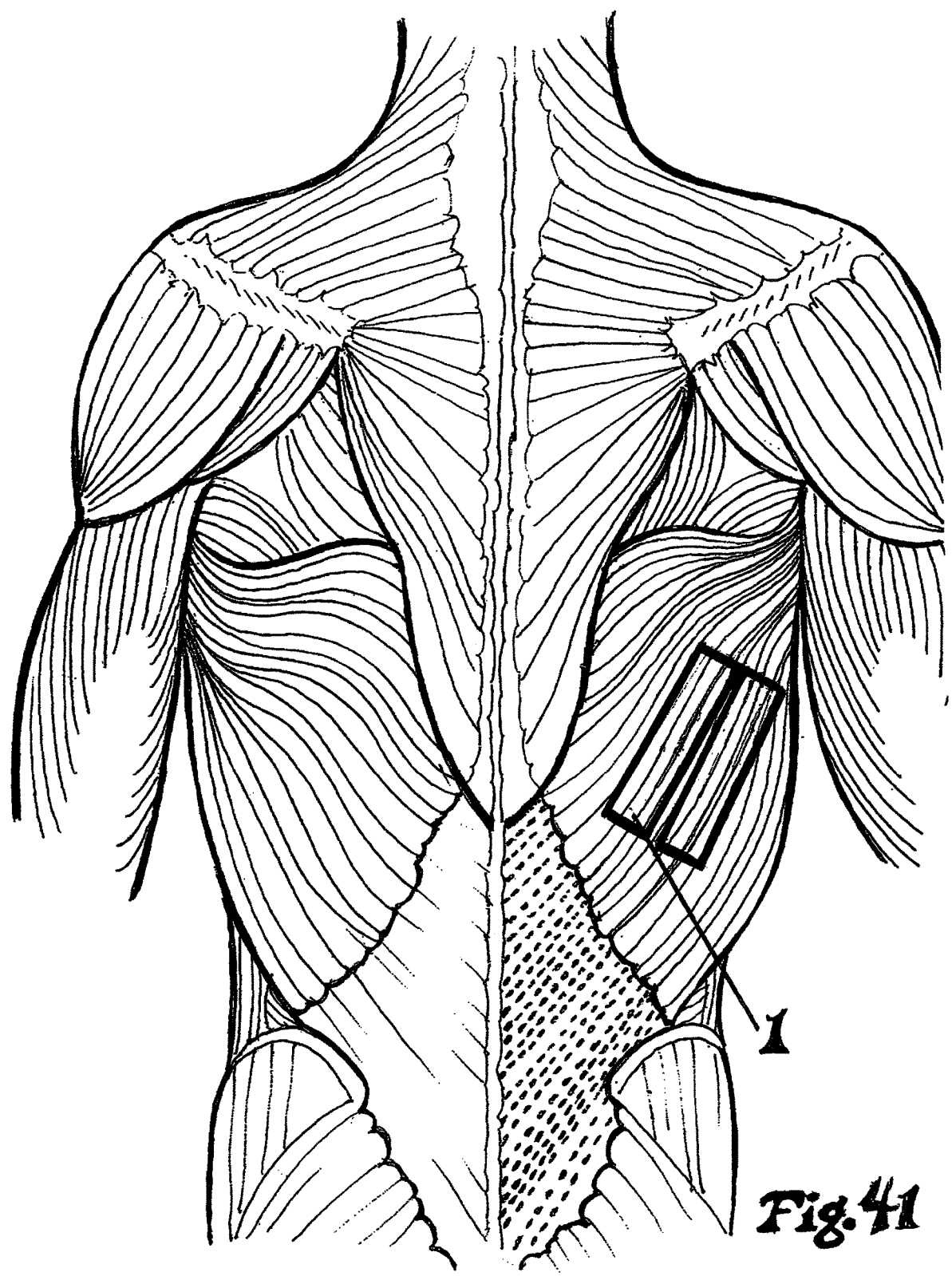

FIG. 41. is a drawing of the application of adhesive medical tape applied to the latissimus dorsi for the inhibition taping method. 1. The second piece of tape is applied centrally along the muscle in parallel to the muscle fibers in the belly of the muscle.

Figure 42:
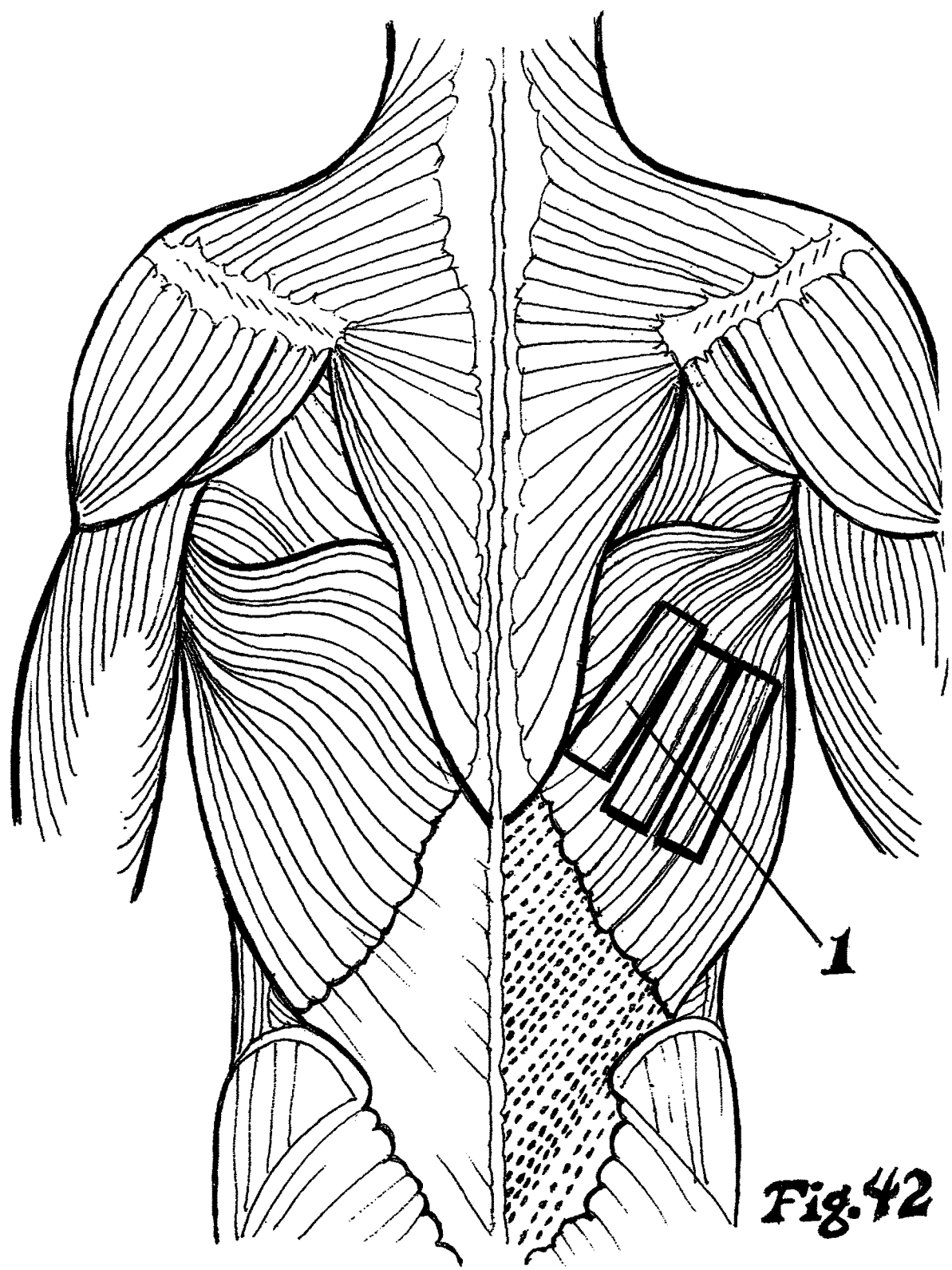

FIG. 42. is a drawing of the application of adhesive medical tape applied to the latissimus dorsi for the inhibition taping method. 1. The third piece of tape is applied medially along the muscle in parallel to the muscle fibers in the belly of the muscle.

Figure 43:
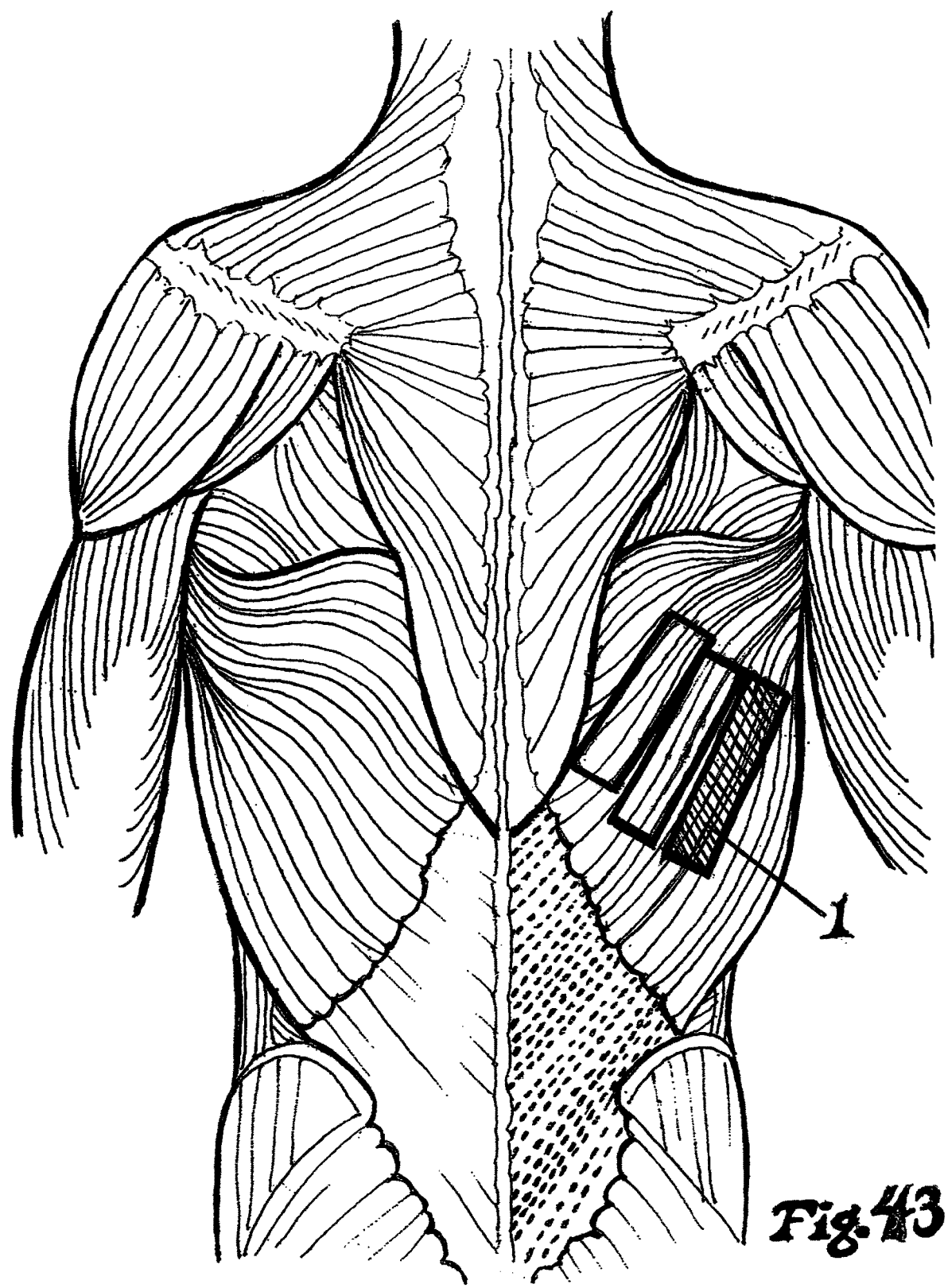

FIG. 43. is a drawing of a second layer of the application of adhesive medical tape applied to the latissimus dorsi for the inhibition taping method. 1. This layer of tape is specifically applied over the first layer of the first piece of tape laterally applied.

Figure 44:
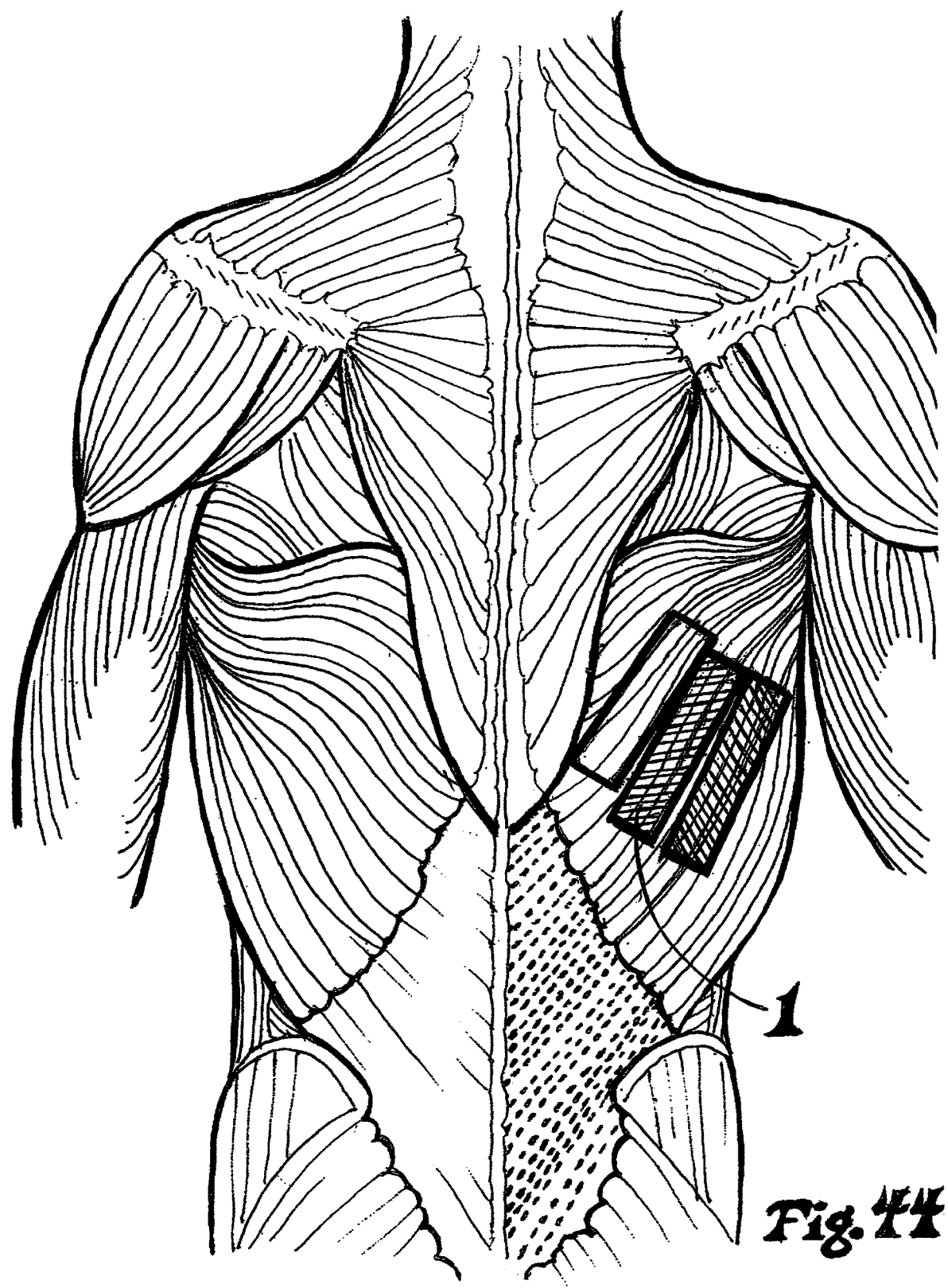

FIG. 44. is a drawing of a second layer of the application of adhesive medical tape applied to the latissimus dorsi for the inhibition taping method. 1. This layer of tape is specifically applied over the first layer of the second piece of tape centrally applied.

Figure 45:
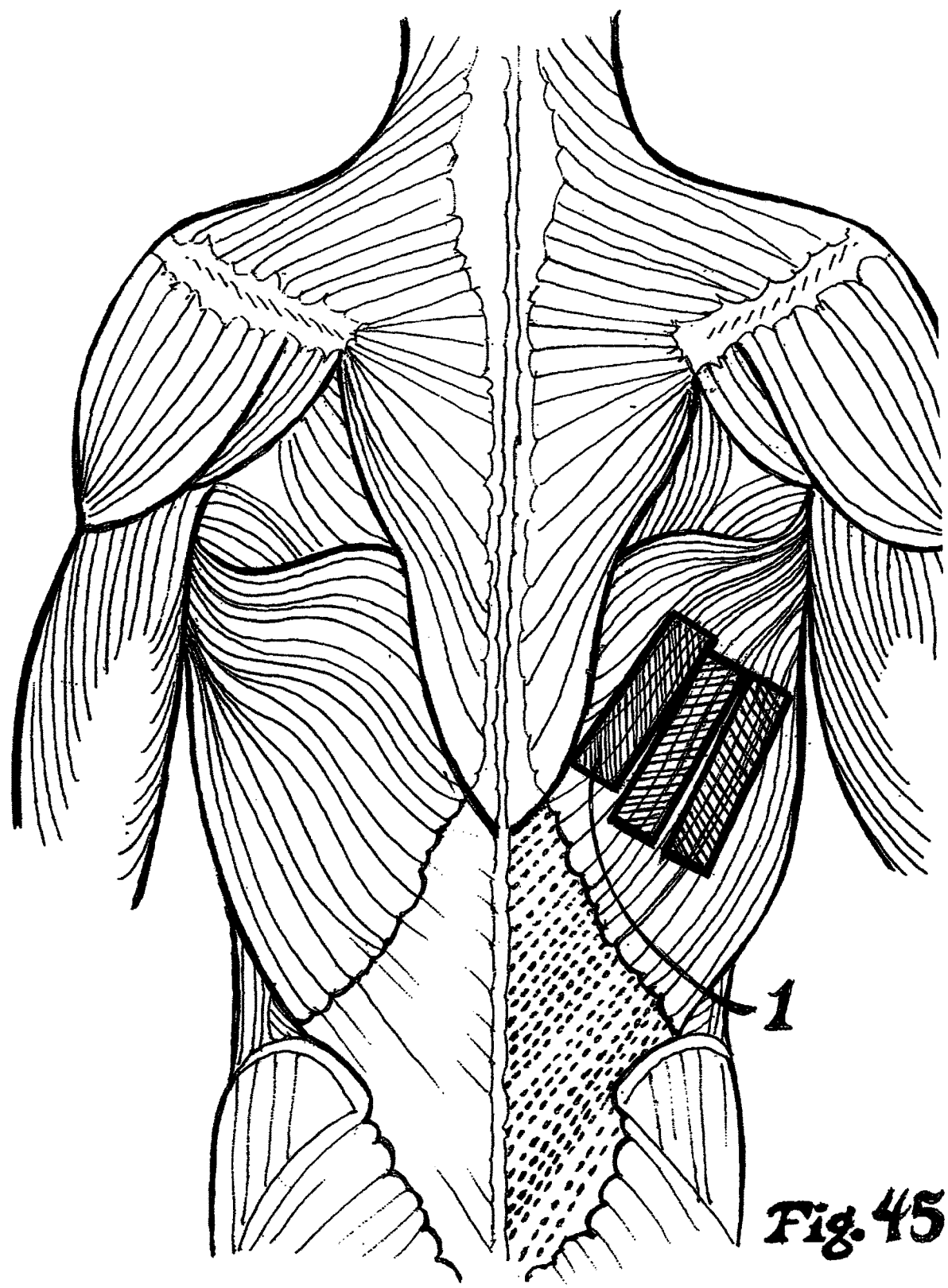

FIG. 45. is a drawing of a second layer of the application of adhesive medical tape applied to the latissimus dorsi for the inhibition taping method. 1. This layer of tape is specifically applied over the first layer of the third piece of tape medially applied.

Figure 46:
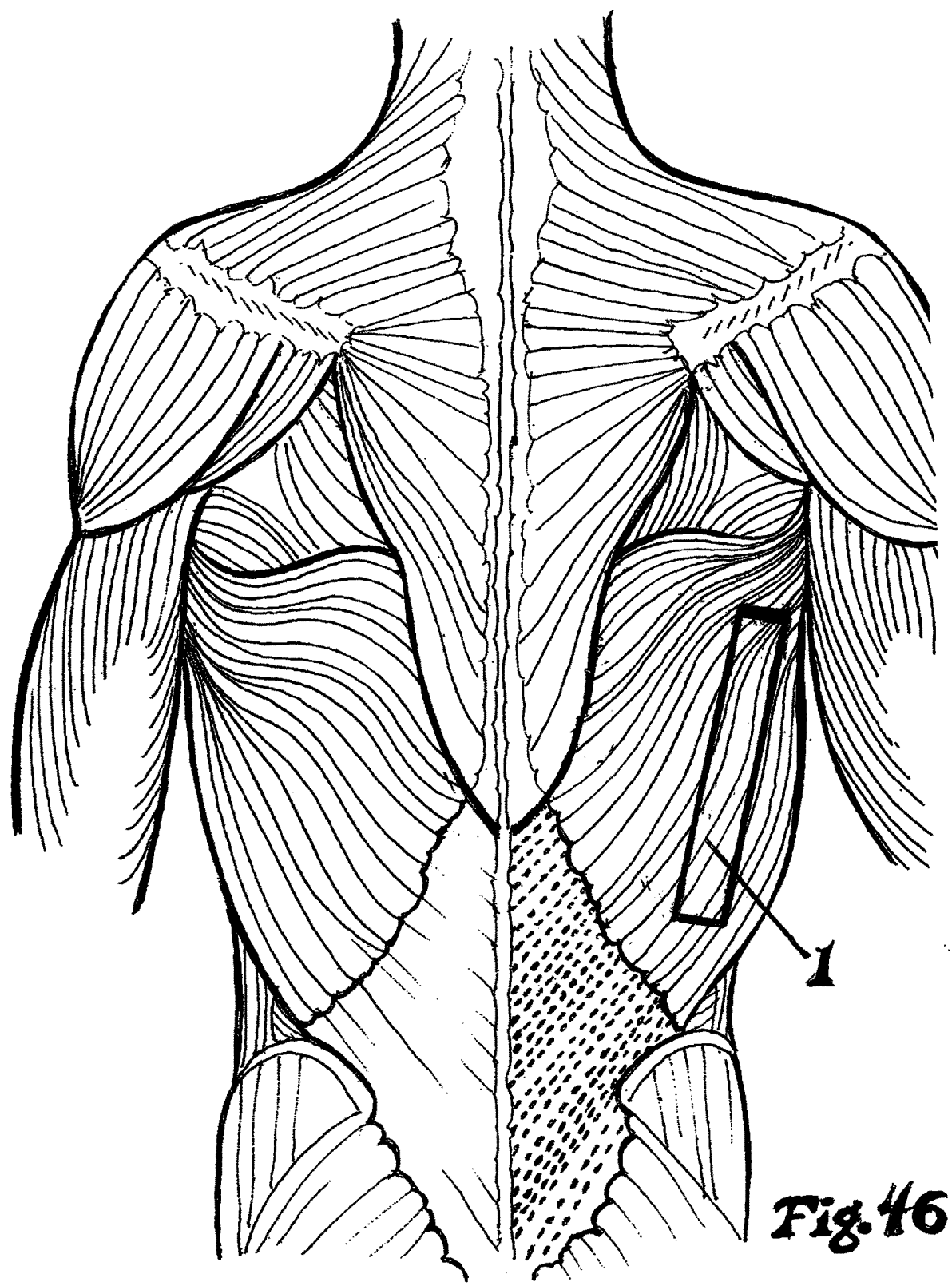

FIG. 46. is a drawing of the application of adhesive medical tape applied to the latissimus dorsi for the elicitation taping method. 1. The first piece of tape is applied laterally starting the outline of a smaller version of the muscle, going towards the origin of the muscle.

Figure 47:
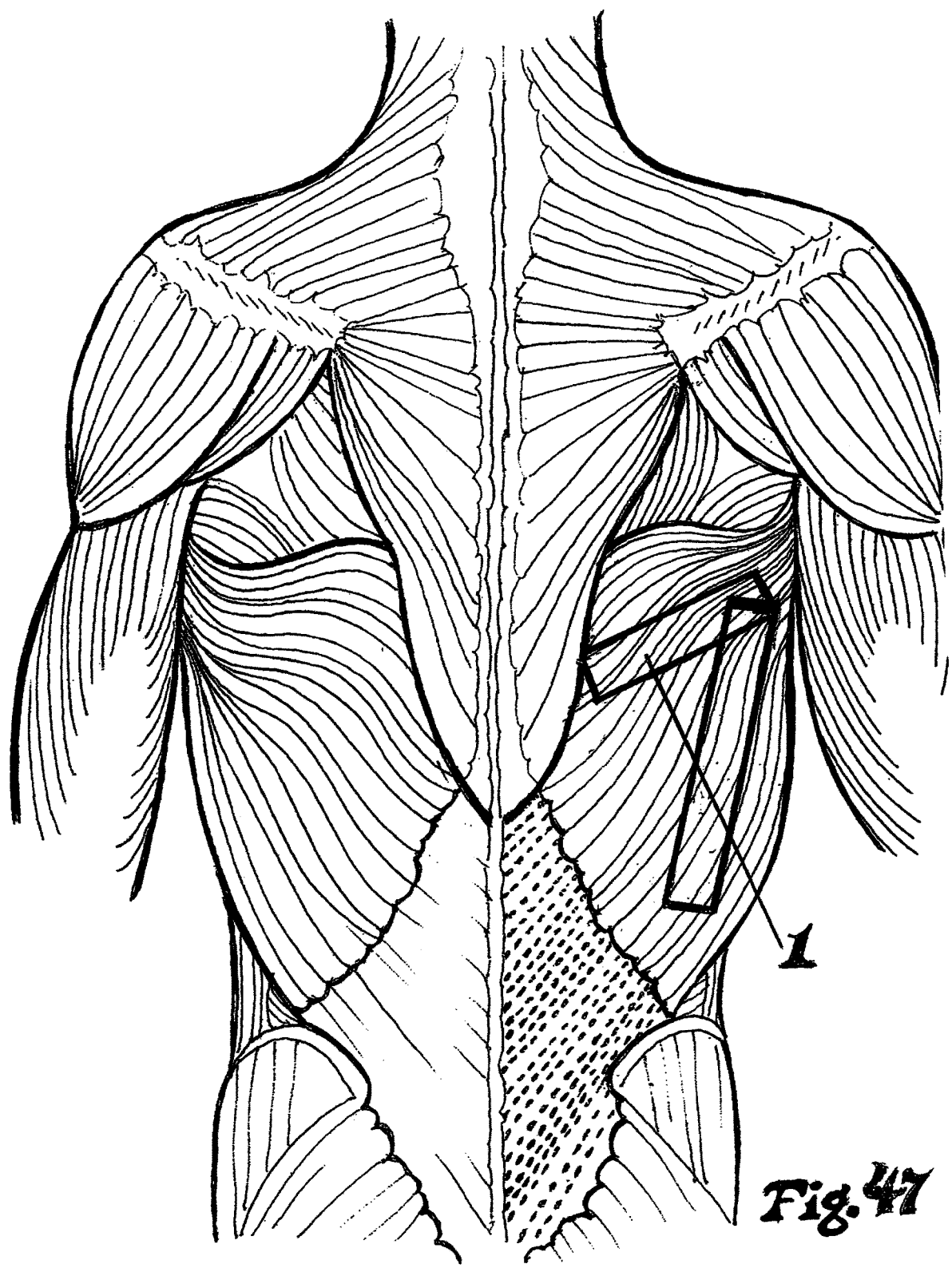

FIG. 47. is a drawing of the application of adhesive medical tape applied to the latissimus dorsi for the elicitation taping method. 1. The second piece of tape is applied medially at an angle forming an angle with the first piece of tape applied continuing the outline of the smaller version of the muscle, going towards the origin of the muscle.

Figure 48:
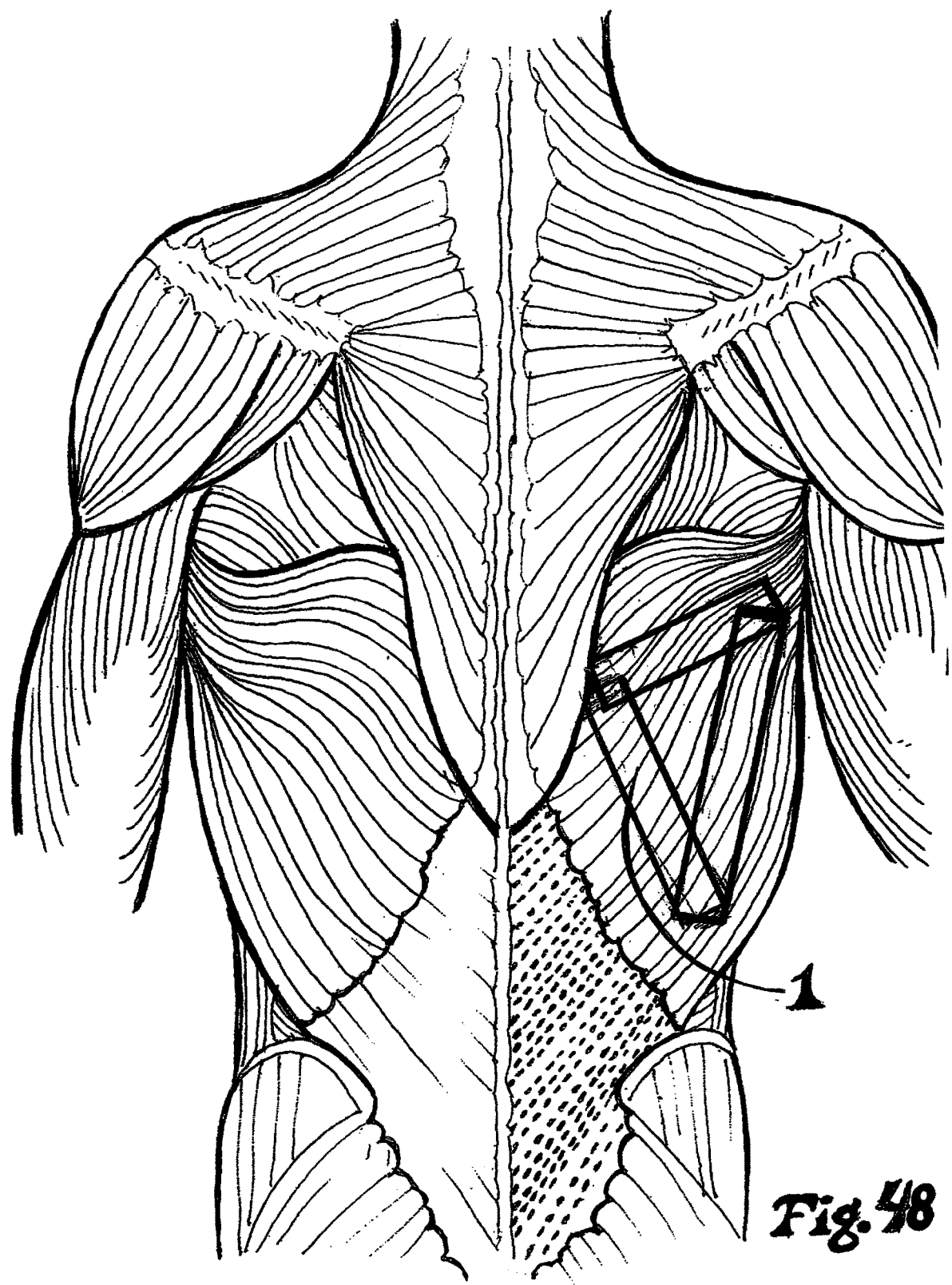

FIG. 48. is a drawing of the application of adhesive medical tape applied to the latissimus dorsi for the elicitation taping method. 1. The third piece of tape is applied centrally and distally completing the enclosure of the other two pieces of tape applied. The smaller version of the muscle is completed.

Figure 49:
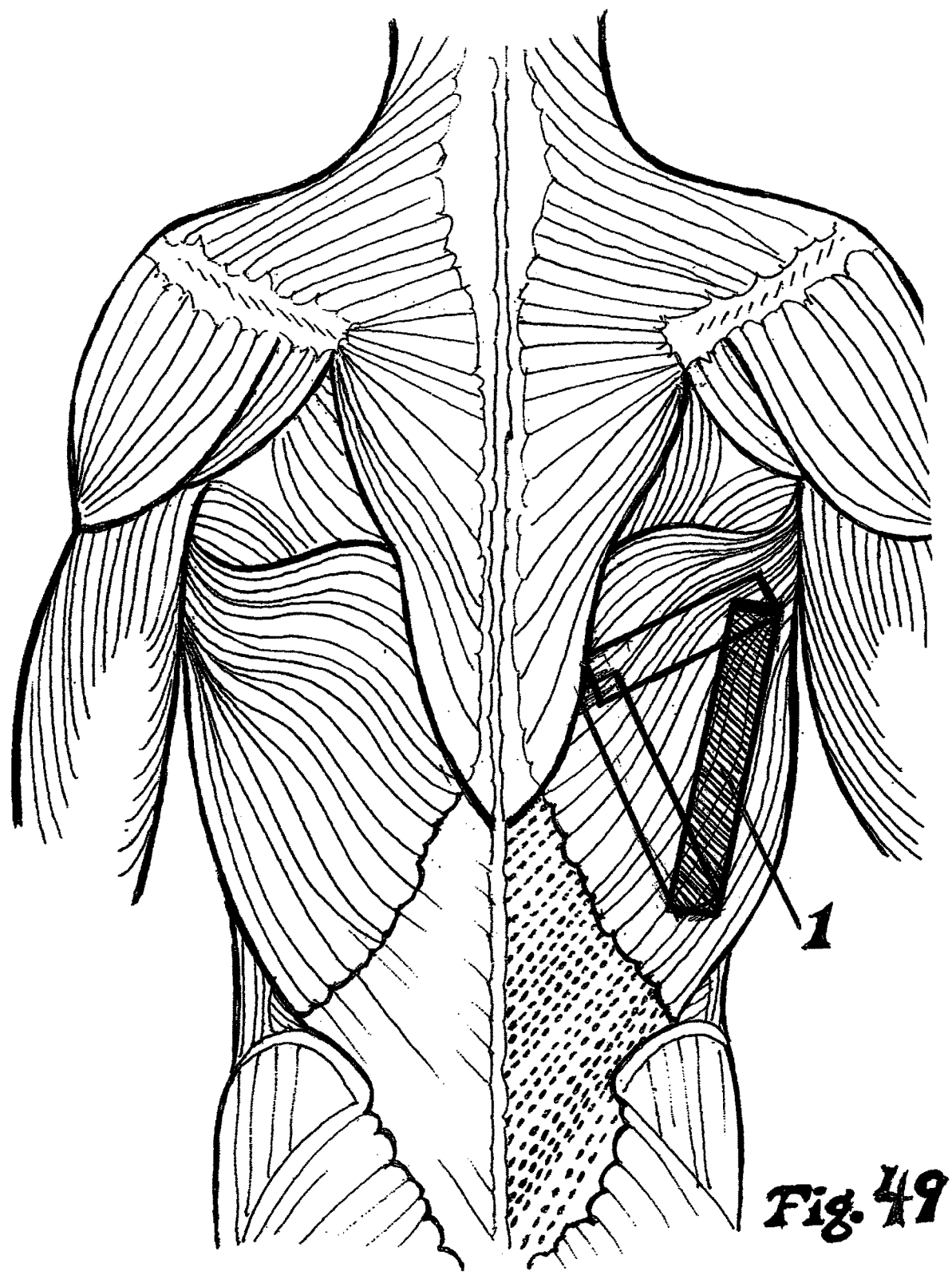

FIG. 49. is a drawing of the application of a second layer of adhesive medical tape applied to the latissimus dorsi for the elicitation taping method. 1. This layer of tape is specifically applied over the first layer of the first piece of tape applied laterally starting the outline of the smaller version of the muscle, going towards the origin.

Figure 50:
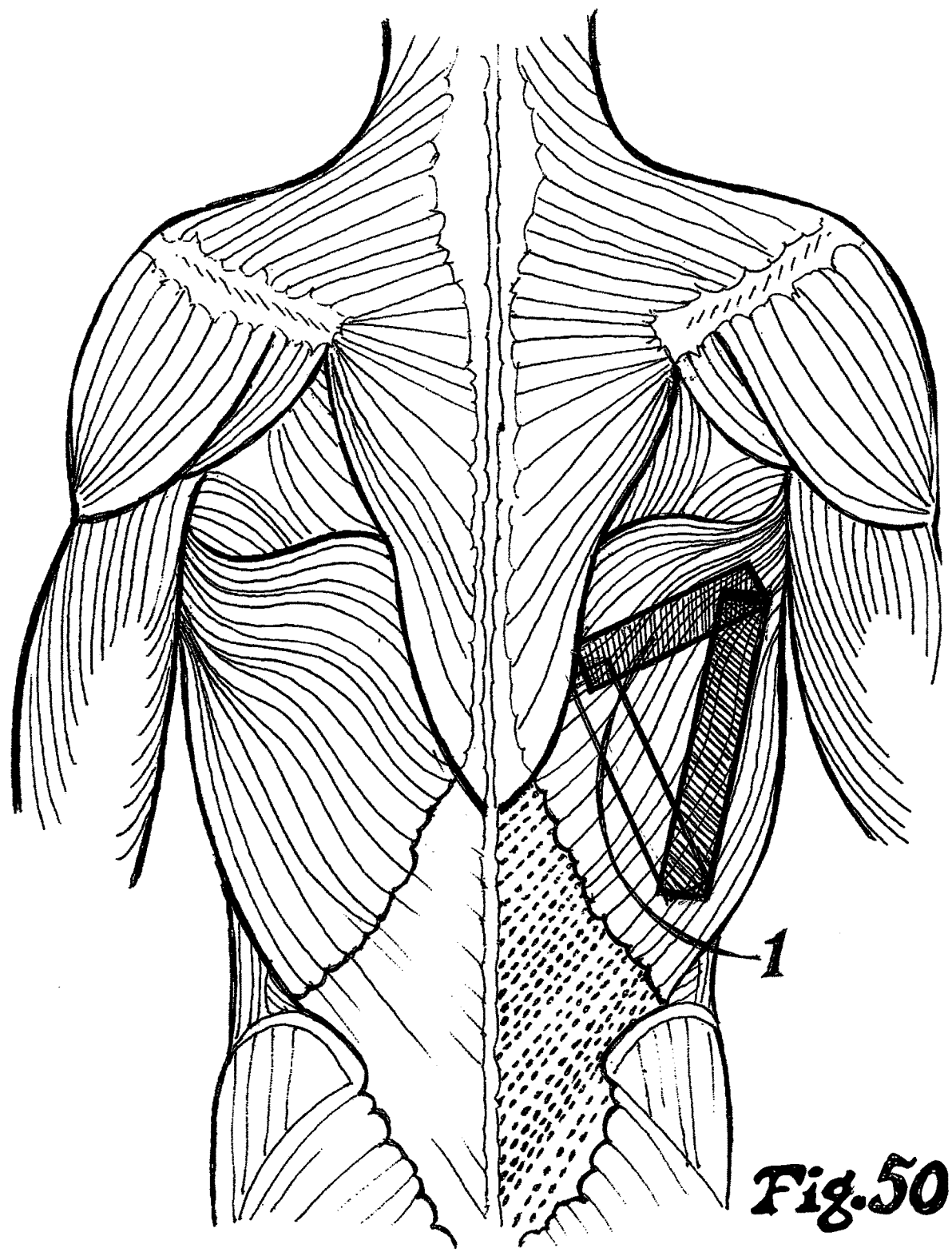
Figure 51:
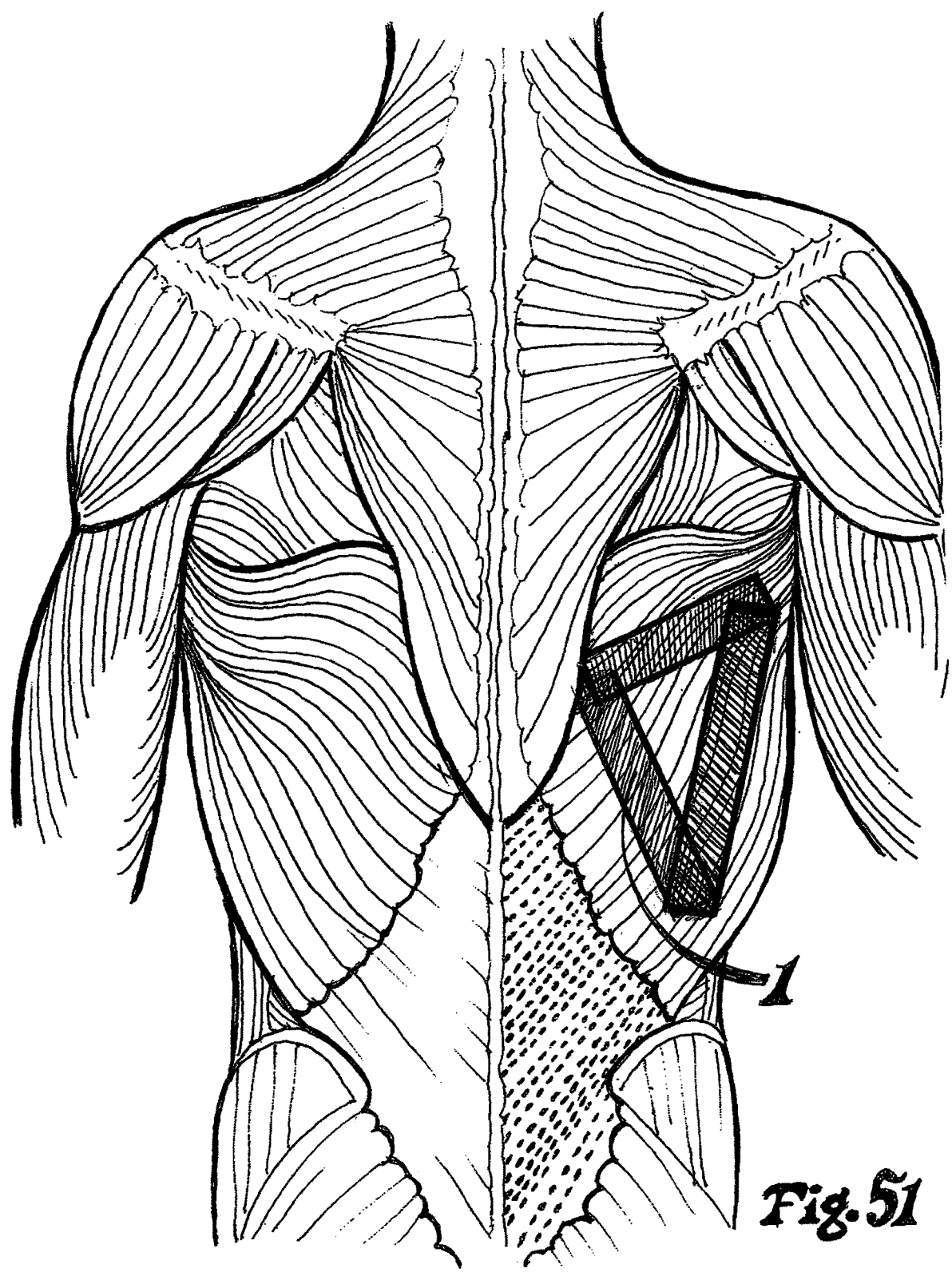

FIG. 50. is a drawing of the application of a second layer of adhesive medical tape applied to the latissimus dorsi for the elicitation taping method. 1. This layer of tape is specifically applied over the first layer of the second piece of tape applied medically at an angle forming an angle with the first piece of tape applied continuing the outline of the smaller version of the muscle, going towards the origin of the muscle FIG. 51. is a drawing of the application of a second layer of adhesive medical tape applied to the latissimus dorsi for the elicitation taping method. 1. This layer of tape is specifically applied to the third piece of tape is applied centrally and distally completing the enclosure of the other two pieces of tape applied. The smaller version of the muscle is completed with two layers of tape.

While certain preferred embodiments of the present invention have been disclosed in detail, it is to be understood that various modifications may be adopted without departing from the spirit of the invention or scope of the following claims.

I claim:

1. A method to control tone is a skeletal muscle, the skeletal muscle including lateral and medical surfaces, each lateral and medial surface further having a proximal and distal segments, the muscle further including proximal and distal myotendinous regions, the method comprising the steps of:
- (a) forming a web of tape section that joins the original origin of the muscle to enclose at least a portion of the muscle, comprising the steps of:
  - (A) applying at least a first piece of adhesive tape to skin covering one of the myotendinous regions, and in particular, the origin in series along the myotendinous region; and
  - (B) applying at least a second piece of adhesive tape to skin covering an edge of at least a portion of one of the lateral and medial surfaces, thereby activating proprioceptors and mechanoreceptors in the muscle, wherein the step of applying at least a second piece of adhesive tape to skin further comprises selecting a new point of insertion.

2. The method of claim 1, further comprising the steps of:
- (d) applying at least a third piece of adhesive tape to skin laterally from the myotendinous region along the muscle towards the new insertion;
- (e) applying at least a fourth piece of adhesive tape to skin medially from the myotendinous region along the muscle towards the new insertion, forming an angle with at least one of the pieces of adhesive tape and encasing part of the muscle; and
- (f) applying at least a fifth piece of adhesive tape to skin from lateral to medial to join to the new insertion, taping towards the new insertion such that the fifth piece of adhesive tape forms an angle with at least one of the pieces of adhesive tape encasing the distal portion of the muscle.

3. The method of claim 2, wherein the step of applying at least a second piece of adhesive tape further comprises:
- (A) forming a web of tape section that joins the original insertion of the muscle to enclose at least a portion of the muscle and elicits skeletal muscle tone in large muscles and large muscle groups, comprising the steps of:
  - (i) applying at least a sixth piece of adhesive tape laterally to medially to form an angle at a new origin;
  - (ii) applying at least a seventh piece of adhesive tape laterally along the muscle from the new origin going towards the insertion;
  - (iii) applying at least an eighth piece of adhesive tape medially from the new origin going towards the insertion along the muscle, forming an angle with at least one of the lateral pieces of tape and encasing part of the area to be elicited; and
  - (iv) applying at least a ninth piece of adhesive tape from lateral to medial to join to the insertion, taping towards the insertion such that the ninth piece of adhesive tape forms an angle with at least one of the pieces of adhesive tape encasing the distal portion of the muscle.

4. A method to control tone in a skeletal muscle, the method comprising the step of:
- (a) applying tape to outline the original muscle within the muscle, wherein the step of applying tape further comprises the steps of:
  - (A) creating a starting point by applying at least a first piece of adhesive tape first proximally to skin at the selected starting points to extend laterally from the starting point to the end point, ending at the end points;
  - (B) applying at least a second piece of adhesive tape medially to skin from the starting point going toward the end point, and ending at the end points of insertion; and
  - (C) applying at least a third piece of adhesive tape sufficient to complete the encasing to create a new smaller version of the muscle itself located within the muscle.

5. A method for increasing tension in at least a portion of a skeletal muscle, the method comprising the steps of:
- (a) selecting a new origin and a new insertion;
- (b) starting at skin covering the selected point of origin, applying tape proximally to create the new origin wherein the step of applying tape proximally further comprises the steps of;
- (A) applying at least a first piece of adhesive tape laterally originating at skin covering the new point of origin towards the new insertion and ending at skin covering the new point of insertion;
- (B) creating the new insertion point by applying at least a second piece of adhesive tape from skin covering the selected insertion point from lateral to medial to skin covering the new origin.

\* \* \* \* \*